United States Patent
Cigan et al.

(10) Patent No.: US 9,951,346 B2
(45) Date of Patent: *Apr. 24, 2018

(54) METHODS AND COMPOSITIONS FOR TARGETED INTEGRATION IN A PLANT

(75) Inventors: Andrew Mark Cigan, Johnston, IA (US); Saverio Carl Falco, Wilmington, DE (US); Huirong Gao, Johnston, IA (US); Michael W. Lassner, Urbandale, IA (US); Zhongsen Li, Hockessin, DE (US); Zhan-Bin Liu, West Chester, PA (US); Leszek A. Lyznik, Johnston, IA (US); David J. Peterson, Ames, IA (US); Christopher Jay Scelonge, Des Moines, IA (US)

(73) Assignees: Pioneer Hi-Bred International, Inc., Johnston, IA (US); E. I. du Pont de Nemours and Company, Wilmington, DE (US)

( * ) Notice: Subject to any disclaimer, the term of this patent is extended or adjusted under 35 U.S.C. 154(b) by 1028 days.

This patent is subject to a terminal disclaimer.

(21) Appl. No.: 14/236,597

(22) PCT Filed: Jul. 18, 2012

(86) PCT No.: PCT/US2012/047202
§ 371 (c)(1),
(2), (4) Date: Jul. 28, 2014

(87) PCT Pub. No.: WO2013/019411
PCT Pub. Date: Feb. 7, 2013

(65) Prior Publication Data
US 2014/0338070 A1 Nov. 13, 2014

Related U.S. Application Data

(60) Provisional application No. 61/514,565, filed on Aug. 3, 2011.

(51) Int. Cl.
*C12N 15/82* (2006.01)
(52) U.S. Cl.
CPC ................ *C12N 15/8213* (2013.01)

(58) Field of Classification Search
None
See application file for complete search history.

(56) References Cited

U.S. PATENT DOCUMENTS

| | | | | |
|---|---|---|---|---|
| 7,102,055 B1* | 9/2006 | Baszczynski | ............ | C12N 9/00 435/419 |
| 2005/0064474 A1* | 3/2005 | Urnov | ............... | C07K 14/43595 435/6.18 |
| 2006/0282911 A1* | 12/2006 | Bull | ......................... | A01H 1/02 800/266 |
| 2007/0015195 A1* | 1/2007 | Tao | ..................... | C12N 15/1051 435/6.13 |
| 2009/0133152 A1* | 5/2009 | Lyznik | ..................... | C12N 9/22 800/275 |

FOREIGN PATENT DOCUMENTS

| WO | WO-2007011733 A2 | 1/2007 |
|---|---|---|
| WO | WO-2009006297 A2 | 1/2009 |

OTHER PUBLICATIONS

International Search Report issued by the International Searching Authority dated Oct. 19, 2012 for application PCT/US2012/047202, filed Jul. 18, 2012 (Applicant—Pioneer Hi-Bred International, Inc. // Inventor—Cigan, et al.) (5 pages).
International Preliminary Report on Patentability and Written Opinion issued by the International Searching Authority dated Feb. 4, 2014 for application PCT/US2012/047202, filed Jul. 18, 2012 (Applicant—Pioneer Hi-Bred International, Inc. // Inventor—Cigan, et al.) (6 pages).

* cited by examiner

Primary Examiner — Matthew R Keogh
(74) Attorney, Agent, or Firm — Ballard Spahr LLP

(57) ABSTRACT

Compositions and methods are provided for the targeted integration of a polynucleotide sequence of interest into the genome of a plant or plant cell. The methods and compositions employ recognition sites for endonucleases and endonucleases in combination with site-specific recombination sites/recombinases to provide an effective system for establishing target sites within the genome of a plant, plant cell or seed. Once such target sites are established, a variety of methods can be employed to further modify the target sites such that they contain a variety of polynucleotides of interest.

33 Claims, 6 Drawing Sheets

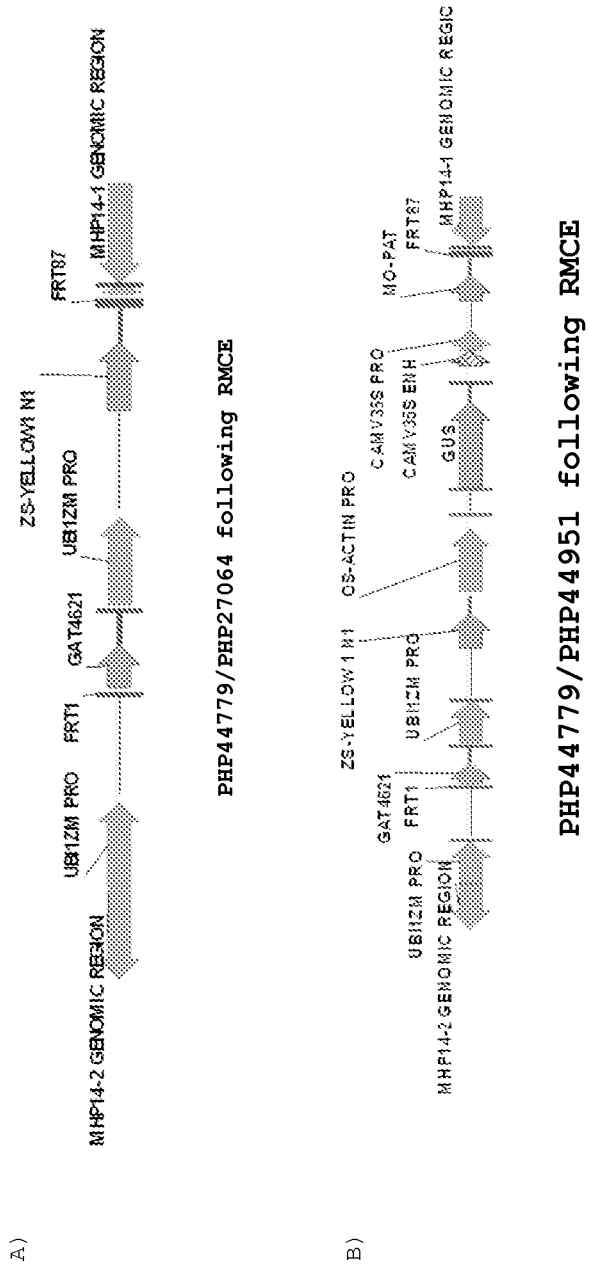

SEQUENCE LISTING

```
<160> NUMBER OF SEQ ID NOS: 36

<210> SEQ ID NO 1
<211> LENGTH: 22
<212> TYPE: DNA
<213> ORGANISM: Glycine max
<220> FEATURE:
<221> NAME/KEY: misc_feature
<222> LOCATION: (1)..(22)
<223> OTHER INFORMATION: TS21 recognition site of soybean

<400> SEQUENCE: 1
ggcactctcg tgtgtgatta aa                                            22

<210> SEQ ID NO 2
<211> LENGTH: 22
<212> TYPE: DNA
<213> ORGANISM: Glycine max
<220> FEATURE:
<221> NAME/KEY: misc_feature
<222> LOCATION: (1)..(22)
<223> OTHER INFORMATION: TS14 recognition site of soybean

<400> SEQUENCE: 2
cagacgtacg caagtagctt tg                                            22

<210> SEQ ID NO 3
<211> LENGTH: 22
<212> TYPE: DNA
<213> ORGANISM: Glycine max
<220> FEATURE:
<221> NAME/KEY: misc_feature
<222> LOCATION: (1)..(22)
<223> OTHER INFORMATION: TS30 recognition site

<400> SEQUENCE: 3
gagtcccacg caagagcata aa                                            22

<210> SEQ ID NO 4
<211> LENGTH: 22
<212> TYPE: DNA
<213> ORGANISM: Glycine max
<220> FEATURE:
<221> NAME/KEY: misc_feature
<222> LOCATION: (1)..(22)
<223> OTHER INFORMATION: TS5 recognition site

<400> SEQUENCE: 4
aagacttacg tgtgtactcg tg                                            22

<210> SEQ ID NO 5
<211> LENGTH: 22
<212> TYPE: DNA
```

```
<213> ORGANISM: Glycine max
<220> FEATURE:
<221> NAME/KEY: misc_feature
<222> LOCATION: (1)..(22)
<223> OTHER INFORMATION: TS7 recognition site

<400> SEQUENCE: 5
gacattgtcg tgagaaaaga ga                                              22

<210> SEQ ID NO 6
<211> LENGTH: 22
<212> TYPE: DNA
<213> ORGANISM: Glycine max
<220> FEATURE:
<221> NAME/KEY: misc_feature
<222> LOCATION: (1)..(22)
<223> OTHER INFORMATION: TS4 recognition site

<400> SEQUENCE: 6
aaatctgtct tgcgaaacgg ca                                              22

<210> SEQ ID NO 7
<211> LENGTH: 22
<212> TYPE: DNA
<213> ORGANISM: Glycine max
<220> FEATURE:
<221> NAME/KEY: misc_feature
<222> LOCATION: (1)..(22)
<223> OTHER INFORMATION: TS22 recognition site

<400> SEQUENCE: 7
tattctctca taaataaact tt                                              22

<210> SEQ ID NO 8
<211> LENGTH: 22
<212> TYPE: DNA
<213> ORGANISM: Glycine max
<220> FEATURE:
<221> NAME/KEY: misc_feature
<222> LOCATION: (1)..(22)
<223> OTHER INFORMATION: TS24 recognition site

<400> SEQUENCE: 8
ggaatggaca taagagaact gt                                              22

<210> SEQ ID NO 9
<211> LENGTH: 34
<212> TYPE: DNA
<213> ORGANISM: Artificial Sequence
<220> FEATURE:
<223> OTHER INFORMATION: FRT1 recombination site
<220> FEATURE:
<221> NAME/KEY: misc_feature
<222> LOCATION: (1)..(34)
<223> OTHER INFORMATION: FRT1 recombination site

<400> SEQUENCE: 9
gaagttccta ttctctagaa agtataggaa cttc                                 34

<210> SEQ ID NO 10
<211> LENGTH: 30
<212> TYPE: DNA
<213> ORGANISM: Artificial Sequence
<220> FEATURE:
<223> OTHER INFORMATION: FRT5 recombination site
<220> FEATURE:
<221> NAME/KEY: misc_feature
<222> LOCATION: (1)..(30)
<223> OTHER INFORMATION: FRT5 recombination site
```

```
<400> SEQUENCE: 10
agttcctatt cttcaaaagg tataggaact                                      30

<210> SEQ ID NO 11
<211> LENGTH: 30
<212> TYPE: DNA
<213> ORGANISM: Artificial Sequence
<220> FEATURE:
<223> OTHER INFORMATION: FRT6 recombination site
<220> FEATURE:
<221> NAME/KEY: misc_feature
<222> LOCATION: (1)..(30)
<223> OTHER INFORMATION: FRT6 recombination site

<400> SEQUENCE: 11
agttcctatt cttcaaaaag tataggaact                                      30

<210> SEQ ID NO 12
<211> LENGTH: 30
<212> TYPE: DNA
<213> ORGANISM: Artificial Sequence
<220> FEATURE:
<223> OTHER INFORMATION: FRT12 recombination site
<220> FEATURE:
<221> NAME/KEY: misc_feature
<222> LOCATION: (1)..(30)
<223> OTHER INFORMATION: FRT12 recombination site

<400> SEQUENCE: 12
agttcctata ctctatgtag aataggaact                                      30

<210> SEQ ID NO 13
<211> LENGTH: 30
<212> TYPE: DNA
<213> ORGANISM: Artificial Sequence
<220> FEATURE:
<223> OTHER INFORMATION: FRT87 recombination site
<220> FEATURE:
<221> NAME/KEY: misc_feature
<222> LOCATION: (1)..(30)
<223> OTHER INFORMATION: FRT87 recombination site

<400> SEQUENCE: 13
agttcctata ctttctggag aataggaact                                      30

<210> SEQ ID NO 14
<211> LENGTH: 18211
<212> TYPE: DNA
<213> ORGANISM: Artificial Sequence
<220> FEATURE:
<223> OTHER INFORMATION: PHP36070;

<400> SEQUENCE: 14
gtaccgagct cgtttaaacg ctcttcaact ggaagagcgg ttaccagagc tggtcacctt      60
tgtccaccaa gatggaactg gcgcgcctca ttaattaagt cagcggccgc tctagttgaa     120
gacacgttca tgtcttcatc gtaagaagac actcagtagt cttcggccag aatggccatc     180
tggattcagc aggcctagaa ggccatttaa atcctgagga tctggtcttc ctaaggaccc     240
gggatatcgg accgattaaa ctttaattcg gtccgataac ttcgtatagc atacattata     300
cgaagttata cctggtggcg aattcgccct tgctaacaag gcattgttgc ttgcatttgc     360 aattttttgct cgtacgtacg tacgtacgtc tacccggcgg ctgtacaaag tcttgcgatg     420
cttggaagaa agtagccttg tttctgactt ttttgagagg ccaatacttg tacagccacc     480
```

```
tcgctgttta taataactac tagatcgaaa ataccaagaa cggagaagtc aaggaaataa      540
atggaaacga gtaatgccaa ggaagaaata aaatggaaag gagtaaataa tgccaaggaa      600
gaaattgagt ggaagaggag gaggaggaga gacaaaagaa aatctaggtt taccaaaatg      660
ttgaagagaa agggctagat aatttcagcg gcaaattatt aactgggatg tgaactgacg      720
agggaaaatg gcttacagat cttttgcttt gcaaccagta agtacatatt tatgcatttt      780
gtgttaataa caactggatt tttgtcaatt aagcatgctc tctttagttt gttgttggat      840
tcaattgtta tataataata taatacatat agatcgagaa gtagtggttg ctaatataag      900
taggagtaca gtcattttag aaagtttgcc tcaagaaata taaggtttct ggggaaatta      960
ggctcatgaa atggagtcat atatatcgaa acgcataaca tgtcaaactg agatatattc     1020
ggttaaaatg cagctgaaga gacgaagtca gagagaaata aagggcaggga tgatatcatg     1080 caaaataaaa gcaatagctt tcaccccctt gttcaattga cttttataa ctaaaaaga       1140 aggaaataat tatgatatca tgcaaactat aagtgatgta tcatgaggcg caacgaagta     1200
acctatcctc ccaaaagatt tttctgacaa aattgtagct tcgaagagtg ccagataact     1260
cgtgagatcg agcaacaata aagcatgcat gaaatcagtt tcgatcaagc tggccaatga     1320
actgaagggg ggatcactta atgcaactcg tgatgatttc agatatatat gtatgtgtag     1380
acaagatcta tatagacatg tgaagtaccc gaccgaacca taaaggtaga ttatttaccc     1440
ctcgaattaa gttgagaacc tggctagcca gagagatcga gatcgatgga ttgaattgaa     1500
ttgaattgaa ttggatccag tgatgaccga gtggcctact gacctgctgc actgctggca     1560
gaacctctga tgcagtccac cggcggtgac gacgacgggc gccttggagt ggtgctcgca     1620
caccttgtgg cgacggtggt atctcttggc gctggagagg tcggccttgc agccctcggc     1680
ctggcagcgc ggcgggtggt ggccgtacgt gtagcctcct ctgggcggga agtaggtgcg     1740
gtagccgagg ttgaggccga gctgcgtggc ggcgaagctg gccatgttct cctcggcgga     1800
gctgacgagg gtggggaagt agtactcggg cgcggcctgc gccgccgccg ccggcgggta     1860
gtaggacgac gaggtctggt ggaaggtggt cccgggcgcg gagactaagt ggctgtaggg     1920
gttgccgccg gcggcggcga ggtagtgcga ggcggcggaa ggaggagggt agaagtggag     1980
gatgtcgtgg gggctgtggc cgccggcgaa ggtggtgtgg tggtgggcgg cggcggcgtt     2040 ggacggggc aggagggcca gcgagttggc ctcgaggttg tagcccagca gctgatgatg      2100
ctccctgtgg atgctgctct cctgctgctg ctccatggtt gggagcaggg aaggggggcgg    2160 agcggccgcg ttgacggca cgacgtaggg ggggaactcg tcgcggccgt tggcggcagc      2220
cgataggttc atcatcttcc cacgccccgg ccggcacgtt gacacgatat ctcgatcgat     2280
cggtcggccc ggccgcccga tctgtgcagg tgcaggtcgc gcgggcgggc gcggctagct     2340
gggagcctgg gaggggagga ggggccggag ggagcaggag caggagtgcc cgcgcgcgca     2400
cacacgagca cacggaaatg gatgcgtagg ggacggaggg gaggacgcg gcaaggacag      2460 cgcttagcgg agagctcggt ggagatcgat cgctcagtcg gtcgcaggtg gacgagcgac     2520
agacagagct aatacggcgg tgttggccgg ccgggccatg gtgtgggtga tggcgatgac     2580
acagatatat gcgcgggcgg gcgccagcta gtagccgggc agctagcgcg cgcccttctc     2640
ggccggccgg atctctttg ctgcggagag ggagagggcg agagcgaggg ccgagagcgc      2700
gagtactttt ggtctagggt tccatggaac gagtggtggt ggagtgagtt ttgggctata     2760
tctaagagca acgcccgcag ctcagctagc aacaaaccgg gcgctggcac tgacagggcc     2820
ggccagtaga gagagagaga gagatcttta attggagttg gtgagtggtg atagcagccg     2880
```

```
cagctgctgc tgctgctgct gctgcttctt tgtggttggt ttggttcgcc ctccattttt    2940
cctcacccgg gagtccgtat gctatctgct atatgctagg ctggctgtgg gtgtctatgt    3000
atgtatcctc ctcctccgtt gaaacaacgt agcgtacgac actgctgcat gtgtggcctt    3060
gaagatatga gtatctatgc atgatgcgga tgctgtacat gtgcattgca tcgctcttct    3120
ctctccctgc ggtggtgtgt acgagacggt gggtacgtac gctaacgcta gcagctgcct    3180
cccgcgtgac gccaggggca gcccggccgg acgcggtgtt tcgttccatg accatgaggc    3240
gtgatctcag tcatggccca actacgccag gggcttgcat tgcccgcgcg cgtagacttt    3300
gcacctgcgc atgtatgtat gtacatcctg cagcgcacag cagactgagc tgtattcccg    3360
cgcaaatgag tagcagcgca cgtatatata cgcgtacgcg tacaagggcg aattcgccgc    3420
tagcctgcag tgcagcgtga cccggtcgtg cccctctcta gagataatga gcattgcatg    3480
tctaagttat aaaaaattac cacatatttt ttttgtcaca cttgtttgaa gtgcagttta    3540
tctatcttta tacatatatt taaactttac tctacgaata atataatcta tagtactaca    3600
ataatatcag tgttttagag aatcatataa atgaacagtt agacatggtc taaaggacaa    3660
ttgagtattt tgacaacagg actctacagt tttatctttt tagtgtgcat gtgttctcct    3720
ttttttttgc aaatagcttc acctatataa tacttcatcc attttattag tacatccatt    3780
tagggtttag ggtaatggt ttttatagac taattttttt agtacatcta ttttattcta    3840
ttttagcctc taaattaaga aaactaaaac tctatttag tttttttatt taataattta    3900
gatataaaat agaataaaat aaagtgacta aaaattaaac aaatacccct taagaaatta    3960
aaaaaactaa ggaaacattt tcttgttc gagtagataa tgccagcctg ttaaacgccg    4020
tcgacgagtc taacggacac caaccagcga accagcagcg tcgcgtcggg ccaagcgaag    4080
cagacggcac ggcatctctg tcgctgcctc tggacccctc tcgagagttc cgctccaccg    4140
ttggacttgc tccgctgtcg gcatccagaa attgcgtggc ggagcggcag acgtgagccg    4200
gcacggcagg cggcctcctc ctcctctcac ggcaccggca gctacggggg attcctttcc    4260
caccgctcct tcgctttccc ttcctcgccc gccgtaataa atagacaccc cctccacacc    4320
ctctttcccc aacctcgtgt tgttcggagc gcacacacac acaaccagat ctcccccaaa    4380
tccacccgtc ggcacctccg cttcaaggta cgccgctcgt cctcccccc ccccctctct    4440 accttctcta gatcggcgtt ccggtccatg catggttagg gcccggtagt tctacttctg    4500
ttcatgtttg tgttagatcc gtgtttgtgt tagatccgtg ctgctagcgt tcgtacacgg    4560
atgcgacctg tacgtcagac acgttctgat tgctaacttg ccagtgtttc tctttgggga    4620
atcctgggat ggctctagcc gttccgcaga cgggatcgat ttcatgattt tttttgtttc    4680
gttgcatagg gtttggtttg cccttttcct ttatttcaat atatgccgtg cacttgtttg    4740
tcgggtcatc ttttcatgct tttttttgtc ttggttgtga tgatgtggtc tggttgggcg    4800
gtcgttctag atcggagtag aattctgttt caaactacct ggtggattta ttaatttggg    4860
atctgtatgt gtgtgccata catattcata gttacgaatt gaagatgatg gatggaaata    4920
tcgatctagg ataggtatac atgttgatgc gggttttact gatgcatata cagagatgct    4980
ttttgttcgc ttggttgtga tgatgtgtg tggttgggcg gtcgttcatt cgttctagat    5040
cggagtagaa tactgtttca aactacctgg tgtatttatt aattttggaa ctgtatgtgt    5100
gtgtcataca tcttcatagt tacgagttta agatggatgg aaatatcgat ctaggatagg    5160
tatacatgtt gatgtgggtt ttactgatgc atatacatga tggcatatgc agcatctatt    5220
```

```
catatgctct aaccttgagt acctatctat tataataaac aagtatgttt tataattatt   5280
ttgatcttga tatacttgga tgatggcata tgcagcagct atatgtggat tttttagcc    5340
ctgccttcat acgctattta tttgcttggt actgtttctt ttgtcgatgc tcaccctgtt   5400
gtttggtgtt acttctgcag gtcgactcta gaggatcaat tcgctagcga agttcctatt   5460
ccgaagttcc tattctctag aaagtatagg aacttcagat ccaccgggat ccacacgaca   5520
ccatgtcccc cgagcgccgc ccgtcgaga tccgccggc caccgccgcc gacatggccg     5580
ccgtgtgcga catcgtgaac cactacatcg agacctccac cgtgaacttc cgcaccgagc   5640
cgcagacccc gcaggagtgg atcgacgacc tggagcgcct ccaggaccgc tacccgtggc   5700
tcgtggccga ggtggagggc gtggtggccg gcatcgccta cgccggcccg tggaaggccc   5760
gcaacgccta cgactggacc gtggagtcca ccgtgtacgt gtcccaccgc caccagcgcc   5820
tcggcctcgg ctccacccte tacacccacc tcctcaagag catggaggcc cagggcttca   5880
agtccgtggt ggccgtgatc ggcctcccga acgaccgtc cgtgcgcctc cacgaggccc    5940
tcggctacac cgcccgcggc accctccgcg ccgccggcta caagcacggc ggctggcacg   6000
acgtcggctt ctggcagcgc gacttcgagc tgccggcccc gccgcgcccg gtgcgcccgg   6060
tgacgcagat ctgagtcgaa acctagactt gtccatcttc tggattggcc aacttaatta   6120
atgtatgaaa taaaggatg cacacatagt gacatgctaa tcactataat gtgggcatca    6180
aagttgtgtg ttatgtgtaa ttactagtta tctgaataaa agagaaagag atcatccata   6240
tttcttatcc taaatgaatg tcacgtgtct ttataattct ttgatgaacc agatgcattt   6300
cattaaccaa atccatatac atataaatat taatcatata taattaatat caattgggtt   6360
agcaaaacaa atctagtcta ggtgtgtttt gcgaatgcgg ccctagcgta tacgaagttc   6420
ctattccgaa gttcctattc tccagaaagt ataggaactt ctgtacacct gagctgattc   6480
cgatgacttc gtaggttcct agctcaagcc gctcgtgtcc aagcgtcact tacgattagc   6540
taatgattac ggcatctagg accgactagc taactaacta gtacaattcg cccttgtgtg   6600
aggtatatat atcctccgcc ggggcacgta cggtacaatt cccagcaggt gcgtaaatcg   6660
ttacagtata ttatttccgc agccgatcaa aagaagtttg cgcgtcgtca cggcactgac   6720
ttctatttag ggcggccaga gtaggctagc ctgctggacc ctctgtgtcc cgtctatctc   6780
attcattcac tcatcagctg gtgctctatt tttctctccc taattaagct ggtgaaatt    6840
tcgtgctttt cgtttgcacc gtgtgccatt ggatcggatc tgatatatat gcgcgcggcc   6900
gtccgagacc ttattactcg tcaccttctt caacctaacc ccccccccc ccccttaat     6960
ttgctagccc taactggcac catatatcat tttgcccaca cataataaac gactcctttg   7020
ccaactgcac cagtcacttg gcaaacgact aattacactc ggcaaaaggt tttgtcgtgt   7080
gccacactcg tcaaagagct cttggtgaaa caaacgccgg taacgatctc tttgctgagc   7140
gccaacatac tcggcataga aggtacatta acggcgggca tcatggtgat gggaaactac   7200
cttttttgcct agtgtattgt tttgccgagg agggtggtat tcggcaaatc atatatttgc   7260
cgagtgctcg ctctcagcaa acgtgtgagc actcggcaaa gagcgtgtct ccagttgtgt   7320
tgtcattatc tattttttt aacctacggc atgccaccac caaaggtttt aattgtcagg    7380
aactttctgt attgtagttt taattatata agttgttctc catcaggact tcgaggtcat   7440
gttgtatgat caatgaaaga atctcaagac ggactcaaag agtggactct cgtcatggat   7500
taaaggtgta tttactgcaa ggaaaagtgc aggcaatatt cagtactcga gagaatctac   7560
attttactct tagctcatca cctatgtggg ataggtgaag gcgtgaagca ctccgagtct   7620
```

```
tcttggctat tcaaagtttc cttttcactt tgctttcctt ttggtgtatt atagcacaca   7680
gttttctatg ggtcaagggc gaattgtaga attaattcat tccgattaat cgtggcctct   7740
tgctcttcag gatgaagagc tatgtttaaa cgtgcaagcg ctactagaca attcagtaca   7800
ttaaaaacgt ccgcaatgtg ttattaagtt gtctaagcgt caatttgttt acaccacaat   7860
atatcctgcc accagccagc caacagctcc ccgaccggca gctcggcaca aaatcaccac   7920
tcgatacagg cagcccatca gtccgggacg gcgtcagcgg gagagccgtt gtaaggcggc   7980
agactttgct catgttaccg atgctattcg gaagaacggc aactaagctg ccgggtttga   8040
aacacggatg atctcgcgga gggtagcatg ttgattgtaa cgatgacaga gcgttgctgc   8100
ctgtgatcaa atatcatctc cctcgcagag atccgaatta tcagccttct tattcatttc   8160
tcgcttaacc gtgacaggct gtcgatcttg agaactatgc cgacataata ggaaatcgct   8220
ggataaagcc gctgaggaag ctgagtggcg ctatttcttt agaagtgaac gttgacgatc   8280
gtcgaccgta ccccgatgaa ttaattcgga cgtacgttct gaacacagct ggatacttac   8340
ttgggcgatt gtcatacatg acatcaacaa tgtacccgtt tgtgtaaccg tctcttggag   8400
gttcgtatga cactagtggt tcccctcagc ttgcgactag atgttgaggc ctaacatttt   8460
attagagagc aggctagttg cttagataca tgatcttcag gccgttatct gtcagggcaa   8520
gcgaaaattg gccatttatg acgaccaatg ccccgcagaa gctcccatct ttgccgccat   8580
agacgccgcg cccccctttt ggggtgtaga acatccttt tgccagatgtg gaaagaagt    8640 tcgttgtccc attgttggca atgacgtagt agccggcgaa agtgcgagac ccatttgcgc   8700
tatatataag cctacgattt ccgttgcgac tattgtcgta attggatgaa ctattatcgt   8760
agttgctctc agagttgtcg taatttgatg gactattgtc gtaattgctt atggagttgt   8820
cgtagttgct tggagaaatg tcgtagttgg atggggagta gtcataggga agacgagctt   8880
catccactaa aacaattggc aggtcagcaa gtgcctgccc cgatgccatc gcaagtacga   8940
ggcttagaac caccttcaac agatcgcgca tagtcttccc cagctctcta acgcttgagt   9000
taagccgcgc cgcgaagcgg cgtcggcttg aacgaattgt tagacattat ttgccgacta   9060
ccttggtgat ctcgcctttc acgtagtgaa caaattcttc caactgatct gcgcgcgagg   9120
ccaagcgatc ttcttgtcca agataagcct gcctagcttc aagtatgacg ggctgatact   9180
gggccggcag gcgctccatt gcccagtcgg cagcgacatc cttcggcgcg attttgccgg   9240
ttactgcgct gtaccaaatg cgggacaacg taagcactac atttcgctca tcgccagccc   9300
agtcgggcgg cgagttccat agcgttaagg tttcatttag cgcctcaaat agatcctgtt   9360
caggaaccgg atcaaagagt tcctccgccg ctggacctac caaggcaacg ctatgttctc   9420
ttgcttttgt cagcaagata gccagatcaa tgtcgatcgt ggctggctcg aagatacctg   9480
caagaatgtc attgcgctgc cattctccaa attgcagttc gcgcttagct ggataacgcc   9540
acggaatgat gtcgtcgtgc acaacaatgg tgacttctac agcgcggaga atctcgctct   9600
ctccagggga agccgaagtt ccaaaaggt cgttgatcaa agctcgccgc gttgtttcat    9660
caagccttac agtcaccgta accagcaaat caatatcact gtgtggcttc aggccgccat   9720
ccactgcgga gccgtacaaa tgtacggcca gcaacgtcgg ttcagatgg cgctcgatga    9780 cgccaactac ctctgatagt tgagtcgata cttcggcgat caccgcttcc ctcatgatgt   9840
ttaactcctg aattaagccg cgccgcgaag cggtgtcggc ttgaatgaat tgttaggcgt   9900
catcctgtgc tcccgagaac cagtaccagt acatcgctgt ttcgttcgag acttgaggtc   9960
```

```
tagttttata cgtgaacagg tcaatgccgc cgagagtaaa gccacatttt gcgtacaaat   10020
tgcaggcagg tacattgttc gtttgtgtct ctaatcgtat gccaaggagc tgtctgctta   10080
gtgcccactt tttcgcaaat tcgatgagac tgtgcgcgac tcctttgcct cggtgcgtgt   10140
gcgacacaac aatgtgttcg atagaggcta gatcgttcca tgttgagttg agttcaatct   10200
tcccgacaag ctcttggtcg atgaatgcgc catagcaagc agagtcttca tcagagtcat   10260
catccgagat gtaatccttc cggtagggc tcacacttct ggtagatagt tcaaagcctt    10320
ggtcggatag gtgcacatcg aacacttcac gaacaatgaa atggttctca gcatccaatg   10380
tttccgccac ctgctcaggg atcaccgaaa tcttcatatg acgcctaacg cctggcacag   10440
cggatcgcaa acctggcgcg gcttttggca caaaaggcgt gacaggtttg cgaatccgtt   10500
gctgccactt gttaacccctt ttgccagatt tggtaactat aatttatgtt agaggcgaag  10560
tcttgggtaa aaactggcct aaaattgctg gggatttcag gaaagtaaac atcaccttcc   10620
ggctcgatgt ctattgtaga tatatgtagt gtatctactt gatcggggga tctgctgcct   10680
cgcgcgtttc ggtgatgacg gtgaaaacct ctgcacacatg cagctcccgg agacggtcac  10740
agcttgtctg taagcggatg ccgggagcag acaagcccgt cagggcgcgt cagcgggtgt   10800
tggcgggtgt cggggcgcag ccatgaccca gtcacgtagc gatagcggag tgtatactgg   10860
cttaactatg cggcatcaga gcagattgta ctgagagtgc accatatgcg gtgtgaaata   10920
ccgcacagat gcgtaaggag aaaataccgc atcaggcgct cttccgcttc ctcgctcact   10980
gactcgctgc gctcggtcgt tcggctgcgg cgagcggtat cagctcactc aaaggcggta   11040
atacggttat ccacagaatc aggggataac gcaggaaaga acatgtgagc aaaaggccag   11100
caaaaggcca ggaaccgtaa aaaggccgcg ttgctggcgt ttttccatag gctccgcccc   11160
cctgacgagc atcacaaaaa tcgacgctca agtcagaggt ggcgaaaccc gacaggacta   11220
taaagatacc aggcgtttcc ccctggaagc tccctcgtgc gctctcctgt tccgaccctg   11280
ccgcttaccg gatacctgtc cgcctttctc ccttcgggaa gcgtggcgct ttctcatagc   11340
tcacgctgta ggtatctcag ttcggtgtag gtcgttcgct ccaagctggg ctgtgtgcac   11400
gaaccccccg ttcagcccga ccgctgcgcc ttatccggta actatcgtct tgagtccaac   11460
ccggtaagac acgacttatc gccactggca gcagccactg gtaacaggat tagcagagcg   11520
aggtatgtag gcggtgctac agagttcttg aagtggtggc ctaactacgg ctacactaga   11580
aggacagtat ttggtatctg cgctctgctg aagccagtta ccttcggaaa aagagttggt   11640
agctcttgat ccggcaaaca aaccaccgct ggtagcggtg gtttttttgt ttgcaagcag   11700
cagattacgc gcagaaaaaa aggatctcaa gaagatcctt tgatcttttc tacggggtct   11760
gacgctcagt ggaacgaaaa ctcacgttaa gggattttgg tcatgagatt atcaaaaagg   11820
atcttcacct agatcctttt aaattaaaaa tgaagtttta atcaatcta aagtatatat     11880
gagtaaactt ggtctgacag ttaccaatgc ttaatcagtg aggcacctat ctcagcgatc   11940
tgtctatttc gttcatccat agttgcctga ctccccgtcg tgtagataac tacgatacgg   12000
gagggcttac catctggccc cagtgctgca atgataccgc gagacccacg ctcaccggct   12060
ccagatttat cagcaataaa ccagccagcc ggaagggccg agcgcagaag tggtcctgca   12120
actttatccg cctccatcca gtctattaat tgttgccggg aagctagagt aagtagttcg   12180
ccagttaata gtttgcgcaa cgttgttgcc attgctgcag ggggggggg gggggggac     12240
ttccattgtt cattccacgg acaaaaacag agaaaggaaa cgacagaggc caaaaagcct   12300
cgctttcagc acctgtcgtt tcctttcttt tcagagggta ttttaaataa aaacattaag   12360
```

```
ttatgacgaa gaagaacgga aacgccttaa accggaaaat tttcataaat agcgaaaacc   12420
cgcgaggtcg ccgccccgta acctgtcgga tcaccggaaa ggacccgtaa agtgataatg   12480
attatcatct acatatcaca acgtgcgtgg aggccatcaa accacgtcaa ataatcaatt   12540
atgacgcagg tatcgtatta attgatctgc atcaacttaa cgtaaaaaca acttcagaca   12600
atacaaatca gcgacactga atacggggca acctcatgtc cccccccccc ccccccctgc   12660
aggcatcgtg gtgtcacgct cgtcgtttgg tatggcttca ttcagctccg gttcccaacg   12720
atcaaggcga gttacatgat cccccatgtt gtgcaaaaaa gcggttagct ccttcggtcc   12780
tccgatcgtt gtcagaagta agttggccgc agtgttatca ctcatggtta tggcagcact   12840
gcataattct cttactgtca tgccatccgt aagatgcttt tctgtgactg gtgagtactc   12900
aaccaagtca ttctgagaat agtgtatgcg gcgaccgagt tgctcttgcc cggcgtcaac   12960
acgggataat accgcgccac atagcagaac tttaaaagtg ctcatcattg gaaaacgttc   13020
ttcggggcga aaactctcaa ggatcttacc gctgttgaga tccagttcga tgtaacccac   13080
tcgtgcaccc aactgatctt cagcatcttt tactttcacc agcgtttctg ggtgagcaaa   13140
aacaggaagg caaaatgccg caaaaaaggg aataagggcg acacggaaat gttgaatact   13200
catactcttc cttttttcaat attattgaag catttatcag ggttattgtc tcatgagcgg   13260
atacatattt gaatgtattt agaaaaataa acaaataggg gttccgcgca catttccccg   13320
aaaagtgcca cctgacgtct aagaaaccat tattatcatg acattaacct ataaaaatag   13380
gcgtatcacg aggcccttc gtcttcaaga attggtcgac gatcttgctg cgttcggata   13440
ttttcgtgga gttcccgcca cagacccgga ttgaaggcga gatccagcaa ctcgcgccag   13500
atcatcctgt gacggaactt tggcgcgtga tgactggcca ggacgtcggc cgaaagagcg   13560
acaagcagat cacgcttttc gacagcgtcg gatttgcgat cgaggatttt tcggcgctgc   13620
gctacgtccg cgaccgcgtt gagggatcaa gccacagcag cccactcgac cttctagccg   13680
acccagacga gccaagggat cttttttggaa tgctgctccg tcgtcaggct ttccgacgtt   13740
tgggtggttg aacagaagtc attatcgtac ggaatgccaa gcactcccga ggggaacccct   13800 gtggttggca tgcacataca aatggacgaa cggataaacc ttttcacgcc cttttaaata   13860
tccgttattc taataaacgc tcttttctct taggtttacc cgccaatata tcctgtcaaa   13920
cactgatagt ttaaactgaa ggcgggaaac gacaatctga tcatgagcgg agaattaagg   13980
gagtcacgtt atgaccccccg ccgatgacgc gggacaagcc gttttacgtt tggaactgac   14040
agaaccgcaa cgttgaagga gccactcagc aagctggtac gattgtaata cgactcacta   14100
tagggcgaat tgagcgctgt ttaaacgctc ttcaactgga agagcggtta ctaccggctg   14160
gatggcgggg ccttgatcgt gcaccgccgg cgtccggact aactaactag tcgagctagt   14220
taccctatga ggtgacatga agcgctcacg gttactatga cggttagctt cacgactgtt   14280
ggtggcagta gcgtacgact tagctatagt tccggactta cccttaagat aacttcgtat   14340
agcatacatt atacgaagtt atgggcccac cggtggtacc tggcgaaagg gggatgtgct   14400
gcaaggcgat taagttgggt aacgccaggg ttttcccagt cacgacgttg taaaacgacg   14460
gccagtgaat tgtaatacga ctcactatag ggcgaattgg gttacccgga ccgaagcttg   14520
catgcctgca gtgcagcgtg acccggtcgt gcccctctct agagataatg agcattgcat   14580
gtctaagtta taaaaaatta ccacatattt tttttgtcac acttgtttga agtgcagttt   14640
atctatcttt atacatatat ttaaacttta ctctacgaat aatataatct atagtactac   14700
```

```
aataatatca gtgttttaga gaatcatata aatgaacagt tagacatggt ctaaaggaca    14760
attgagtatt ttgacaacag gactctacag ttttatcttt ttagtgtgca tgtgttctcc    14820 ttttttttg  caaatagctt cacctatata atacttcatc cattttatta gtacatccat    14880
ttagggttta gggttaatgg tttttataga ctaattttt  tagtacatct attttattct    14940 atttttagcct ctaaattaag aaaactaaaa ctctatttta gttttttat  ttaataattt    15000 agatataaaa tagaataaaa taaagtgact aaaaattaaa caaatacccct ttaagaaatt    15060 aaaaaaacta aggaaacatt tttcttgttt cgagtagata atgccagcct gttaaacgcc    15120
gtcgacgagt ctaacggaca ccaaccagcg aaccagcagc gtcgcgtcgg gccaagcgaa    15180
gcagacggca cggcatctct gtcgctgcct ctggacccct ctcgagagtt ccgctccacc    15240
gttggacttg ctccgctgtc ggcatccaga aattgcgtgg cggagcggca gacgtgagcc    15300
ggcacggcag gcggcctcct cctcctctca cggcaccggc agctacgggg gattcctttc    15360
ccaccgctcc ttcgctttcc cttcctcgcc cgccgtaata aatagacacc ccctccacac    15420
cctcttcccc caacctcgtg ttgttcggag cgcacacaca cacaaccaga tctcccccaa    15480
atccacccgt cggcacctcc gcttcaaggt acgccgctcg tcctcccccc cccccctctc    15540
taccttctct agatcggcgt tccggtccat gcatggttag ggcccggtag ttctacttct    15600
gttcatgttt gtgttagatc cgtgtttgtg ttagatccgt gctgctagcg ttcgtacacg    15660
gatgcgacct gtacgtcaga cacgttctga ttgctaactt gccagtgttt ctctttgggg    15720
aatcctggga tggctctagc cgttccgcag acgggatcga tttcatgatt tttttgttt    15780 cgttgcatag ggtttggttt gccctttcc  tttatttcaa tatatgccgt gcacttgttt    15840
gtcgggtcat cttttcatgc tttttttgt  cttggttgtg atgatgtggt ctggttgggc    15900
ggtcgttcta gatcggagta gaattctgtt tcaaactacc tggtggattt attaattttg    15960
gatctgtatg tgtgtgccat acatattcat agttacgaat tgaagatgat ggatggaaat    16020
atcgatctag gataggtata catgttgatg cgggttttac tgatgcatat acagagatgc    16080 ttttgttcg  cttggttgtg atgatgtggt gtggttgggc ggtcgttcat tcgttctaga    16140
tcggagtaga atactgtttc aaactacctg gtgtatttat taattttgga actgtatgtg    16200
tgtgtcatac atcttcatag ttacgagttt aagatggatg gaaatatcga tctaggatag    16260
gtatacatgt tgatgtgggt tttactgatg catatacatg atggcatatg cagcatctat    16320
tcatatgctc taaccttgag tacctatcta ttataataaa caagtatgtt ttataattat    16380
tttgatcttg atatacttgg atgatggcat atgcagcagc tatatgtgga tttttttagc    16440
cctgccttca tacgctattt atttgcttgg tactgtttct tttgtcgatg ctcaccctgt    16500
tgtttggtgt tacttctgca ggtcgactct agaggatcca tggccccgaa gaagaagcgc    16560
aaggtgatca tgaacaccaa gtacaacaag gagttcctgc tctacctggc cggcttcgtg    16620
gacggcgacg gctccatcaa ggcgcagatc aagccgaacc agtcctgcaa gttcaagcac    16680
cagctctccc tgaccttcca ggtgacccag aagacgcaga ggcgctggtt cctcgacaag    16740
ctggtcgacg agatcggggt gggctacgtc tacgaccgcg ggtcggtgtc cgactacgag    16800
ctctcccaga tcaagcccct gcacaacttc ctcacccagc tccagccgtt cctcaagctg    16860
aagcagaagc aggcgaacct cgtcctgaag atcatcgagc agctccccct ggccaaggag    16920 tccccgaca  agttcctgga ggtgtgcacg tgggtcgacc agatcgcggc cctcaacgac    16980
agcaagaccc gcaagacgac ctcggagacg gtgcgggcgg tcctggactc cctcccagga    17040
tccgtgggag gtctatcgcc atctcaggca tccagcgccg catcctcggc ttcctcaagc    17100
```

```
ccgggttcag ggatctccga agcactcaga gctggagcaa ctaagtccaa ggaattcctg    17160
ctctacctgg ccggcttcgt ggacggcgac ggctccatca tcgcgtccat caagccgcgc    17220
cagtgctaca agttcaagca cgagctccgc ctggagttca ccgtgaccca agaagacgcag   17280 aggcgctggt tcctcgacaa gctggtcgac gagatcgggg tgggctacgt ctacgaccgc    17340
gggtcggtgt ccgactaccg cctctcccag atcaagcccc tgcacaactt cctcacccag    17400
ctccagccgt tcctcaagct gaagcagaag caggcgaacc tcgtcctgaa gatcatcgag    17460
cagctcccct cggccaagga gtccccggac aagttcctgg aggtgtgcac gtgggtcgac    17520
cagatcgcgg ccctcaacga cagcaagacc cgcaagacga cctcggagac ggtgcgggcg    17580
gtcctggact ccctcagcga agaagaagaa tcgtccccct gaggtaccac atggttaacc    17640
tagacttgtc catcttctgg attggccaac ttaattaatg tatgaaataa aaggatgcac    17700
acatagtgac atgctaatca ctataatgtg ggcatcaaag ttgtgtgtta tgtgtaatta    17760
ctagttatct gaataaaaga gaaagagatc atccatattt cttatcctaa atgaatgtca    17820
cgtgtcttta taattctttg atgaaccaga tgcatttcat taaccaaatc catatacata    17880
taaatattaa tcatatataa ttaatatcaa ttgggttagc aaaacaaatc tagtctaggt    17940
gtgttttgcg aatgcggccg ccaccgcggt ggagctcgaa ttccggtccg ggtcacccag    18000
cttgagtatt ctatagtgtc acctaaatag cttggcgtaa tcatggtcat agctgtttcc    18060
tgtgtgaaat tgttatccgc tcacaattcc acacaacata cgagccggaa gcataaagtg    18120
taaagcctgg ggtgcctaat gagtgagcta actcacatta attgcgttgc gctcactgcc    18180
cgctttccag tcgggaaacc tgtcgtgcca g                                  18211

<210> SEQ ID NO 15
<211> LENGTH: 1053
<212> TYPE: DNA
<213> ORGANISM: Artificial sequence
<220> FEATURE:
<223> OTHER INFORMATION: nucleotide sequence of the LIG3-4 meganuclease

<400> SEQUENCE: 15
atgaacacca agtacaacaa ggagttcctg ctctacctgg ccggcttcgt ggacggcgac      60
ggctccatca aggcgcagat caagccgaac cagtcctgca agttcaagca ccagctctcc     120
ctgaccttcc aggtgaccca agaagacgcag aggcgctggt tcctcgacaa gctggtcgac    180
gagatcgggg tgggctacgt ctacgaccgc gggtcggtgt ccgactacga gctctcccag    240
atcaagcccc tgcacaactt cctcacccag ctccagccgt tcctcaagct gaagcagaag    300
caggcgaacc tcgtcctgaa gatcatcgag cagctcccct cggccaagga gtccccggac    360
aagttcctgg aggtgtgcac gtgggtcgac cagatcgcgg ccctcaacga cagcaagacc    420
cgcaagacga cctcggagac ggtgcgggcg gtcctggact ccctcccagg atccgtggga    480
ggtctatcgc catctcaggc atccagcgcc gcatcctcgg cttcctcaag cccgggttca    540
gggatctccg aagcactcag agctggagca actaagtcca aggaattcct gctctacctg    600
gccggcttcg tggacggcga cggctccatc atcgcgtcca tcaagccgcg ccagtgctac    660
aagttcaagc acgagctccg cctggagttc accgtgaccc agaagacgca gaggcgctgg    720
ttcctcgaca agctggtcga cgagatcggg gtgggctacg tctacgaccg cgggtcggtg    780
tccgactacc gcctctccca gatcaagccc ctgcacaact tcctcaccca gctccagccg    840
ttcctcaagc tgaagcagaa gcaggcgaac ctcgtcctga gatcatcga gcagctcccc    900
```

```
tcggccaagg agtccccgga caagttcctg gaggtgtgca cgtgggtcga ccagatcgcg      960
gccctcaacg acagcaagac ccgcaagacg acctcggaga cggtgcgggc ggtcctggac     1020
tccctcagcg agaagaagaa gtcgtccccc tga                                  1053
```

<210> SEQ ID NO 16
<211> LENGTH: 22
<212> TYPE: DNA
<213> ORGANISM: Zea mays

<400> SEQUENCE: 16

```
atatacctca cacgtacgcg ta                                                22
```

<210> SEQ ID NO 17
<211> LENGTH: 1097
<212> TYPE: DNA
<213> ORGANISM: Zea mays
<220> FEATURE:
<221> NAME/KEY: misc_feature
<222> LOCATION: (1)..(1097)
<223> OTHER INFORMATION: HR1 of LIG3-4

<400> SEQUENCE: 17

```
gtgtgaggta tatatatcct ccgccggggc acgtacggta caattcccag caggtgcgta       60
aatcgttaca gtatattatt tccgcagccg atcaaaagaa gtttgcgcgt cgtcacggca      120
ctgacttcta tttagggcgg ccagagtagg ctagcctgct ggaccctctg tgtcccgtct      180
atctcattca ttcactcatc agctggtgct ctattttttct ctccctaatt aagctggtgg     240
aaatttcgtg ctttttcgttt gcaccgtgtg ccattggatc ggatctgata tatatgcgcg     300
cggccgtccg agaccttatt actcgtcacc ttcttcaacc taacccccccc cccccccct     360 ttaatttgct agccctaact ggcaccatat atcattttgc ccacacataa taaacgactc      420
ctttgccaac tgcaccagtc acttggcaaa cgactaatta cactcggcaa aaggttttgt     480
cgtgtgccac actcgtcaaa gagctcttgg tgaaacaaac gccggtaacg atctctttgc      540
tgagcgccaa catactcggc atagaaggta cattaacggc gggcatcatg gtgatgggaa      600
actacctttt tgcctagtgt attgttttgc cgaggagggt ggtattcggc aaatcatata      660
tttgccgagt gctcgctctc agcaaacgtg tgagcactcg gcaaagagcg tgtctccagt      720
tgtgttgtca ttatctattt ttttttaacct acggcatgcc accaccaaag gttttaattg     780
tcaggaactt tctgtattgt agtttttaatt atataagttg ttctccatca ggacttcgag     840
gtcatgttgt atgatcaatg gaagaatctc aagacggact caaagagtgg actctcgtca      900
tggattaaag gtgtatttac tgcaaggaaa agtgcaggca atattcagta ctcgagagaa      960
tctacatttt actcttagct catcacctat gtgggatagg tgaaggcgtg aagcactccg     1020
agtcttcttg gctattcaaa gtttccttttt cactttgctt tccttttggt gtattatagc     1080
acacagtttt ctatggg                                                   1097
```

<210> SEQ ID NO 18
<211> LENGTH: 3072
<212> TYPE: DNA
<213> ORGANISM: Zea mays
<220> FEATURE:
<221> NAME/KEY: misc_feature
<222> LOCATION: (1)..(3072)
<220> FEATURE:
<221> NAME/KEY: misc_feature
<222> LOCATION: (1)..(3072)
<223> OTHER INFORMATION: HR2 of LIG3-4

<400> SEQUENCE: 18

```
gctaacaagg cattgttgct tgcatttgca attttttgctc gtacgtacgt acgtacgtct      60
acccggcggc tgtacaaagt cttgcgatgc ttggaagaaa gtagccttgt ttctgacttt     120
tttgagaggc caatacttgt acagccacct cgctgtttat aataactact agatcgaaaa     180
taccaagaac ggagaagtca aggaaataaa tggaaacgag taatgccaag gaagaaataa     240
aatgaaagg agtaaataat gccaaggaag aaattgagtg aagaggagg aggaggagag       300
acaaaagaaa atctaggttt accaaaatgt gaagagaaa gggctagata atttcagcgg      360
caaattatta actgggatgt gaactgacga gggaaaatgg cttacagatc ttttgctttg     420
caaccagtaa gtacatattt atgcatttg tgttaataac aactggattt ttgtcaatta     480
agcatgctct ctttagtttg ttgttggatt caattgttat ataataatat aatacatata     540
gatcgagaag tagtggttgc taatataagt aggagtacag tcattttaga aagtttgcct     600
caagaaatat aaggtttctg ggaaattag gctcatgaaa tggagtcata tatatcgaaa      660
cgcataacat gtcaaactga gatatattcg gttaaaatgc agctgaagag acgaagtcag     720
agagaaataa gggcagggat gatatcatgc aaaataaaag caatagcttt cacccccttg     780
ttcaattgac tttttataac taaaaaagaa ggaaataatt atgatatcat gcaaactata     840
agtgatgtat catgaggcgc aacgaagtaa cctatcctcc caaaagattt ttctgacaaa     900
attgtagctt cgaagagtgc cagataactc gtgagatcga gcaacaataa agcatgcatg     960
aaatcagttt cgatcaagct ggccaatgaa ctgaagggg gatcacttaa tgcaactcgt    1020
gatgatttca gatatatatg tatgtgtaga caagatctat atagacatgt gaagtacccg    1080
accgaaccat aaaggtagat tatttacccc tcgaattaag ttgagaacct ggctagccag    1140
agagatcgag atcgatggat tgaattgaat tgaattgaat tggatccagt gatgaccgag    1200
tggcctactg acctgctgca ctgctggcag aacctctgat gcagtccacc ggcggtgacg    1260
acgacgggcg ccttggagtg gtgctcgcac accttgtggc gacggtggta tctcttggcg    1320
ctggagaggt cggccttgca gccctcggcc tggcagcgcg gcgggtggtg gccgtacgtg    1380
tagcctcctc tgggcgggaa gtaggtgcgg tagccgaggt tgaggccgag ctgcgtggcg    1440
gcgaagctgg ccatgttctc ctcggcggag ctgacgaggg tggggaagta gtactcgggc    1500
gcggcctgcg ccgccgccgc cggcgggtag taggacgacg aggtctggtg gaaggtggtc    1560
ccgggcgcgg agactaagtg gctgtagggg ttgccgccgg cggcggcgag gtagtgcgag    1620
gcggcggaag gaggagggta gaagtggagg atgtcgtggg ggctgtggcc gccggcgaag    1680
gtggtgtggt ggtgggcggc ggcggcgttg gacggggggca ggagggccag cgagttggcc    1740
tcgaggttgt agcccagcag ctgatgatgc tccctgtgga tgctgctctc ctgctgctgc    1800
tccatggttg ggagcaggga aggggcgga gcggccgcgt tggacggcac gacgtagggg     1860
gggaactcgt cgcggccgtt ggcggcagcc gataggttca tcatcttccc acgcccggc     1920
cggcacgttg acacgatatc tcgatcgatc ggtcggcccg ccgcccgat ctgtgcaggt     1980
gcaggtcgcg cgggcgggcg cggctagctg ggagcctggg aggggaggag gggccggagg    2040
gagcaggagc aggagtgccc gcgcgcgcac acacgagcac acgaaatgg atgcgtaggg     2100
gacggagggg aggacggcgg caaggacagc gcttagcgga gagctcggtg gagatcgatc    2160
gctcagtcgg tcgcaggtgg acgagcgaca gacagagcta atacggcggt gttggccggc    2220
cgggccatgg tgtgggtgat ggcgatgaca cagatatatg cgcgggcggg cgccagctag    2280
tagccgggca gctagcgcgc gcccttctcg gccggccgga tctctttgc tgcggagagg     2340
```

```
gagagggcga gagcgagggc cgagagcgcg agtactttg gtctagggtt ccatggaacg     2400
agtggtggtg gagtgagttt tgggctatat ctaagagcga cgcccgcagc tcagctagca     2460
acaaaccggg cgctggcact gacagggccg gccagtagag agagagagag agatctttaa     2520
ttggagttgg tgagtggtga tagcagccgc agctgctgct gctgctgctg ctgcttcttt     2580
gtggttggtt tggttcgccc tccattttc ctcacccggg agtccgtatg ctatctgcta     2640
tatgctaggc tggctgtggg tgtctatgta tgtatcctcc tcctccgttg aaacaacgta     2700
gcgtacgaca ctgctgcatg tgtggccttg aagatatgag tatctatgca tgatgcggat     2760
gctgtacatg tgcattgcat cgctcttctc tctccctgcg gtggtgtgta cgagacggtg     2820
ggtacgtacg ctaacgctag cagctgcctc ccgcgtgacg ccaggggcag cccggccgga     2880
cgcggtgttt cgttccatga ccatgaggcg tgatctcagt catggcccaa ctacgccagg     2940
ggcttgcatt gcccgcgcgc gtagactttg cacctgcgca tgtatgtatg tacatcctgc     3000
agcgcacagc agactgagct gtattcccgc gcaaatgagt agcagcgcac gtatatatac     3060
gcgtacgcgt ac                                                         3072

<210> SEQ ID NO 19
<211> LENGTH: 15585
<212> TYPE: DNA
<213> ORGANISM: Artificial Sequence
<220> FEATURE:
<223> OTHER INFORMATION: PHP44779

<400> SEQUENCE: 19
gtttacccgc caatatatcc tgtcaaacac tgatagttta aactgaaggc gggaaacgac       60
aatctgatca tgagcggaga attaagggag tcacgttatg accccgccg atgacgcggg      120 acaagccgtt ttacgtttgg aactgacaga accgcaacgt tgaaggagcc actcagcaag      180
ctggtacgat tgtaatacga ctcactatag ggcgaattga gcgctgttta aacgctcttc      240
aactggaaga gcggttacta ccggctggat ggcggggcct tgatcgtgca ccgccggcgt      300
ccggactaac taactagtcg agctagttac cctatgaggt gacatgaagc gctcacggtt      360
actatgacgg ttagcttcac gactgttggt ggcagtagcg tacgacttag ctatagttcc      420
ggacttaccc ttaagataac ttcgtatagc atacattata cgaagttatg gcccaccgg      480 tggtaccgag ctcgttaaa cgctcttcaa ctggaagagc ggttaccaga gctggtcacc      540
tttgtccacc aagatggaac tggcgcgcct cattaattaa gtcagcggcc gctctagttg      600
aagacacgtt catgtcttca tcgtaagaag acactcagta gtcttcggcc agaatggcca      660
tctggattca gcaggcctag aaggccattt aaatcctgag gatctggtct tcctaaggac      720
ccgggatatc ggaccgaagc ttgcatgcct gcagtgcagc gtgacccggt cgtgcccctc      780
tctagagata atgagcattg catgtctaag ttataaaaaa ttaccacata ttttttttgt      840
cacacttgtt tgaagtgcag tttatctatc tttatacata tatttaaact ttactctacg      900
aataatataa tctatagtac tacaataata tcagtgtttt agagaatcat ataaatgaac      960
agttagacat ggtctaaagg acaattgagt attttgacaa caggactcta cagttttatc     1020
tttttagtgt gcatgtgttc tccttttttt ttgcaaatag cttcacctat ataatacttc     1080 atccattta ttagtacatc catttagggt ttagggttaa tggttttat agactaattt      1140 ttttagtaca tctattttat tctattttag cctctaaatt aagaaaacta aaactctatt     1200
ttagtttttt tatttaataa tttagatata aaatagaata aaataaagtg actaaaaatt     1260
```

```
aaacaaatac cctttaagaa attaaaaaaa ctaaggaaac attttcttg tttcgagtag     1320 ataatgccag cctgttaaac gccgtcgacg agtctaacgg acaccaacca gcgaaccagc    1380
agcgtcgcgt cgggccaagc gaagcagacg gcacggcatc tctgtcgctg cctctggacc   1440
cctctcgaga gttccgctcc accgttggac ttgctccgct gtcggcatcc agaaattgcg   1500
tggcggagcg gcagacgtga gccggcacgg caggcggcct cctcctcctc tcacggcacc   1560
ggcagctacg ggggattcct ttcccaccgc tccttcgctt tcccttcctc gcccgccgta   1620
ataaatagac accccctcca caccctcttt ccccaacctc gtgttgttcg gagcgcacac   1680
acacacaacc agatctcccc caaatccacc cgtcggcacc tccgcttcaa ggtacgccgc   1740
tcgtcctccc ccccccccct ctctaccttc tctagatcgg cgttccggtc catgcatggt   1800
tagggcccgg tagttctact tctgttcatg tttgtgttag atccgtgttt gtgttagatc   1860
cgtgctgcta gcgttcgtac acggatgcga cctgtacgtc agacacgttc tgattgctaa   1920
cttgccagtg tttctctttg gggaatcctg gatggctct agccgttccg cagacgggat    1980
cgatttcatg atttttttg tttcgttgca tagggtttgg tttgcccttt tcctttattt    2040
caatatatgc cgtgcacttg tttgtcgggt catcttttca tgctttttt tgtcttggtt    2100 gtgatgatgt ggtctggttg ggcggtcgtt ctagatcgga gtagaattct gtttcaaact   2160
acctggtgga tttattaatt ttggatctgt atgtgtgtgc catacatatt catagttacg   2220
aattgaagat gatggatgga aatatcgatc taggataggt atacatgttg atgcgggttt   2280
tactgatgca tatacagaga tgcttttgt tcgcttggtt gtgatgatgt ggtgtggttg    2340
ggcggtcgtt cattcgttct agatcggagt agaatactgt ttcaaactac ctggtgtatt   2400
tattaatttt ggaactgtat gtgtgtgtca tacatcttca tagttacgag tttaagatgg   2460
atggaaatat cgatctagga taggtataca tgttgatgtg ggttttactg atgcatatac   2520
atgatggcat atgcagcatc tattcatatg ctctaacctt gagtacctat ctattataat   2580
aaacaagtat gttttataat tattttgatc ttgatatact tggatgatgg catatgcagc   2640
agctatatgt ggatttttt agccctgcct tcatacgcta tttatttgct tggtactgtt    2700
tcttttgtcg atgctcaccc tgttgtttgg tgttacttct gcaggtcgac tctagaggat   2760
ccatggcacc gaagaagaag cgcaaggtgc atatgaacac caagtacaac aaggagttcc   2820
tgctctacct ggccggcttc gtggacggcg acggctccat catcgcgcag atcaagccga   2880
accagtccta caagttcaag caccagctca tgctgacctt caccgtgacc cagaagacgc   2940
agaggcgctg gttcctcgac aagctggtcg acgagatcgg ggtgggcaag gtccgcgacc   3000
gcgggtcggt gtccgactac atcctctccc agatcaagcc cctgcacaac ttcctcaccc   3060
agctccagcc gttcctcaag ctgaagcaga gcaggcgaa cctcgtcctg aagatcatcg    3120
agcagctccc ctcggccaag gagtccccgg acaagttcct ggaggtgtgc acgtgggtcg   3180
accagatcgc ggccctcaac gacagcaaga cccgcaagac gacctcggag acggtgcggg   3240
cggtcctgga ctccctccca ggatccgtgg gaggtctatc gccatctcag gcatccagcg   3300
ccgcatcctc ggcttcctca gcccgggtt cagggatctc cgaagcactc agagctggag    3360
caactaagtc caaggaattc ctgctctacc tggccggctt cgtggacggc gacggctcca   3420
tcatcgcggc gatcaagccg aaccagtcct acaagttcaa gcaccagctc tccctgacct   3480
tcaccgtgac ccagaagacg cagaggcgct ggttcctcga caagctggtc gacgagatcg   3540
gggtgggcta cgtccgcgac caggggtcgg tgtcccacta ccagctctcc cagatcaagc   3600
ccctgcacaa cttcctcacc cagctccagc cgttcctcaa gctgaagcag aagcaggcga   3660
```

```
acctcgtcct gaagatcatc gagcagctcc cctcggccaa ggagtccccg gacaagttcc    3720
tggaggtgtg cacgtgggtc gaccagatcg cggccctcaa cgacagcaag acccgcaaga    3780
cgacctcgga gacggtgcgg gcggttctag actccctcag cgagaagaag aagtcgtccc    3840
cctgaggtac cacatggtta acctagactt gtccatcttc tggattggcc aacttaatta    3900
atgtatgaaa taaaaggatg cacacatagt gacatgctaa tcactataat gtgggcatca    3960
aagttgtgtg ttatgtgtaa ttactagtta tctgaataaa agagaaagag atcatccata    4020
tttcttatcc taaatgaatg tcacgtgtct ttataattct ttgatgaacc agatgcattt    4080
cattaaccaa atccatatac atataaatat taatcatata taattaatat caattgggtt    4140
agcaaaacaa atctagtcta ggtgtgtttt gcgaatgcgg ccgccaccgc ggtggagctc    4200
gaattccggt ccgataactt cgtatagcat acattatacg aagttatacc tggtggcgtc    4260
actttccccc ctattttct ccctattttt tcatctcccg cagcggttcc ccctaaatac    4320
tcctatatac cccaatacaa ctataaaata tcattttcta tatcaactat caattttta    4380 tctactaaca attactcgtg gacccacatc acaatgttta gggtgatgaa cagtgacacg    4440
ctagatctga ggggagagag aaaagggtcg gcgcgtaggg ggcgctgtag ggggcaccgc    4500
tgcggctgtg gagtgccccc tacagccccc atgcaagggg agggggatac tgagggggct    4560
gcgttgcgta cagcctgaca ggctctcctt cgcatttgcg cgggacagaa atgacttgcc    4620
gaggatggaa gcagagagac ggatttggcc gagcgcacag cagctcgcca aagacggcgt    4680
cgaagcagca gtgaccgcgg tcgagtgagg gagtcatcct ggattcgcgg tttatcgact    4740
cggcacgggg gcaaccatgg cgttgaaggt aggcaacatg aggagccatc gattgacacc    4800
ggtcttcgga atcggcggat ctcgacgatg gtgacaagga ggaggccacg aagcgtcgtc    4860
gagcagagcg cgacaagcaa atcgagtcgg ccacgagcgt ggatttggat ctgaccccca    4920 agttttgta tggatcctat tccccaattt gtagatcttc aatttcctta ctttaattt     4980 ccatagcaca aacgatgttt gcatgcacga ttcggacaat cttgacttgt tcgtccacgg    5040
ttggagttta gggttggaat gtgtaaaaca cgtgataaac tgtgtacaac tcgagaacta    5100
gataattcat tttggattgt aatatgtgta cctcatgcta tagttttggt taaatctgac    5160
gtgaaagggc gaattcgccg ctagcctgca gtgcagcgtg acccggtcgt gcccctctct    5220
agagataatg agcattgcat gtctaagtta taaaaaatta ccacatattt ttttgtcac    5280 acttgtttga agtgcagttt atctatcttt atacatatat ttaaacttta ctctacgaat    5340
aatataatct atagtactac aataatatca gtgtttagga gaatcatata aatgaacagt    5400
tagacatggt ctaaaggaca attgagtatt ttgacaacag gactctacag ttttatcttt    5460
ttagtgtgca tgtgttctcc ttttttttg caaatagctt cacctatata atacttcatc    5520
catttattta gtacatccat ttagggttta gggttaatgg tttttataga ctaattttt    5580 tagtacatct attttattct attttagcct ctaaattaag aaaactaaaa ctctatttta    5640
gtttttttat ttaataattt agatataaaa tagaataaaa taaagtgact aaaaattaaa    5700
caaataccct ttaagaaatt aaaaaaacta aggaaacatt tttcttgttt cgagtagata    5760
atgccagcct gttaaacgcc gtcgacgagt ctaacgacca ccaaccagcg aaccagcagc    5820
gtcgcgtcgg gccaagcgaa gcagacggca cggcatctct gtcgctgcct ctggaccct    5880 ctcgagagtt ccgctccacc gttggacttg ctccgctgtc ggcatccaga aattgcgtgg    5940
cggagcggca gacgtgagcc ggcacggcag gcggcctcct cctcctctca cggcaccggc    6000
```

```
agctacgggg gattcctttc ccaccgctcc ttcgctttcc cttcctcgcc cgccgtaata    6060
aatagacacc ccctccacac cctctttccc caacctcgtg ttgttcggag cgcacacaca    6120
cacaaccaga tctcccccaa atccacccgt cggcacctcc gcttcaaggt acgccgctcg    6180 tcctccccc ccccctctc taccttctct agatcggcgt tccggtccat gcatggttag      6240
ggcccggtag ttctacttct gttcatgttt gtgttagatc cgtgtttgtg ttagatccgt    6300
gctgctagcg ttcgtacacg gatgcgacct gtacgtcaga cacgttctga ttgctaactt    6360
gccagtgttt ctctttgggg aatcctggga tggctctagc cgttccgcag acgggatcga    6420
tttcatgatt ttttttgttt cgttgcatag ggtttggttt gccctttttcc tttatttcaa    6480 tatatgccgt gcacttgttt gtcgggtcat cttttcatgc ttttttttgt cttggttgtg    6540
atgatgtggt ctggttgggc ggtcgttcta gatcggagta gaattctgtt tcaaactacc    6600
tggtggattt attaattttg gatctgtatg tgtgtgccat acatattcat agttacgaat    6660
tgaagatgat ggatggaaat atcgatctag gataggtata catgttgatg cgggttttac    6720
tgatgcatat acagagatgc ttttttgttcg cttggttgtg atgatgtggt gtggttgggc    6780
ggtcgttcat tcgttctaga tcggagtaga atactgtttc aaactacctg gtgtatttat    6840
taattttgga actgtatgtg tgtgtcatac atcttcatag ttacgagttt aagatggatg    6900
gaaatatcga tctaggatag gtatacatgt tgatgtgggt tttactgatg catatacatg    6960
atggcatatg cagcatctat tcatatgctc taaccttgag tacctatcta ttataataaa    7020
caagtatgtt ttataattat tttgatcttg atatacttgg atgatggcat atgcagcagc    7080
tatatgtgga ttttttttagc cctgccttca tacgctattt atttgcttgg tactgtttct    7140
tttgtcgatg ctcaccctgt tgtttggtgt tacttctgca ggtcgactct agaggatcaa    7200
ttcgctagcg aagttcctat tccgaagttc ctattctcta aaagtatag gaacttcaga    7260 tccaccggga tccacacgac accatgtccc ccgagcgccg ccccgtcgag atccgcccgg    7320
ccaccgccgc cgacatggcc gccgtgtgcg acatcgtgaa ccactacatc gagacctcca    7380
ccgtgaactt ccgcaccgag ccgcagaccc gcaggagtg gatcgacgac ctggagcgcc    7440
tccaggaccg ctacccgtgg ctcgtggccg aggtggaggg cgtggtggcc ggcatcgcct    7500
acgccggccc gtggaaggcc cgcaacgcct acgactggac cgtggagtcc accgtgtacg    7560
tgtcccaccg ccaccagcgc ctcggcctcg gctccaccct ctacacccac ctcctcaaga    7620
gcatggaggc ccagggcttc aagtccgtgg tggccgtgat cggcctcccg aacgacccgt    7680
ccgtgcgcct ccacgaggcc ctcggctaca ccgcccgcgg caccctccgc gccgccggct    7740
acaagcacgg cggctggcac gacgtcggct tctggcagcg cgacttcgag ctgccggccc    7800
cgccgcgccc ggtgcgcccg gtgacgcaga tctgagtcga acctagact tgtccatctt    7860 ctggattggc caacttaatt aatgtatgaa ataaaggat gcacacatag tgacatgcta    7920
atcactataa tgtgggcatc aaagttgtgt gttatgtgta attactagtt atctgaataa    7980
aagagaaaga gatcatccat atttcttatc ctaaatgaat gtcacgtgtc tttataattc    8040
tttgatgaac cagatgcatt tcattaacca aatccatata catataaata ttaatcatat    8100
ataattaata tcaattgggt tagcaaaaca aatctagtct aggtgtgttt tgcgaatgcg    8160
gccctagcgt atacgaagtt cctattccga agttcctatt ctccagaaag tataggaact    8220
tctgtacacc tgagctgatt ccgatgactt cgtaggttcc tagctcaagc cgctcgtgtc    8280
caagcgtcac ttcgattag ctaatgatta cggcatctag gaccgactag ctaactaact    8340
agtacaattc gcccttgtga atctgtttgg aattgaaaaa caagtgcttc cttttataca    8400
```

```
ccactatgtc gcttcaatgt ttgcgaacca aggtaaagaa atgtaaaatc ttacaatttc    8460
cgtgcatccg acataaatct gtggtcacat agctattgtt aaacggttgc aaatcctaag    8520
gaggaccatt attgtgcaac aactacatat ggtagaagcg cttgttttga tgtgtgcaca    8580
ttttgttgct aaaaggatca cgatgcccaa gagggggtg aattgggctt ttctaaaaat     8640
caacactaat taaaacctaa gcaagagccc aacttcaccc cgacaactag caataagaga    8700
atatgaaagg gaaataggat caaacctttt cctaaatgat tttggtggtt gaattgccca    8760
acacaaataa ttggactaac tagtttgctc tagatcatac attctacagg tgccaaaggt    8820
tcaacacaaa ccaatcaaaa gaacaagtta ggcttcaaaa gaaaggagca aaaggaaac     8880 cgaagtgtgc ctggtctggc gcaccgggct gtccggtgtg ccaccagaca gtgtccggtg    8940
caccagggtg aatcagctca agctcctcaa cttcgggttt cccagacgca gctccactat    9000
aattcattgg actgtccggt gcacccgcag agcaacggct acttgcgcgc aacggtcgac    9060
tctgcaaagt gaacagtgca attcagaagt cagagcagat ggtcagaggg gcaccggatt    9120
gtccggtgta gcaccggact gtccggtgcc gcatgaggac aaagcctcca acggtcgacc    9180
agctccaagc cctaactaca agatgacgtg gcggcgcacc ggacactgtc cggtggtgca    9240
ccggactgtt cggtgcgccc atcgccagta gccttctcca acggctacaa tttggttggt    9300
ggctataaat accaccccaa ccggccactt taaggtgtgg gagcccaagc aacattccaa    9360
gtcatatagt tgacatattc aagccatccc aaccaccgta gaattaattc attccgatta    9420
atcgtggcct cttgctcttc aggatgaaga gctatgttta aacgtgcaag cgctactaga    9480
caattcagta cattaaaaac gtccgcaatg tgttattaag ttgtctaagc gtcaatttgt    9540
ttacaccaca atatatcctg ccaccagcca gccaacagct ccccgaccgg cagctcggca    9600
caaaatcacc actcgataca ggcagcccat cagtccggga cggcgtcagc gggagagccg    9660
ttgtaaggcg gcagactttg ctcatgttac cgatgctatt cggaagaacg gcaactaagc    9720
tgccgggttt gaaacacgga tgatctcgcg gagggtagca tgttgattgt aacgatgaca    9780
gagcgttgct gcctgtgatc aaatatcatc tccctcgcag agatccgaat tatcagcctt    9840
cttattcatt tctcgcttaa ccgtgacagg ctgtcgatct tgagaactat gccgacataa    9900
taggaaatcg ctggataaag ccgctgagga agctgagtgg cgctatttct ttagaagtga    9960
acgttgacga tcgtcgaccg taccccgatg aattaattcg gacgtacgtt ctgaacacag   10020
ctggatactt acttgggcga ttgtcataca tgacatcaac aatgtacccg tttgtgtaac   10080
cgtctcttgg aggttcgtat gacactagtg gttcccctca gcttgcgact agatgttgag   10140
gcctaacatt ttattagaga gcaggctagt tgcttagata catgatcttc aggccgttat   10200
ctgtcagggc aagcgaaaat tggccattta tgacgaccaa tgccccgcag aagctcccat   10260
ctttgccgcc atagacgccg cgcccccctt ttggggtgta aacatccttt tgccagatg    10320 tggaaaagaa gttcgttgtc ccattgttgg caatgacgta gtagccggcg aaagtgcgag   10380
acccatttgc gctatatata agcctacgat ttccgttgcg actattgtcg taattggatg   10440
aactattatc gtagttgctc tcagagttgt cgtaatttga tggactattg tcgtaattgc   10500
ttatggagtt gtcgtagttg cttggagaaa tgtcgtagtt ggatggggag tagtcatagg   10560
gaagacgagc ttcatccact aaaacaattg gcaggtcagc aagtgcctgc cccgatgcca   10620
tcgcaagtac gaggcttaga accaccttca acagatcgcg catagtcttc cccagctctc   10680
taacgcttga gttaagccgc gccgcgaagc ggcgtcggct tgaacgaatt gttagacatt   10740
```

```
atttgccgac taccttggtg atctcgcctt tcacgtagtg aacaaattct tccaactgat   10800
ctgcgcgcga ggccaagcga tcttcttgtc caagataagc ctgcctagct tcaagtatga   10860
cgggctgata ctgggccggc aggcgctcca ttgcccagtc ggcagcgaca tccttcggcg   10920
cgattttgcc ggttactgcg ctgtaccaaa tgcgggacaa cgtaagcact acatttcgct   10980
catcgccagc ccagtcgggc ggcgagttcc atagcgttaa ggtttcattt agcgcctcaa   11040
atagatcctg ttcaggaacc ggatcaaaga gttcctccgc cgctggacct accaaggcaa   11100
cgctatgttc tcttgctttt gtcagcaaga tagccagatc aatgtcgatc gtggctggct   11160
cgaagatacc tgcaagaatg tcattgcgct gccattctcc aaattgcagt cgcgcttag   11220 ctggataacg ccacggaatg atgtcgtcgt gcacaacaat ggtgacttct acagcgcgga   11280
gaatctcgct ctctccaggg gaagccgaag tttccaaaag gtcgttgatc aaagctcgcc   11340
gcgttgtttc atcaagcctt acagtcaccg taaccagcaa atcaatatca ctgtgtggct   11400
tcaggccgcc atccactgcg gagccgtaca aatgtacggc cagcaacgtc ggttcgagat   11460
ggcgctcgat gacgccaact acctctgata gttgagtcga tacttcggcg atcaccgctt   11520
ccctcatgat gtttaactcc tgaattaagc cgcgccgcga agcggtgtcg gcttgaatga   11580
attgttaggc gtcatcctgt gctcccgaga accagtacca gtacatcgct gtttcgttcg   11640
agacttgagg tctagtttta tacgtgaaca ggtcaatgcc gccgagagta aagccacatt   11700
ttgcgtacaa attgcaggca ggtacattgt tcgtttgtgt ctctaatcgt atgccaagga   11760
gctgtctgct tagtgcccac ttttttcgcaa attcgatgag actgtgcgcg actcctttgc   11820
ctcggtgcgt gtgcgacaca acaatgtgtt cgatagaggc tagatcgttc catgttgagt   11880
tgagttcaat cttcccgaca agctcttggt cgatgaatgc gccatagcaa gcagagtctt   11940
catcagagtc atcatccgag atgtaatcct tccggtaggg gctcacactt ctggtagata   12000
gttcaaagcc ttggtcggat aggtgcacat cgaacacttc acgaacaatg aaatggttct   12060
cagcatccaa tgtttccgcc acctgctcag ggatcaccga atcttcata tgacgcctaa   12120 cgcctggcac agcggatcgc aaacctggcg cggcttttgg cacaaaaggc gtgacaggtt   12180
tgcgaatccg ttgctgccac ttgttaaccc ttttgccaga tttggtaact ataatttatg   12240
ttagaggcga agtcttgggt aaaaactggc ctaaaattgc tggggatttc aggaaagtaa   12300
acatcacctt ccggctcgat gtctattgta gatatatgta gtgtatctac ttgatcgggg   12360
gatctgctgc ctcgcgcgtt tcggtgatga cggtgaaaac ctctgacaca tgcagctccc   12420
ggagacggtc acagcttgtc tgtaagcgga tgccgggagc agacaagccc gtcagggcgc   12480
gtcagcgggt gttggcgggt gtcggggcgc agccatgacc cagtcacgta gcgatagcgg   12540
agtgtatact ggcttaacta tgcggcatca gagcagattg tactgagagt gcaccatatg   12600
cggtgtgaaa taccgcacag atgcgtaagg agaaaatacc gcatcaggcg ctcttccgct   12660
tcctcgctca ctgactcgct gcgctcggtc gttcggctgc ggcgagcggt atcagctcac   12720
tcaaaggcgg taatacggtt atccacagaa tcagggggata acgcaggaaa gaacatgtga   12780
gcaaaaggcc agcaaaaggc caggaaccgt aaaaaggccg cgttgctggc gtttttccat   12840
aggctccgcc cccctgacga gcatcacaaa aatcgacgct caagtcagag gtggcgaaac   12900
ccgacaggac tataaagata ccaggcgttt ccccctggaa gctccctcgt gcgctctcct   12960
gttccgaccc tgccgcttac cggatacctg tccgcctttc tcccttcggg aagcgtggcg   13020
ctttctcata gctcacgctg taggtatctc agttcggtgt aggtcgttcg ctccaagctg   13080
ggctgtgtgc acgaaccccc cgttcagccc gaccgctgcg ccttatccgg taactatcgt   13140
```

```
cttgagtcca acccggtaag acacgactta tcgccactgg cagcagccac tggtaacagg    13200
attagcagag cgaggtatgt aggcggtgct acagagttct tgaagtggtg gcctaactac    13260
ggctacacta aaggacagt atttggtatc tgcgctctgc tgaagccagt taccttcgga    13320
aaaagagttg gtagctcttg atccggcaaa caaaccaccg ctggtagcgg tggtttttt    13380 gtttgcaagc agcagattac gcgcagaaaa aaggatctc aagaagatcc tttgatcttt    13440
tctacggggt ctgacgctca gtggaacgaa aactcacgtt aagggatttt ggtcatgaga    13500
ttatcaaaaa ggatcttcac ctagatcctt ttaaattaaa aatgaagttt taaatcaatc    13560
taaagtatat atgagtaaac ttggtctgac agttaccaat gcttaatcag tgaggcacct    13620
atctcagcga tctgtctatt tcgttcatcc atagttgcct gactccccgt cgtgtagata    13680
actacgatac gggagggctt accatctggc cccagtgctg caatgatacc gcgagaccca    13740
cgctcaccgg ctccagattt atcagcaata aaccagccag ccggaagggc cgagcgcaga    13800
agtggtcctg caactttatc cgcctccatc cagtctatta attgttgccg ggaagctaga    13860
gtaagtagtt cgccagttaa tagtttgcgc aacgttgttg ccattgctgc agggggggg    13920 gggggggggg acttccattg ttcattccac ggacaaaaac agagaaagga acgacagag    13980 gccaaaaagc ctcgctttca gcacctgtcg tttcctttct tttcagaggg tattttaaat    14040
aaaaacatta agttatgacg aagaagaacg gaaacgcctt aaaccggaaa attttcataa    14100
atagcgaaaa cccgcgaggt cgccgccccg taacctgtcg gatcaccgga aaggacccgt    14160
aaagtgataa tgattatcat ctacatatca caacgtgcgt ggaggccatc aaaccacgtc    14220
aaataatcaa ttatgacgca ggtatcgtat taattgatct gcatcaactt aacgtaaaaa    14280
caacttcaga caatacaaat cagcgacact gaatacgggg caacctcatg tccccccccc    14340 cccccccct gcaggcatcg tggtgtcacg ctcgtcgttt ggtatggctt cattcagctc    14400
cggttcccaa cgatcaaggc gagttacatg atccccatg ttgtgcaaaa aagcggttag    14460
ctccttcggt cctccgatcg ttgtcagaag taagttggcc gcagtgttat cactcatggt    14520
tatggcagca ctgcataatt ctcttactgt catgccatcc gtaagatgct tttctgtgac    14580
tggtgagtac tcaaccaagt cattctgaga atagtgtatg cggcgaccga gttgctcttg    14640
cccggcgtca acacgggata ataccgcgcc acatagcaga actttaaaag tgctcatcat    14700
tggaaaacgt tcttcgggc gaaaactctc aaggatctta ccgctgttga tccagttc    14760 gatgtaaccc actcgtgcac ccaactgatc ttcagcatct tttactttca ccagcgtttc    14820
tgggtgagca aaaacaggaa ggcaaaatgc cgcaaaaaag gaataaggg cgacacggaa    14880 atgttgaata ctcatactct tccttttttca atattattga agcatttatc agggttattg    14940
tctcatgagc ggatacatat ttgaatgtat ttagaaaaat aaacaaatag gggttccgcg    15000
cacatttccc cgaaaagtgc cacctgacgt ctaagaaacc attattatca tgacattaac    15060
ctataaaaat aggcgtatca cgaggccctt tcgtcttcaa gaattggtcg acgatcttgc    15120
tgcgttcgga tattttcgtg gagttcccgc cacagacccg gattgaaggc gagatccagc    15180
aactcgcgcc agatcatcct gtgacggaac tttggcgcgt gatgactggc caggacgtcg    15240
gccgaaagag cgacaagcag atcacgcttt tcgacacgcg cggatttgcg atcgaggatt    15300
tttcggcgct gcgctacgtc cgcgaccgcg ttgagggatc aagccacagc agcccactcg    15360
accttctagc cgacccagac gagccaaggg atcttttgg aatgctgctc cgtcgtcagg    15420 cttttccgacg tttgggtggt tgaacagaag tcattatcgt acggaatgcc aagcactccc    15480
```

```
gaggggaacc ctgtggttgg catgcacata caaatggacg aacggataaa ccttttcacg    15540 ccctttaaa tatccgttat tctaataaac gctctttct cttag                     15585
```

<210> SEQ ID NO 20
<211> LENGTH: 22
<212> TYPE: DNA
<213> ORGANISM: Zea mays
<220> FEATURE:
<221> NAME/KEY: misc_feature
<222> LOCATION: (1)..(22)
<223> OTHER INFORMATION: the MHP14 recognition site

<400> SEQUENCE: 20

```
caaacagatt cacgtcagat tt                                                22
```

<210> SEQ ID NO 21
<211> LENGTH: 1083
<212> TYPE: DNA
<213> ORGANISM: Artificial Sequence
<220> FEATURE:
<223> OTHER INFORMATION: plant-optimized nucleotide sequence of MHP14+

<400> SEQUENCE: 21

```
atggcaccga agaagaagcg caaggtgcat atgaacacca agtacaacaa ggagttcctg      60
ctctacctgg ccggcttcgt ggacggcgac ggctccatca tcgcgcagat caagccgaac    120
cagtcctaca agttcaagca ccagctcatg ctgaccttca ccgtgaccca gaagacgcag    180
aggcgctggt tcctcgacaa gctggtcgac gagatcgggg tgggcaaggt ccgcgaccgc    240
gggtcggtgt ccgactacat cctctcccag atcaagcccc tgcacaactt cctcacccag    300
ctccagccgt tcctcaagct gaagcagaag caggcgaacc tcgtcctgaa gatcatcgag    360 cagctccccct cggccaagga gtccccggac aagttcctgg aggtgtgcac gtgggtcgac    420
cagatcgcgg ccctcaacga cagcaagacc cgcaagacga cctcggagac ggtgcgggcg    480
gtcctggact ccctcccagg atccgtggga ggtctatcgc catctcaggc atccagcgcc    540
gcatcctcgg cttcctcaag cccgggttca gggatctccg aagcactcag agctggagca    600
actaagtcca aggaattcct gctctacctg gccggcttcg tggacggcga cggctccatc    660
atcgcggcga tcaagccgaa ccagtcctac aagttcaagc accagctctc cctgaccttc    720
accgtgaccc agaagacgca gaggcgctgg ttcctcgaca agctggtcga cgagatcggg    780
gtgggctacg tccgcgacca ggggtcggtg tccactacc agctctccca gatcaagccc    840
ctgcacaact tcctcaccca gctccagccg ttcctcaagc tgaagcagaa gcaggcgaac    900
ctcgtcctga agatcatcga gcagctcccc tcggccaagg agtccccgga caagttcctg    960
gaggtgtgca cgtgggtcga ccagatcgcg gccctcaacg acagcaagac cgcaagacg   1020 acctcggaga cggtgcgggc ggttctagac tccctcagcg agaagaagaa gtcgtccccc    1080
tga                                                                1083
```

<210> SEQ ID NO 22
<211> LENGTH: 1041
<212> TYPE: DNA
<213> ORGANISM: Zea mays
<220> FEATURE:
<221> NAME/KEY: misc_feature
<222> LOCATION: (1)..(1041)
<223> OTHER INFORMATION: HR1 of the MHP14

<400> SEQUENCE: 22

```
gtgaatctgt ttggaattga aaaacaagtg cttccttta tacaccacta tgtcgcttca     60
```

```
atgtttgcga accaaggtaa agaaatgtaa aatcttacaa tttccgtgca tccgacataa        120
atctgtggtc acatagctat tgttaaacgg ttgcaaatcc taaggaggac cattattgtg        180
caacaactac atatggtaga agcgcttgtt ttgatgtgtg cacattttgt tgctaaaagg        240
atcacgatgc ccaagagggg ggtgaattgg gcttttctaa aaatcaacac taattaaaac        300
ctaagcaaga gcccaacttc accccgacaa ctagcaataa gagaatatga aagggaaata        360
ggatcaaacc ttttcctaaa tgattttggt ggttgaattg cccaacacaa ataattggac        420
taactagttt gctctagatc atacattcta caggtgccaa aggttcaaca caaaccaatc        480
aaaagaacaa gttaggcttc aaaagaaagg agcaaaaagg aaaccgaagt gtgcctggtc        540
tggcgcaccg ggctgtccgg tgtgccacca gacagtgtcc ggtgcaccag ggtgaatcag        600
ctcaagctcc tcaacttcgg gtttcccaga cgcagctcca ctataattca ttggactgtc        660
cggtgcaccc gcagagcaac ggctacttgc gcgcaacggt cgactctgca aagtgaacag        720
tgcaattcag aagtcagagc agatggtcag aggggcaccg gattgtccgg tgtagcaccg        780
gactgtccgg tgccgcatga ggacaaagcc tccaacggtc gaccagctcc aagccctaac        840
tacaagatga cgtggcggcg caccggacac tgtccggtgg tgcaccggac tgttcggtgc        900
gcccatcgcc agtagccttc tccaacggct acaatttggt tggtggctat aaataccacc        960
ccaaccggcc actttaaggt gtgggagccc aagcaacatt ccaagtcata tagttgacat       1020
attcaagcca tcccaaccac c                                                  1041

<210> SEQ ID NO 23
<211> LENGTH: 906
<212> TYPE: DNA
<213> ORGANISM: Zea mays
<220> FEATURE:
<221> NAME/KEY: misc_feature
<222> LOCATION: (1)..(906)
<223> OTHER INFORMATION: HR1 of the MHP14
<220> FEATURE:
<221> NAME/KEY: misc_feature
<222> LOCATION: (1)..(906)
<223> OTHER INFORMATION: HR2 of the MHP14

<400> SEQUENCE: 23
tcactttccc ccctattttt ctccctattt tttcatctcc cgcagcggtt cccccctaaat        60 actcctatat accccaatac aactataaaa tatcattttc tatatcaact atcaattttt       120
tatctactaa caattactcg tggacccaca tcacaatgtt tagggtgatg aacagtgaca       180
cgctagatct gagggagag agaaaagggt cggcgcgtag ggggcgctgt agggggcacc        240
gctgcggctg tggagtgccc cctacagccc ccatgcaagg ggaggggat actgagggg         300 ctgcgttgcg tacagcctga caggctctcc ttcgcatttg cgcgggacag aaatgacttg        360
ccgaggatgg aagcagagag acggatttgg ccgagcgcac agcagctcgc caaagacggc        420
gtcgaagcag cagtgaccgc ggtcgagtga gggagtcatc ctggattcgc ggtttatcga        480
ctcggcacgg gggcaaccat ggcgttgaag gtaggcaaca tgaggagcca tcgattgaca        540
ccggtcttcg gaatcggcgg atctcgacga tggtgacaag gaggaggcca cgaagcgtcg        600
tcgagcagag cgcgacaagc aaatcgagtc ggccacgagc gtggatttgg atctgacccc        660 caagttttttg tatggatcct attccccaat ttgtagatct tcaatttcct tactttaatt        720
ttccatagca caaacgatgt ttgcatgcac gattcggaca atcttgactt gttcgtccac        780
ggttggagtt tagggttgga atgtgtaaaa cacgtgataa actgtgtaca actcgagaac        840
```

```
tagataattc attttggatt gtaatatgtg tacctcatgc tatagttttg gttaaatctg    900
acgtga                                                                906

<210> SEQ ID NO 24
<211> LENGTH: 6608
<212> TYPE: DNA
<213> ORGANISM: Artificial Sequence
<220> FEATURE:
<223> OTHER INFORMATION: transfer cassette plasmid PHP27064

<400> SEQUENCE: 24
caggaaacag ctatgaccat gattacgcca agctatcaac tttgtataga aaagttgaag     60
ctctagcgaa gttcctattc cgaagttcct attctctaga aagtataqga acttcagatc    120 cacacgacac catggctatt gaggttaagc ctatcaacgc agaggatacc tatgacctta    180
ggcatagagt gctcagacca aaccagccta tcgaagcctg catgtttgag tctgacctta    240
ctaggagtgc atttcacctt ggtggattct acggaggtaa actgattccc gtggcttcat    300
tccaccaagc tgagcactct gaacttcaag gtaagaagca gtaccagctt agaggtgtgg    360
ctaccttgga aggttataga gagcagaagg ctggttccag tctcgtgaaa cacgctgaag    420
agattctcag aaagagaggt gctgacatga tctggtgtaa tgccaggaca tctgcttcag    480
gatactacag gaagttggga ttcagtgagc aaggagaggt gttcgatact cctccagttg    540
gacctcacat cctgatgtat aagaggatca cataactagc tagtcagtta acctagactt    600
gtccatcttc tggattggcc aacttaatta atgtatgaaa taaaggatg cacacatagt     660 gacatgctaa tcactataat gtgggcatca agttgtgtg ttatgtgtaa ttactagtta    720
tctgaataaa agagaaagag atcatccata tttcttatcc taaatgaatg tcacgtgtct    780
ttataattct ttgatgaacc agatgcattt cattaaccaa atccatatac atataaatat    840
taatcatata taattaatat caattgggtt agcaaaacaa atctagtcta ggtgtgtttt    900
gcgaattgcg gccgggtacc gagctcgaat tcggcccaag tttgtacaaa aaagcaggct    960
ccggccagaa tggcccggac cgaagcttgc atgcctgcag tgcagcgtga cccggtcgtg   1020
cccctctcta gagataatga gcattgcatg tctaagttat aaaaaattac acatattt    1080 ttttgtcaca cttgtttgaa gtgcagttta tctatcttta tacatatatt taaactttac   1140
tctacgaata atataatcta tagtactaca ataatatcag tgttttagag aatcatataa   1200
atgaacagtt agacatggtc taaaggacaa ttgagtattt tgacaacagg actctacagt   1260
tttatctttt tagtgtgcat gtgttctcct tttttttgc aaatagcttc acctatataa   1320
tacttcatcc attttattag tacatccatt tagggtttag ggttaatggt ttttatagac   1380
taattttttt agtacatcta ttttattcta ttttagcctc taaattaaga aaactaaaac   1440
tctattttag ttttttttatt taataattta gatataaaat agaataaaat aaagtgacta   1500
aaaattaaac aaataccctt taagaaatta aaaaaactaa ggaaacattt ttcttgtttc   1560
gagtagataa tgccagcctg ttaaacgccg tcgacgagtc taacgacac caaccagcga   1620 accagcagcg tcgcgtcggg ccaagcgaag cagacggcac ggcatctctg tcgctgcctc   1680
tggacccctc tcgagagttc cgctccaccg ttggacttgc tccgctgtcg gcatccagaa   1740
attgcgtggc ggagcggcag acgtgagccg gcacggcagg cggcctcctc ctcctctcac   1800
ggcaccggca gctacggggg attccttttcc caccgctcct tcgctttccc ttcctcgccc   1860
gccgtaataa atagacaccc cctccacacc ctctttcccc aacctcgtgt tgttcggagc   1920
gcacacacac acaaccagat ctcccccaaa tccacccgtc ggcacctccg cttcaaggta   1980
```

```
cgccgctcgt cctccccccc ccccctctct accttctcta gatcggcgtt ccggtccatg    2040
catggttagg gcccggtagt tctacttctg ttcatgtttg tgttagatcc gtgtttgtgt    2100
tagatccgtg ctgctagcgt tcgtacacgg atgcgacctg tacgtcagac acgttctgat    2160
tgctaacttg ccagtgtttc tctttgggga atcctgggat ggctctagcc gttccgcaga    2220
cgggatcgat ttcatgattt tttttgtttc gttgcatagg gtttggtttg cccttttcct    2280
ttatttcaat atatgccgtg cacttgtttg tcgggtcatc ttttcatgct tttttttgtc    2340
ttggttgtga tgatgtggtc tggttgggcg gtcgttctag atcggagtag aattctgttt    2400
caaactacct ggtggattta ttaattttgg atctgtatgt gtgtgccata catattcata    2460
gttacgaatt gaagatgatg gatggaaata tcgatctagg ataggtatac atgttgatgc    2520
gggttttact gatgcatata cagagatgct ttttgttcgc ttggttgtga tgatgtggtg    2580
tggttgggcg gtcgttcatt cgttctagat cggagtagaa tactgtttca aactacctgg    2640
tgtatttatt aattttggaa ctgtatgtgt gtgtcataca tcttcatagt tacgagttta    2700
agatggatgg aaatatcgat ctaggatagg tatacatgtt gatgtgggtt ttactgatgc    2760
atatacatga tggcatatgc agcatctatt catatgctct aaccttgagt acctatctat    2820
tataataaac aagtatgttt tataattatt ttgatcttga tatacttgga tgatggcata    2880
tgcagcagct atatgtggat ttttttagcc ctgccttcat acgctattta tttgcttggt    2940
actgtttctt ttgtcgatgc tcaccctgtt gtttggtgtt acttctgcag gtcgactcta    3000
gaggatccac cggtcgccac catggcccac agcaagcacg gcctgaagga ggagatgacc    3060
atgaagtacc acatggaggg ctgcgtgaac ggccacaagt tcgtgatcac cggcgagggc    3120
atcggctacc ccttcaaggg caagcagacc atcaacctgt gcgtgatcga gggcggcccc    3180
ctgcccttca gcgaggacat cctgagcgcc ggcttcaagt acggcgaccg gatcttcacc    3240 gagtacccc aggacatcgt ggactacttc aagaacagct gccccgccgg ctacacctgg    3300
ggccggagct tcctgttcga ggacggcgcc gtgtgcatct gtaacgtgga catcaccgtg    3360
agcgtgaagg agaactgcat ctaccacaag agcatcttca acggcgtgaa cttccccgcc    3420 gacggcccg tgatgaagaa gatgaccacc aactgggagg ccagctgcga agagatcatg    3480
cccgtgccta agcagggcat cctgaagggc gacgtgagca tgtacctgct gctgaaggac    3540
ggcggccggt accggtgcca gttcgacacc gtgtacaagg ccaagagcgt gcccagcaag    3600
atgcccgagt ggcacttcat ccagcacaag ctgctgcggg aggaccggag cgacgccaag    3660
aaccagaagt ggcagctgac cgagcacgcc atcgccttcc ccagcgccct ggcctgaagc    3720
ggccgcaacc tagacttgtc catcttctgg attggccaac ttaattaatg tatgaaataa    3780
aaggatgcac acatagtgac atgctaatca ctataatgtg gcatcaaag ttgtgtgtta    3840 tgtgtaatta ctagttatct gaataaaaga gaaagagatc atccatattt cttatcctaa    3900
atgaatgtca cgtgtcttta taattctttg atgaaccaga tgcatttcat taaccaaatc    3960
catatacata taaatattaa tcatatataa ttaatatcaa ttgggttagc aaaacaaatc    4020
tagtctaggt gtgttttgcg aatgcggccg ccaccgcggt ggagctcgaa ttccggtccg    4080
ggcctagaag gccgatctcc cgggcaccca gctttcttgt acaaagtggc cgttaacgga    4140
tcccggtgaa gttcctattc cgaagttcct attctccaga agtataggaa cttcactag    4200 agcttgcggc cgccccgggc aactttatta tacaaagttg ataattcact ggccgtcgtt    4260
ttacaacgtc gtgactggga aaaccctggc gttacccaac ttaatcgcct tgcagcacat    4320
```

```
cccccttttcg ccagctggcg taatagcgaa gaggcccgca ccgatcgccc ttcccaacag   4380
ttgcgcagcc tgaatggcga atggcgcctg atgcggtatt ttctccttac gcatctgtgc   4440
ggtatttcac accgcatatg gtgcactctc agtacaatct gctctgatgc cgcatagtta   4500
agccagcccc gacacccgcc aacacccgct gacgcgccct gacgggcttg tctgctcccg   4560
gcatccgctt acagacaagc tgtgaccgtc tccgggagct gcatgtgtca gaggttttca   4620
ccgtcatcac cgaaacgcgc gagacgaaag gcctcgtgat acgcctattt tttataggtt   4680
aatgtcatga taataatggt ttcttagacg tcaggtggca cttttcgggg aaatgtgcgc   4740
ggaaccccta tttgtttatt tttctaaata cattcaaata tgtatccgct catgagacaa   4800
taaccctgat aaatgcttca ataatattga aaaggaaga gtatgagtat tcaacatttc   4860
cgtgtcgccc ttattccctt ttttgcggca ttttgccttc ctgttttgc tcacccagaa   4920
acgctggtga agtaaaaga tgctgaagat cagttgggtg cacgagtggg ttacatcgaa   4980
ctggatctca acagcggtaa gatccttgag agttttcgcc ccgaagaacg ttttccaatg   5040
atgagcactt ttaaagttct gctatgtggc gcggtattat cccgtattga cgccgggcaa   5100
gagcaactcg gtcgccgcat acactattct cagaatgact tggttgagta ctcaccagtc   5160
acagaaaagc atcttacgga tggcatgaca gtaagagaat tatgcagtgc tgccataacc   5220
atgagtgata acactgcggc caacttactt ctgacaacga tcggaggacc gaaggagcta   5280
accgcttttt tgcacaacat gggggatcat gtaactcgcc ttgatcgttg ggaaccggag   5340
ctgaatgaag ccataccaaa cgacgagcgt gacaccacga tgcctgtagc aatggcaaca   5400
acgttgcgca aactattaac tggcgaacta cttactctag cttcccggca acaattaata   5460
gactggatgg aggcggataa agttgcagga ccacttctgc gctcggccct tccggctggc   5520
tggtttattg ctgataaatc tggagccggt gagcgtgggt ctcgcggtat cattgcagca   5580
ctggggccag atggtaagcc ctcccgtatc gtagttatct acacgacggg gagtcaggca   5640
actatggatg aacgaaatag acagatcgct gagataggtg cctcactgat taagcattgg   5700
taactgtcag accaagttta ctcatatata ctttagattg atttaaaact tcatttttaa   5760
tttaaaagga tctaggtgaa gatcctttt gataatctca tgaccaaaat cccttaacgt   5820
gagttttcgt tccactgagc gtcagacccc gtagaaaaga tcaaaggatc ttcttgagat   5880
ccttttttc tgcgcgtaat ctgctgcttg caaacaaaaa aaccaccgct accagcggtg   5940
gtttgtttgc cggatcaaga gctaccaact cttttttccga aggtaactgg cttcagcaga   6000
gcgcagatac caaatactgt ccttctagtg tagccgtagt taggccacca cttcaagaac   6060
tctgtagcac cgcctacata cctcgctctg ctaatcctgt taccagtggc tgctgccagt   6120
ggcgataagt cgtgtcttac cgggttggac tcaagacgat agttaccgga taaggcgcag   6180
cggtcgggct gaacgggggg ttcgtgcaca cagcccagct tggagcgaac gacctacacc   6240
gaactgagat acctacagcg tgagctatga gaaagcgcca cgcttcccga agggagaaag   6300
gcggacaggt atccggtaag cggcagggtc ggaacaggag agcgcacgag ggagcttcca   6360
gggggaaacg cctggtatct ttatagtcct gtcgggtttc gccacctctg acttgagcgt   6420
cgatttttgt gatgctcgtc aggggggcgg agcctatgga aaaacgccag caacgcggcc   6480
ttttttacggt tcctggcctt ttgctggcct tttgctcaca tgttctttcc tgcgttatcc   6540
cctgattctg tggataaccg tattaccgcc tttgagtgag ctgataccga gcggataaca   6600
atttcaca                                                            6608
```

<210> SEQ ID NO 25
<211> LENGTH: 13906
<212> TYPE: DNA
<213> ORGANISM: Artificial Sequence
<220> FEATURE:
<223> OTHER INFORMATION: transfer cassette plasmid PHP44951
<220> FEATURE:
<221> NAME/KEY: misc_feature
<222> LOCATION: (12482)..(12482)
<223> OTHER INFORMATION: n is a, c, g, or t

<400> SEQUENCE: 25

```
attatacaaa gttgataatt cactggccgt cgttttacaa cgtcgtgact gggaaaaccc      60
tggcgttacc caacttaatc gccttgcagc acatccccct ttcgccagct ggcgtaatag     120
cgaagaggcc cgcaccgatc gcccttccca acagttgcgc agcctgaatg gcgaatggcg     180
cctgatgcgg tattttctcc ttacgcatct gtgcggtatt tcacaccgca tatggtgcac     240
tctcagtaca atctgctctg atgccgcata gttaagccag ccccgacacc cgccaacacc     300
cgctgacgcg ccctgacggg cttgtctgct cccggcatcc gcttacagac aagctgtgac     360
cgtctccggg agctgcatgt gtcagaggtt ttcaccgtca tcaccgaaac gcgcgagacg     420
aaagggcctc gtgatacgcc tatttttata ggttaatgtc atgataataa tggtttctta     480
gacgtcaggt ggcacttttc ggggaaatgt gcgcggaacc cctatttgtt tatttttcta     540
aatacattca aatatgtatc cgctcatgag acaataaccc tgataaatgc ttcaataata     600
ttgaaaaagg aagagtatga gtattcaaca tttccgtgtc gcccttattc ccttttttgc     660
ggcattttgc cttcctgttt ttgctcaccc agaaacgctg gtgaaagtaa agatgctga     720
agatcagttg ggtgcacgag tgggttacat cgaactggat ctcaacagcg gtaagatcct     780
tgagagtttt cgccccgaag aacgttttcc aatgatgagc acttttaaag ttctgctatg     840
tggcgcggta ttatcccgta ttgacgccgg gcaagagcaa ctcggtcgcc gcatacacta     900
ttctcagaat gacttggttg agtactcacc agtcacagaa aagcatctta cggatggcat     960
gacagtaaga gaattatgca gtgctgccat aaccatgagt gataacactg cggccaactt    1020
acttctgaca acgatcggag gaccgaagga gctaaccgct tttttgcaca acatggggga    1080
tcatgtaact cgccttgatc gttgggaacc ggagctgaat gaagccatac caaacgacga    1140
gcgtgacacc acgatgcctg tagcaatggc aacaacgttg cgcaaactat taactggcga    1200
actacttact ctagcttccc ggcaacaatt aatagactgg atggaggcgg ataaagttgc    1260
aggaccactt ctgcgctcgg cccttccggc tggctggttt attgctgata atctggagc    1320
cggtgagcgt gggtctcgcg gtatcattgc agcactgggg ccagatggta agccctcccg    1380
tatcgtagtt atctacacga cggggagtca ggcaactatg gatgaacgaa atagacagat    1440
cgctgagata ggtgcctcac tgattaagca ttggtaactg tcagaccaag tttactcata    1500
tatactttag attgatttaa aacttcattt ttaatttaaa aggatctagg tgaagatcct    1560
ttttgataat ctcatgacca aaatccctta acgtgagttt tcgttccact gagcgtcaga    1620
ccccgtagaa aagatcaaag gatcttcttg agatcctttt tttctgcgcg taatctgctg    1680
cttgcaaaca aaaaaaccac cgctaccagc ggtggtttgt ttgccggatc aagagctacc    1740
aactcttttt ccgaaggtaa ctggcttcag cagagcgcag ataccaaata ctgtccttct    1800
agtgtagccg tagttaggcc accacttcaa gaactctgta gcaccgccta catacctcgc    1860
tctgctaatc ctgttaccag tggctgctgc cagtggcgat aagtcgtgtc ttaccgggtt    1920
ggactcaaga cgatagttac cggataaggc gcagcggtcg ggctgaacgg ggggttcgtg    1980
```

```
cacacagccc agcttggagc gaacgaccta caccgaactg agatacctac agcgtgagct    2040
atgagaaagc gccacgcttc ccgaagggag aaaggcggac aggtatccgg taagcggcag    2100
ggtcggaaca ggagagcgca cgagggagct tccaggggga aacgcctggt atctttatag    2160
tcctgtcggg tttcgccacc tctgacttga gcgtcgattt ttgtgatgct cgtcagggggg    2220
gcggagccta tggaaaaacg ccagcaacgc ggcctttttta cggttcctgg ccttttgctg    2280
gccttttgct cacatgttct ttcctgcgtt atcccctgat tctgtggata accgtattac    2340
cgcctttgag tgagctgata ccgagcggat aacaatttca cacaggaaac agctatgacc    2400
atgattacgc caagctatca actttgtata gaaaagttga agcttcgctg aaatcaccag    2460
tctctctcta caaatctatc tctctctata ataatgtgtg agtagttccc agataaggga    2520
attagggttc ttatagggtt tcgctcatgt gttgagcata taagaaaccc ttagtatgta    2580
tttgtatttg taaaatactt ctatcaataa aatttctaat tcctaaaacc aaaatccagt    2640
ggcgagctgc tagcgaagtt cctattccga agttcctatt ctctagaaag tataggaact    2700
tcagatccac acgacaccat ggctattgag gttaagccta tcaacgcaga ggatacctat    2760
gaccttaggc atagagtgct cagaccaaac cagcctatcg aagcctgcat gtttgagtct    2820
gaccttacta ggagtgcatt tcaccttggt ggattctacg gaggtaaact gatttccgtg    2880
gcttcattcc accaagctga gcactctgaa cttcaaggta agaagcagta ccagcttaga    2940
ggtgtggcta ccttggaagg ttatagagag cagaaggctg ttccagtctc gtgaaacac    3000
gctgaagaga ttctcagaaa gagaggtgct gacatgatct ggtgtaatgc caggacatct    3060
gcttcaggat actacaggaa gttgggattc agtgagcaag gagaggtgtt cgatactcct    3120
ccagttggac ctcacatcct gatgtataag aggatcacat aactagctag tcagttaacc    3180
tagacttgtc catcttctgg attggccaac ttaattaatg tatgaaataa aaggatgcac    3240
acatagtgac atgctaatca ctataatgtg ggcatcaaag ttgtgtgtta tgtgtaatta    3300
ctagttatct gaataaaaga gaaagagatc atccatattt cttatcctaa atgaatgtca    3360
cgtgtcttta taattctttg atgaaccaga tgcatttcat taaccaaatc catatacata    3420
taaatattaa tcatatataa ttaatatcaa ttgggttagc aaaacaaatc tagtctaggt    3480
gtgttttgcg aattgcggcc gggtaccgag ctcgaattcg gcccaagttt gtacaaaaaa    3540
gcaggctccg gccagaatgg cccggaccga agcttgcatg cctgcagtgc agcgtgaccc    3600
ggtcgtgccc ctctctagag ataatgagca ttgcatgtct aagttataaa aaattaccac    3660
atatttttt tgtcacactt gtttgaagtg cagtttatct atcttatac atatatttaa    3720
actttactct acgaataata taatctatag tactacaata atatcagtgt tttagagaat    3780
catataaatg aacagttaga catggtctaa aggacaattg agtattttga caacaggact    3840
ctacagtttt atcttttag tgtgcatgtg ttctccttt tttttgcaaa tagcttcacc    3900
tatataatac ttcatccatt ttattagtac atccatttag ggtttagggt taatggtttt    3960
tatagactaa tttttttagt acatctattt tattctattt tagcctctaa attaagaaaa    4020
ctaaaactct attttagtttt tttatttaa taatttagat ataaaataga ataaaataaa    4080
gtgactaaaa attaaacaaa tacccttaa gaaattaaaa aaactaagga aacatttttc    4140
ttgtttcgag tagataatgc cagcctgtta aacgccgtcg acgagtctaa cggacaccaa    4200
ccagcgaacc agcagcgtcg cgtcgggcca agcgaagcag acggcacggc atctctgtcg    4260
ctgcctctgg acccctctcg agagttccgc tccaccgttg gacttgctcc gctgtcggca    4320
tccagaaatt gcgtggcgga gcggcagacg tgagccggca cggcaggcgg cctcctcctc    4380
```

```
ctctcacggc accggcagct acggggatt ccttccccac cgctccttcg ctttcccttc    4440
ctcgcccgcc gtaataaata gacaccccct ccacaccctc tttccccaac ctcgtgttgt    4500
tcggagcgca cacacacaca accagatctc ccccaaatcc acccgtcggc acctccgctt    4560
caaggtacgc cgctcgtcct cccccccccc cctctctacc ttctctagat cggcgttccg    4620
gtccatgcat ggttagggcc cggtagttct acttctgttc atgtttgtgt tagatccgtg    4680
tttgtgttag atccgtgctg ctagcgttcg tacacggatg cgacctgtac gtcagacacg    4740
ttctgattgc taacttgcca gtgtttctct ttggggaatc ctgggatggc tctagccgtt    4800
ccgcagacgg gatcgatttc atgattttt ttgtttcgtt gcatagggtt tggtttgccc    4860
ttttccttta tttcaatata tgccgtgcac ttgtttgtcg ggtcatcttt tcatgctttt    4920
ttttgtcttg gttgtgatga tgtggtctgg ttgggcggtc gttctagatc ggagtagaat    4980
tctgtttcaa actacctggt ggatttatta attttggatc tgtatgtgtg tgccatacat    5040
attcatagtt acgaattgaa gatgatggat ggaaatatcg atctaggata ggtatacatg    5100
ttgatgcggg ttttactgat gcatatacag agatgctttt tgttcgcttg gttgtgatga    5160
tgtggtgtgg ttgggcggtc gttcattcgt tctagatcgg agtagaatac tgtttcaaac    5220
tacctggtgt atttattaat tttggaactg tatgtgtgtg tcatacatct tcatagttac    5280
gagtttaaga tggatggaaa tatcgatcta ggataggtat acatgttgat gtgggtttta    5340
ctgatgcata tacatgatgg catatgcagc atctattcat atgctctaac cttgagtacc    5400
tatctattat aataaacaag tatgttttat aattattttg atcttgatat acttggatga    5460
tggcatatgc agcagctata tgtggatttt tttagccctg ccttcatacg ctatttattt    5520
gcttggtact gtttctttg tcgatgctca ccctgttgtt tggtgttact tctgcaggtc    5580
gactctagag gatccaccgg tcgccaccat ggcccacagc aagcacggcc tgaaggagga    5640
gatgaccatg aagtaccaca tggagggctg cgtgaacggc cacaagttcg tgatcaccgg    5700
cgagggcatc ggctaccccc tcaagggcaa gcagaccatc aacctgtgcg tgatcgaggg    5760
cggcccctg ccccttcagcg aggacatcct gagcgccggc ttcaagtacg gcgaccggat    5820
cttcaccgag taccccagg acatcgtgga ctacttcaag aacagctgcc ccgccggcta    5880
cacctggggc cggagcttcc tgttcgagga cggcgccgtg tgcatctgta acgtggacat    5940
caccgtgagc gtgaaggaga actgcatcta ccacaagagc atcttcaacg gcgtgaactt    6000
ccccgccgac ggccccgtga tgaagaagat gaccaccaac tgggaggcca gctgcgagaa    6060
gatcatgccc gtgcctaagc agggcatcct gaagggcgac gtgagcatgt acctgctgct    6120
gaaggacggc ggccggtacc ggtgccagtt cgacaccgtg tacaaggcca gagcgtgcc    6180
cagcaagatg cccgagtggc acttcatcca gcacaagctg ctgcgggagg accggagcga    6240
cgccaagaac cagaagtggc agctgaccga gcacgccatc gccttcccca cgcccctggc    6300
ctgaagcggc cgcaacctag acttgtccat cttctggatt ggccaactta attaatgtat    6360
gaaataaaag gatgcacaca tagtgacatg ctaatcacta taatgtgggc atcaaagttg    6420
tgtgttatgt gtaattacta gttatctgaa taaaagagaa agagatcatc catatttctt    6480
atcctaaatg aatgtcacgt gtctttataa ttctttgatg aaccagatgc atttcattaa    6540
ccaaatccat atacatataa atattaatca tatataatta atatcaattg ggttagcaaa    6600
acaaatctag tctaggtgtg ttttgcgaat tgcggccggg taccgagctc gaattcggcc    6660
caagtttgta caaaaaagca ggctccggcc agaatggccc ggaccgggtt accgaattcg    6720
```

-continued

```
agctcggtac cctgggatcg gccgcggacc gaattatcga attcctgcag cccatccctc    6780
agccgccttt cactatcttt tttgcccgag tcattgtcat gtgaaccttg gcatgtataa    6840
tcggtgaatt gcgtcgattt tcctcttata ggtgggccaa tgaatccgtg tgatcgcgtc    6900
tgattggcta gagatatgtt tcttccttgt tggatgtatt ttcatacata atcatatgca    6960
tacaaatatt tcattacact ttatagaaat ggtcagtaat aaaccctatc actatgtctg    7020
gtgtttcatt ttatttgctt ttaaacgaaa attgacttcc tgattcaata tttaaggatc    7080
gtcaacggtg tgcagttact aaattctggt ttgtaggaac tatagtaaac tattcaagtc    7140
ttcacttatt gtgcactcac ctctcgccac atcaccacag atgttattca cgtcttaaat    7200
ttgaactaca catcatattg acacaatatt tttttttaaat aagcgattaa aacctagcct   7260
ctatgtcaac aatggtgtac ataaccagcg aagtttaggg agtaaaaaac atcgccttac    7320
acaaagttcg ctttaaaaaa taagagtaaa attttacttt ggaccaccct tcaaccaatg    7380
tttcactttta gaacgagtaa ttttattatt gtcactttgg accaccctca aatctttttt    7440
ccatctacat ccaatttatc atgtcaaaga aatggtctac atacagctaa ggagatttat    7500
cgacgaatag tagctagcat actcgaggtc attcatatgc ttgagaagag agtcgggata    7560
gtccaaaata aaacaaaggt aagattacct ggtcaaaagt gaaaacatca gttaaaaggt    7620
ggtataaagt aaaatatcgg taataaaagg tggcccaaag tgaaatttac tcttttctac    7680
tattataaaa attgaggatg tttttgtcgg tactttgata cgtcattttt gtatgaattg    7740
gtttttaagt ttattcgctt ttggaaatgc atatctgtat ttgagtcggg ttttaagttc    7800
gtttgctttt gtaaatacag agggatttgt ataagaaata tctttaaaaa aacccatatg    7860
ctaatttgac ataattttttg agaaaaatat atattcaggc gaattctcac aatgaacaat    7920
aataagatta aaatagcttt ccccgttgc agcgcatggg tatttttctt agtaaaaata    7980
aaagataaac ttagactcaa aacatttaca aaaacaaccc ctaaagttcc taaagcccaa    8040
agtgctatcc acgatccata gcaagccccag cccaacccaa cccaacccaa cccacccag    8100
tccagccaac tggacaatag tctccacacc ccccccacta tcaccgtgagt tgtccgcacg   8160
caccgcacgt ctcgcagcca aaaaaaaaaa aagaaagaaa aaaagagaaa agaaaaaaca    8220
gcaggtgggt ccgggtcgtg ggggccggaa acgcgaggag gatcgcgagc cagcgacgag    8280
gccgcccctc cctccgcttc caaagaaacg ccccccatcg ccactatata catcccccc     8340
cctctcctcc catcccccca accctaccac caccaccacc accacctcca cctcctcccc    8400
cctcgctgcc ggacgacgag ctcctcccccc ctccccctcc gccgccgccg cgccggtaac   8460
caccccgccc ctctcctctt tctttctccg tttttttttt ccgtctcggt ctcgatcttt    8520
ggccttggta gtttgggtgg gcgagaggcg gcttcgtgcg cgcccagatc ggtgcgcggg    8580
agggcggga tctcgcggct ggggctctcg ccggcgtgga tcaggcccgg atctcgcggg     8640
gaatggggct ctcggatgta gatctgcgat ccgccgttgt tggggagat gatgggggt     8700
ttaaaatttc cgccatgcta aacaagatca ggaagagggg aaaagggcac tatggtttat    8760
atttttatat atttctgctg cttcgtcagg cttagatgtg ctagatcttt cttctcttctt    8820
tttgtgggta gaatttgaat ccctcagcat tgttcatcgg tagttttttct tttcatgatt   8880
tgtgacaaat gcagcctcgt gcggagcttt tttgtaggta aaggatcca tggtccgtcc     8940
tgtagaaacc ccaacccgtg aaatcaaaaa actcgacggc ctgtgggcat tcagtctgga    9000
tcgcgaaaac tgtggaattg atcagcgttg gtgggaaagc gcgttacaag aaagccgggc    9060
aattgctgtg ccaggcagtt ttaacgatca gttcgccgat gcagatattc gtaattatgc    9120
```

```
gggcaacgtc tggtatcagc gcgaagtctt tataccgaaa ggttgggcag gccagcgtat    9180
cgtgctgcgt ttcgatgcgg tcactcatta cggcaaagtg tgggtcaata atcaggaagt    9240
gatggagcat cagggcggct atacgccatt tgaagccgat gtcacgccgt atgttattgc    9300
cgggaaaagt gtacgtatca ccgtttgtgt gaacaacgaa ctgaactggc agactatccc    9360
gccgggaatg gtgattaccg acgaaaacgg caagaaaaag cagtcttact tccatgattt    9420
ctttaactat gccggaatcc atcgcagcgt aatgctctac accacgccga acacctgggt    9480
ggacgatatc accgtggtga cgcatgtcgc gcaagactgt aaccacgcgt ctgttgactg    9540
ccaggtggtg gccaatggtg atgtcagcgt tgaactgcgt gatgcggatc aacaggtggt    9600
tgcaactgga caaggcacta gcgggacttt gcaagtggtg aatccgcacc tctgccaacc    9660
gggtgaaggt tatctctatg aactgtgcgt cacagccaaa agccagacag agtgtgatat    9720
ctacccgctt cgcgtcggca tccggtcagt ggcagtgaag ggccaacagt tcctgattaa    9780
ccacaaaccg ttctacttta ctggctttgg tcgtcatgaa gatgcggact acgtggcaa    9840
aggattcgat aacgtgctga tggtgcacga ccacgcatta atggactgga ttggggccaa    9900
ctcctaccgt acctcgcatt acccttacgc tgaagagatg ctcgactggg cagatgaaca    9960
tggcatcgtg gtgattgatg aaactgctgc tgtcggcttt aacctctctt taggcattgg   10020
tttcgaagcg ggcaacaagc cgaaagaact gtacagcgaa gaggcagtca acggggaaac   10080
tcagcaagcg cacttacagg cgattaaaga gctgatagcg cgtgacaaaa accacccaag   10140
cgtggtgatg tggagtattg ccaacgaacc ggatacccgt ccgcaagtgc acgggaatat   10200
ttcgccactg gcggaagcaa cgcgtaaact cgacccgacg cgtccgatca cctgcgtcaa   10260
tgtaatgttc tgcgacgctc acaccgatac catcagcgat ctctttgatg tgctgtgcct   10320
gaaccgttat tacggatggt atgtccaaag cggcgatttg gaaacggcag agaaggtact   10380
ggaaaaagaa cttctggcct ggcaggagaa actgcatcag ccgattatca tcaccgaata   10440
cggcgtggat acgttagccg ggctgcactc aatgtacacc gacatgtgga gtgaagagta   10500
tcagtgtgca tggctggata tgtatcaccg cgtctttgat cgcgtcagcg ccgtcgtcgg   10560
tgaacaggta tggaatttcg ccgattttgc gacctcgcaa ggcatattgc gcgttggcgg   10620
taacaagaaa gggatcttca ctcgcgaccg caaaccgaag tcggcggctt ttctgctgca   10680
aaaacgctgg actggcatga acttcggtga aaaaccgcag cagggaggca acaatgaat   10740
caacaactct cctggcgcac catcgtcggc tacagcctcg gtgacgtggg aattgcaacc   10800
tagacttgtc catcttctgg attggccaac ttaattaatg tatgaaataa aaggatgcac   10860
acatagtgac atgctaatca ctataatgtg ggcatcaaag ttgtgtgtta tgtgtaatta   10920
ctagttatct gaataaaaga gaagagatc atccatattt cttatcctaa atgaatgtca   10980
cgtgtcttta taattctttg atgaaccaga tgcatttcat taaccaaatc catatacata   11040
taaatattaa tcatatataa ttaatatcaa ttgggttagc aaaacaaatc tagtctaggt   11100
gtgttttgcg aattcccatg gacctcgagg ggggcccgg gcacccagct tcttgtaca    11160
aagtggccgt taacggatcg ctgtttaaac gctcttcaac tggaagagcg gttaccagag   11220
ctggtcacct ttgtccacca agatggaact gcggccgctc attaattaag tcaggcgcgc   11280
ctctagttga agacacgttc atgtcttcat cgtaagaaga cactcagtag tcttcggcca   11340
gaatggccat ctggattcag caggcctaga aggccattta atcctgagg atctggtctt   11400
cctaaggacc cgggatatcg gaccgaagct aattcctgca gtgcagcgtg acccggtcgt   11460
```

```
gcccctctct agtggatctg agcttctaga aatccgtcaa catggtggag cacgacactc   11520
tcgtctactc caagaatatc aaagatacag tctcagaaga ccaaagggct attgagactt   11580
ttcaacaaag ggtaatatcg ggaaacctcc tcggattcca ttgcccagct atctgtcact   11640
tcatcaaaag gacagtagaa aaggaaggtg gcacctacaa atgccatcat tgcgataaag   11700
gaaaggctat cgttcaagat gcctctgccg acagtggtcc caaagatgga cccccaccca   11760
cgaggagcat cgtggaaaaa gaagacgttc caaccacgtc ttcaaagcaa gtggattgat   11820
gtgatgctct agaaatccgt caacatggtg gagcacgaca ctctcgtcta ctccaagaat   11880
atcaaagata cagtctcaga agaccaaagg gctattgaga cttttcaaca aagggtaata   11940
tcgggaaacc tcctcggatt ccattgccca gctatctgtc acttcatcaa aaggacagta   12000
gaaaaggaag gtggcaccta caaatgccat cattgcgata aaggaaaggc tatcgttcaa   12060
gatgcctctg ccgacagtgg tcccaaagat ggaccccac ccacgaggag catcgtggaa   12120
aaagaagacg ttccaaccac gtcttcaaag caagtggatt gatgtgatat ctccactgac   12180
gtaagggatg acgcacaatc ccactatcct tcgcaagacc cttcctctat ataaggaagt   12240
tcatttcatt tggagaggac gagctgcagg tcgacggatc aagtgcaaag gtccgccttg   12300
tttctcctct gtctcttgat ctgactaatc ttggtttatg attcgttgag taattttggg   12360
gaaagcttcg tccacagttt ttttttcgat gaacagtgcc gcagtggcgc tgatcttgta   12420
tgctatcctg caatcgtggt gaacttatgt cttttatatc cttcactacc atgaaaagac   12480
tngtaatctt tctcgatgta acatcgtcca gcactgctat taccgtgtgg tccatccgac   12540
agtctggctg aacacatcat acgatattga gcaaagatcg atctatcttc cctgttcttt   12600
aatgaaagac gtcattttca tcagtatgat ctaagaatgt tgcaacttgc aaggaggcgt   12660
ttctttcttt gaatttaact aactcgttga gtggccctgt ttctcggacg taaggccttt   12720
gctgctccac acatgtccat tcgaatttta ccgtgtttag caagggcgaa aagtttgcat   12780
cttgatgatt tagcttgact atgcgattgc tttcctggac ccgtgcagct gcggacggat   12840
ccacacgaca ccatgtcccc cgagcgccgc cccgtcgaga tccgcccggc caccgccgcc   12900
gacatggccg ccgtgtgcga catcgtgaac cactacatcg agacctccac cgtgaacttc   12960
cgcaccgagc cgcagacccc gcaggagtgg atcgacgacc tggagcgcct ccaggaccgc   13020
tacccgtggc tcgtggccga ggtggagggc gtggtggccg gcatcgccta cgccggcccg   13080
tggaaggccc gcaacgccta cgactggacc gtggagtcca ccgtgtacgt gtcccaccgc   13140
caccagcgcc tcggcctcgg ctccacccct tacacccacc tcctcaagag catggaggcc   13200
cagggcttca agtccgtggt ggccgtgatc ggcctcccga acgacccgtc cgtgcgcctc   13260
cacgaggccc tcggctacac cgcccgcggc accctccgcg ccgccggcta caagcacggc   13320
ggctggcacg acgtcggctt ctggcagcgc gacttcgagc tgccggcccc gccgcgcccg   13380
gtgcgcccgg tgacgcagat ctgagtcgaa acctagactt gtccatcttc tggattggcc   13440
aacttaatta atgtatgaaa taaaaggatg cacacatagt gacatgctaa tcactataat   13500
gtgggcatca agttgtgtg ttatgtgtaa ttactagtta tctgaataaa agagaaagag   13560
atcatccata tttcttatcc taaatgaatg tcacgtgtct ttataattct ttgatgaacc   13620
agatgcattt cattaaccaa atccatatac atataaatat taatcatata taattaatat   13680
caattgggtt agcaaaacaa atctagtcta ggtgtgtttt gcgaattgcg gccgccaccg   13740
cggtggagct cgaattcatt ccgattaatc gtggcctctt gctcttcagg atgaagagct   13800
atgtttaaac gtgcaagcga tcccggtgaa gttcctattc cgaagttcct attctccaga   13860
```

-continued

```
aagtatagga acttcactag agcttgcggc cgccccgggc aacttt                  13906
```

<210> SEQ ID NO 26
<211> LENGTH: 1272
<212> TYPE: DNA
<213> ORGANISM: Artificial Sequence
<220> FEATURE:
<223> OTHER INFORMATION: Plant-optimized nucleotide sequence of TS14
      meganuclease

<400> SEQUENCE: 26

```
atggcaccga agaagaagcg caaggtgcat atgaacacca agtacaacaa ggagttcctg     60
ctctacctgg ccggcttcgt ggacggcgac ggctccatca tcgcgtccat caagccggag    120
cagtcctaca agttcaagca ccgcctctcc ctgaccttca ccgtgaccca gaagacgcag    180
aggcgctggt tcctcgacaa gctggtcgac gagatcgggg tgggcaaggt ctacgaccgc    240
gggtcggtgt ccgactaccg cctctcccag atcaagcccc tgcacaactt cctcacccag    300
ctccagccgt tcctgaagct caagcagaag caggccaacc tcgtgctgaa gatcatcgag    360
cagctgccct ccgccaagga atccccggac aagttcctgg aggtaagttt ctgcttctac    420
ctttgatata tatataataa ttatcattaa ttagtagtaa tataatattt caaatatttt    480
tttcaaaata aaagaatgta gtatatagca attgcttttc tgtagtttat aagtgtgtat    540
attttaattt ataactttc taatatatga ccaaaacatg gtgatgtgca ggtgtgcacg    600
tgggtggacc agatcgcggc cctcaacgac agcaagaccc gcaagacgac ctcggagacg    660
gtgcgggcgg tcctggactc cctcccagga tccgtgggag gtctatcgcc atctcaggca    720
tccagcgccg catcctcggc ttcctcaagc ccggttcag ggatctccga agcactcaga    780
gctggagcaa ctaagtccaa ggaattcctg ctctacctgg ccggcttcgt ggacggcgac    840
ggctccatca tcgcgaagat caccccgaac cagtcctaca agttcaagca ccagctccag    900
ctgcgcttca ccgtgaccca gaagacgcag aggcgctggt tcctcgacaa gctggtcgac    960
gagatcgggg tgggcaaggt ctacgaccgc gggtcggtgt ccgactacat cctctcccag   1020
atcaagcccc tgcacaactt cctcacccag ctccagccgt tcctcaagct gaagcagaag   1080
caggcgaacc tcgtcctgaa gatcatcgag cagctcccct cggccaagga gtccccggac   1140
aagttcctgg aggtgtgcac gtgggtcgac cagatcgcgg ccctcaacga cagcaagacc   1200
cgcaagacga cctcggagac ggtgcgggcg gttctagact ccctcagcga agaagaag    1260
tcgtccccct ga                                                        1272
```

<210> SEQ ID NO 27
<211> LENGTH: 3370
<212> TYPE: DNA
<213> ORGANISM: Artificial Sequence
<220> FEATURE:
<223> OTHER INFORMATION: RTW347

<400> SEQUENCE: 27

```
ccgggtgatt gcggttacat catgtacgga aaaataattc taatccttga tttaaatttg     60
aacttgacta tttatttatt ctttatttca ttttgtaaat cattttatgt atctcctggc    120
aagcaatttt atccaccttg caccaacacc ttcgggttcc ataatcaaac caccttaact    180
tcacaccatg ctgtaactca caccgccag catctccaat gtgaaagaag ctaaattta    240
ataaacaatc atacgaagca gtgacaaaat accagatggt attaatgctt cgataaaatt    300
aattggaaag tataaaatgg tagaaaataa taaattataa ttaatttaag taagataaaa    360
```

```
aataattaaa aactaaaatg ttaaaatttt aaaaaaatta ttttaaataa tatttaaaaa    420
cattaaaaat cattttaaaa aatttattta tagaacaatt aaataaatat ttcagctaat    480
aaaaaacaaa agcttaccta gccttagaag acaacttgtc caacaattag atgataccca    540
ttgcccttac gttttctta acatcaatta ttgttttttgt caacaagcta tcttttagtt    600
ttatttattt ggtaaaaaat atgtcgcctt caagttgcat catttaacac atctcgtcat    660
tagaaaaata aaactcttcc ctaaacgatt agtagaaaaa atcattcgat aataaataag    720
aaagaaaaat tagaaaaaaa taacttcatt ttaaaaaaat cattaaggct atattttta    780 aatgactaat tttatataga ctgtaactaa aagtatacaa tttattatgc tatgtatctt    840
aaagaattac ttataaaaat ctacggaaga atatcttaca aagtgaaaaa caaatgagaa    900
agaatttagt gggatgatta tgattttatt tgaaaattga aaaataatt attaaagact    960 ttagtggagt aagaaagctt tcctattagt cttttcttat ccataaaaaa aaaaaaaaaa   1020
atctagcgtg acagcttttc catagatttt aataatgtaa aatactggta gcagccgacc   1080
gttcaggtaa tggacactgt ggtcctaact tgcaacgggt gcgggcccaa tttaataacg   1140
ccgtggtaac ggataaagcc aagcgtgaag cggtgaaggt acatctctga ctccgtcaag   1200
attacgaaac cgtcaactac gaaggactcc ccgaaatatc atctgtgtca taaacaccaa   1260
gtcacaccat acatgggcac gcgtcacaat atgattggag aacggttcca ccgcatatgc   1320
tataaaatgc ccccacaccc ctcgaccta atcgcacttc aattgcaatc aaattagttc   1380
attctctttg cgcagttccc tacctctcct ttcaaggttc gtagatttct tccgtttttt   1440
tttcttcttc tttattgttt gttctacatc agcatgatgt tgatttgatt gtgttttcta   1500
tcgtttcatc gattataaat tttcataatc agaagattca gcttttatta atgcaagaac   1560
gtccttaatt gatgattta aaccgtaaa ttaggtctaa ttagagtttt tttcataaag   1620
attttcagat ccgtttacaa caagccttaa ttgttgattc tgtagtcgta gattaaggtt   1680
tttttcatga actacttcag atccgttaaa caacagcctt atttgttgat acttcagtcg   1740
tttttcaaga aattgttcag atccgttgat aaaagcctta ttcgttgatt ctgtatggta   1800
tttcaagaga tattgctcag gtcctttagc aactaccta ttgttgatt ctgtggccat   1860 agattaggat ttttttcac gaaattgctt cttgaaatta cgtgatggat tttgattctg   1920 attatcttg tgattgttga ctctacagcc atggcaccga agaagaagcg caaggtgcat   1980
atgaacacca gtacaacaa ggagttcctg ctctacctgg ccggcttcgt ggacggcgac   2040
ggctccatca tcgcgtccat caagccggag cagtcctaca gttcaagca ccgcctctcc   2100 ctgaccttca ccgtgaccca gaagacgcag aggcgctggt tcctcgacaa gctggtcgac   2160
gagatcgggg tgggcaaggt ctacgaccgc gggtcggtgt ccgactaccg cctctcccag   2220
atcaagcccc tgcacaactt cctcacccag ctccagccgt tcctgaagct caagcagaag   2280
caggccaacc tcgtgctgaa gatcatcgag cagctgccct ccgccaagga tccccggac   2340 aagttcctgg aggtgtgcac gtgggtggac cagatcgcgg ccctcaacga cagcaagacc   2400
cgcaagacga cctcggagac ggtgcgggcg gtcctggact ccctcccagg atccgtggga   2460
ggtctatcgc catctcaggc atccagcgcc gcatcctcgg cttcctcaag cccgggttca   2520
gggatctccg aagcactcag agctggagca actaagtcca aggaattcct gctctacctg   2580
gccggcttcg tggacggcga cggctccatc atcgcgaaga tcaccccgaa ccagtcctac   2640
aagttcaagc accagctcca gctgcgcttc accgtgaccc agaagacgca gaggcgctgg   2700
```

-continued

```
ttcctcgaca agctggtcga cgagatcggg gtgggcaagg tctacgaccg cgggtcggtg    2760
tccgactaca tcctctccca gatcaagccc ctgcacaact tcctcaccca gctccagccg    2820
ttcctcaagc tgaagcagaa gcaggcgaac ctcgtcctga gatcatcga gcagctcccc     2880 tcggccaagg agtccccgga caagttcctg gaggtgtgca cgtgggtcga ccagatcgcg    2940
gccctcaacg acagcaagac ccgcaagacg acctcggaga cggtgcgggc ggttctagac    3000
tccctcagcg agaagaagaa gtcgtccccc tgaggtacca catggttaac ctagacttgt    3060
ccatcttctg gattggccaa cttaattaat gtatgaaata aaaggatgca cacatagtga    3120
catgctaatc actataatgt gggcatcaaa gttgtgtgtt atgtgtaatt actagttatc    3180
tgaataaaag agaaagagat catccatatt tcttatccta aatgaatgtc acgtgtcttt    3240
ataattcttt gatgaaccag atgcatttca ttaaccaaat ccatatacat ataaatatta    3300
atcatatata attaatatca attgggttag caaaacaaat ctagtctagg tgtgttttgc    3360
gaatgcggcc                                                          3370
```

<210> SEQ ID NO 28
<211> LENGTH: 6691
<212> TYPE: DNA
<213> ORGANISM: Artificial Sequence
<220> FEATURE:
<223> OTHER INFORMATION: RTW365

<400> SEQUENCE: 28

```
tcgagatttt gtcagtcttg taactttga aacttttttt tcttttttt atagaccaat      60 aatataatat attatattaa aaaaaccaaa cttataacaa catgtaacac gttagcaaac    120
agtagatctc aaccaaacgt tcgaaaactt ttggatatta tatatgtggc tgttggcact    180
gctaaactca gcagtatatc tccattattg atgagtctct cctaaaatta tctttccaag    240 tcttatttt tatttaattg gttagatatt aaattgaaaa ataaaataaa agttgtgttg    300
ttgtgtagtt ttcgtcactt ttactcataa gaaaatatat atactacgtt tagcatcttt    360
aaactgaaaa cttttcagtt gaaatgcata acaaatatt ggccaagtaa ttagtacaca    420
aaatcttgct caaagtgttt gccaccatag atttaggttg tgtttaggac gattacttaa    480
aatatcatta attgataatt gaacttcaa ataaaattta aaagttttaaa agttgaatag    540 ttaaaaatga aagctgaaaa taaataagct aatggattca atttgaagta tttaatagta    600
tcaactagtg aaatttattc ataaattctc ttttaaatat ataccgattt tattagttaa    660 tataaaaaa aaatagtatg aactaataaa attgatcaaa agtaaattaa tataaatata    720
aaattttata tgatgaataa tcagtagaaa taataaaaaa gttagctcta gaaaagataa    780
attgatttaa ttagggtcat gacaaaattt tgctagcttc tatttagtc tgctttgctt    840 tagaatattt acattcaaat agctctttta tagcataaca aacataaaaa aagctattga    900
ttctacataa aaaaaaaga ttaattatgc tattctttgg gacaaaactt ttagatgaat    960 gccaattta aataattatt aaggtattca agcagacgta cgcaagtcga gtaatactag    1020
tggtcaccta agtgactagg gtcacgtgac cctagtcact tattcccggg taccgagctc    1080
actagacgcg gtgaaattac ctaattaaca ccggtgttta acactagta acggccgcca    1140 gtgtgctgga attcgcccctt cccaagcttt gctctagatc aaactcacat ccaaacataa   1200
catggatatc ttccttacca atcatactaa ttattttggg ttaaatatta atcattattt    1260
ttaagatatt aattaagaaa ttaaaagatt ttttaaaaaa atgtataaaa ttatattatt    1320
catgattttt catacatttg atttgataa taaatatatt ttttttaatt tcttaaaaaa    1380
```

```
tgttgcaaga cacttattag acatagtctt gttctgttta caaaagcatt catcatttaa    1440
tacattaaaa aatatttaat actaacagta gaatcttctt gtgagtggtg tgggagtagg    1500
caacctggca ttgaaacgag agaaagagag tcagaaccag aagacaaata aaaagtatgc    1560
aacaaacaaa tcaaaatcaa agggcaaagg ctggggttgg ctcaattggt tgctacattc    1620
aattttcaac tcagtcaacg gttgagattc actctgactt ccccaatcta agccgcggat    1680
gcaaacggtt gaatctaacc cacaatccaa tctcgttact taggggcttt tccgtcatta    1740 actcaccect gccacccggt ttccctataa attggaactc aatgctcccc tctaaactcg    1800
tatcgcttca gagttgagac caagacacac tcgttcatat atctctctgc tcttctcttc    1860
tcttctacct ctcaaggtac ttttcttctc cctctaccaa atcctagatt ccgtggttca    1920
atttcggatc ttgcacttct ggtttgcttt gccttgcttt ttcctcaact gggtccatct    1980
aggatccatg tgaaactcta ctctttcttt aatatctgcg gaatacgcgt tggactttca    2040
gatctagtcg aaatcatttc ataattgcct ttctttcttt tagcttatga gaaataaaat    2100 cactttttt ttatttcaaa ataaaccttg ggccttgtgc tgactgagat ggggtttggt    2160
gattacagaa tttagcgaa ttttgtaatt gtacttgttt gtctgtagtt ttgtttgtt    2220 ttcttgtttc tcatacattc cttaggcttc aatttattc gagtataggt cacaatagga    2280
attcaaactt tgagcagggg aattaatccc ttccttcaaa tccagtttgt ttgtatatat    2340
gtttaaaaaa tgaaactttt gctttaaatt ctattataac ttttttatg gctgaaattt    2400 ttgcatgtgt ctttgctctc tgttgtaaat ttactgttta ggtactaact ctaggcttgt    2460
tgtgcagttt ttgaagtata acaacagaag ttcctattcc gaagttccta ttctctagaa    2520
agtataggaa cttccaccac acaacacaat ggcggccacc gcttccagaa ccacccgatt    2580
ctcttcttcc tcttcacacc ccaccttccc caaacgcatt actagatcca ccctccctct    2640
ctctcatcaa accctcacca aacccaacca cgctctcaaa atcaaatgtt ccatctccaa    2700
accccccacg gcggcgccct tcaccaagga agcgccgacc acggagccct tcgtgtcacg    2760
gttcgcctcc ggcgaacctc gcaagggcgc ggacatcctt gtggaggcgc tggagaggca    2820
gggcgtgacg acggtgttcg cgtacccegg cggtgcgtcg atggagatcc accaggcgct    2880
cacgcgctcc gccgccatcc gcaacgtgct cccgcgccac gagcagggcg gcgtcttcgc    2940
cgccgaaggc tacgcgcgtt cctccggcct ccccggcgtc tgcattgcca cctccggccc    3000
cggcgccacc aacctcgtga gcggcctcgc cgacgcttta atggacagcg tcccagtcgt    3060
cgccatcacc ggccaggtcg cccgccggat gatcggcacc gacgccttcc aagaaacccc    3120
gatcgtggag gtgagcagat ccatcacgaa gcacaactac ctcatcctcg acgtcgacga    3180
catcccccgc gtcgtcgccg aggctttctt cgtcgccacc tccggccgcc ccggtccggt    3240
cctcatcgac attcccaaag acgttcagca gcaactcgcc gtgcctaatt gggacgagcc    3300
cgttaacctc cccggttacc tcgccaggct gccaggcccc ccgccgagg cccaattgga    3360 acacattgtc agactcatca tggaggccca aaagcccgtt ctctacgtcg gcggtggcag    3420
tttgaattcc agtgctgaat tgaggcgctt tgttgaactc actggtattc ccgttgctag    3480
cactttaatg ggtcttggaa cttttcctat tggtgatgaa tattcccttc agatgctggg    3540
tatgcatggt actgtttatg ctaactatgc tgttgacaat agtgatttgt tgcttgcctt    3600
tggggtaagg tttgatgacc gtgttactgg gaagcttgag gcttttgcta gtagggctaa    3660
gattgttcac attgatattg attctgccga gattgggaag aacaagcagg cgcacgtgtc    3720
```

```
ggtttgcgcg gatttgaagt tggccttgaa gggaattaat atgattttgg aggagaaagg    3780
agtggagggt aagtttgatc ttggaggttg gagagaagag attaatgtgc agaaacacaa    3840
gtttccattg ggttacaaga cattccagga cgcgatttct ccgcagcatg ctatcgaggt    3900
tcttgatgag ttgactaatg gagatgctat tgttagtact ggggttgggc agcatcaaat    3960
gtgggctgcg cagttttaca agtacaagag accgaggcag tggttgacct caggggqtct    4020 tggagccatg ggttttggat tgcctgcggc tattggtgct gctgttgcta acccctggggc    4080 tgttgtggtt gacattgatg gggatggtag tttcatcatg aatgttcagg agttggccac    4140
tataagagtg gagaatctcc cagttaagat attgttgttg aacaatcagc atttgggtat    4200
ggtggttcag ttggaggata ggttctacaa gtccaataga gctcacacct atcttggaga    4260
tccgtctagc gagagcgaga tattcccaaa catgctcaag tttgctgatg cttgtgggat    4320
accggcagcg cgagtgacga agaaggaaga gcttagagcg gcaattcaga gaatgttgga    4380 caccccctggc ccctaccttc ttgatgtcat tgtgccccat caggagcatg tgttgccgat    4440
gattcccagt aatggatcct tcaaggatgt gataactgag ggtgatggta gaacgaggta    4500
ctgattgcct agaccaaatg ttccttgatg cttgttttgt acaatatata taagataatg    4560
ctgtcctagt tgcaggattt ggcctgtggt gagcatcata gtctgtagta gttttggtag    4620
caagacattt tattttcctt ttatttaact tactacatgc agtagcatct atctatctct    4680
gtagtctgat atctcctgtt gtctgtattg tgccgttgga ttttttgctg tagtgagact    4740
gaaaatgatg tgctagtaat aatatttctg ttagaaatct aagtagagaa tctgttgaag    4800
aagtcaaaag ctaatggaat caggttacat attcaatgtt tttctttttt tagcggttgg    4860
tagacgtgta gattcaactt ctcttggagc tcacctaggc aatcagtaaa atgcatattc    4920
cttttttaac ttgccattta tttacttta gtggaaattg tgaccaattt gttcatgtag    4980
aacggatttg gaccattgcg tccacaaaac gtctcttttg ctcgatcttc acaaagcgat    5040
accgaaatcc agagatagtt ttcaaaagtc agaaatggca aagttataaa tagtaaaaca    5100
gaatagatgc tgtaatcgac ttcaataaca agtggcatca cgtttctagt tctagaccca    5160
tcagctgggc cggcccagct gatgatcccg gtgaagttcc tattccgaag ttcctattct    5220
ccagaaagta taggaacttc actagagctt gcggccgcgc atgctgactt aatcagctaa    5280
cgccactcga cctgcaggca tgcccgcgga tatcgatggg ccccggccga agcttcaagt    5340
ttgtacaaaa aagcaggctc cggccagaat ccggtaagtg actagggtca cgtgacccta    5400
gtcacttaaa ttcggccaga atggccatct ggattcagca ggcctagaag gcccggaccg    5460
attaaacttt aattcggtcc ggaagcttgg atccgtcgac gaattcacta gtgttaccag    5520
agctggtcac ctaagtgact agggtcacgt gaccctagtc acttattccc ggcacccag    5580 cttttcttgta caaagtggcc gttaacggat cggccagaat ccggtaagtg actagggtca    5640
cgtgacccta gtcacttaaa ttcggccaga atggccatct ggattcagca ggcctagaag    5700
gcccggaccg attaaacttt aattcggtcc gggttacctc tagaaagctt gtcgacctgc    5760
aggcaagtag cttgttact ttcgtattga caattcaaaa tcgtctttta ttttattttt    5820
gttttgttta attagaggac tttttgaagt cgtccatcat gtgttctta ttttgtcagt    5880 tttgtcactt atgaacactt tttttacaga caaataatat attatattaa aaaaaccata    5940
cttataacaa caacatgtaa cacgttggca aacagttaat ctcaaccaaa cgctcgaaaa    6000
cttttggata ttatatatat atatgcatgg ctattggcag tgctaaagtc atcattatca    6060
ttctaaagtc atcagtatca ttctaattct catattgagt ggattcattt catcaatcac    6120
```

-continued

```
tttgcctttc tcatcataac caccaaaatg ccaaccatta atccagttgg tttgaaattc    6180
atggaaggca taataacatt tatgatgatg atgttgcagg ttgttgtttc tgctcaagac    6240
catattatgt gcattcagac tgagagagaa gcactcctcc aattcaaggc tgcacttctg    6300
gatcactatg gcatgctctc ttcttggacc acttctgatt gctgccaatg caagggatt    6360 cgctgctcca acctcaccgc ccatgttcta atgctcgacc ttcacagttt aggcctcaga    6420
ggagagatcc accagtcgtt gatggagttg caacaattaa actatttaaa cctcagttgg    6480
aattcttttc aaggcagagg aatcccagag tttcttggtt ctctcaccaa cttgagatac    6540
cttgatctgt cacattctga ttttgaagga aaaattccaa ctcagtttgg ctctcttttct   6600 catttgaaat acttaaatct tgctgggaat tattatctgg agggttcaat cccacgtcaa    6660
cttggaaatc tctcccagtt gcagcatctt g                                   6691
```

<210> SEQ ID NO 29
<211> LENGTH: 27
<212> TYPE: DNA
<213> ORGANISM: Artificial Sequence
<220> FEATURE:
<223> OTHER INFORMATION: WOL192 primer sequence

<400> SEQUENCE: 29

```
gtacgcaaac agcttgttta cctttcg                                          27
```

<210> SEQ ID NO 30
<211> LENGTH: 28
<212> TYPE: DNA
<213> ORGANISM: Artificial Sequence
<220> FEATURE:
<223> OTHER INFORMATION: WOL311 primer sequence

<400> SEQUENCE: 30

```
agtatgattg gtaaggaaga tatccatg                                         28
```

<210> SEQ ID NO 31
<211> LENGTH: 1334
<212> TYPE: DNA
<213> ORGANISM: Artificial Sequence
<220> FEATURE:
<223> OTHER INFORMATION: PCR product with WOL192 and WOL311

<400> SEQUENCE: 31

```
gtacgcaaac agcttgttta cctttcgtat tcacaattca aagtcgtctt ttgtttattt      60
atttattttt gaatcagaga acttttttgaa gtcgtcgatc atgttttttca tattttgtca   120 gtcttgtaac ttttgaaaac ttttttttctt tttttttatag accaataata taatatatta   180
tattaaaaaa accaaactta taacaacatg taacacgtta gcaaacagta gatctcaacc    240
aaacgttcga aaacttttgg atattatata tgtggctgtt ggcactgcta aactcagcag    300
tatatctcca ttattgatga gtctctccta aaattatctt tccaagtctt atttttttatt    360 taattggtta gatattaaat tgaaaaataa aataaaagtt gtgttgttgt gtagttttcg    420
tcacttttac tcataagaaa atatatatac tacgtttagc atctttaaac tgaaaacttt   480
tcagttgaaa tgcataacaa atattggcc aagtaattag tacacaaaat cttgctcaaa    540
gtgtttgcca ccatagattt aggttgtgtt taggacgatt acttaaaata tcattaattg    600
ataattgaaa cttcaaataa aatttaaaag tttaaaagtt gaatagttaa aaatgaaagc    660
tgaaaataaa taagctaatg gattcaattt gaagtattta atagtatcaa ctagtgaaat    720
```

```
ttattcataa attctcttttt aaatatatac cgattttatt agttaatata aaaaaaaaat    780
agtatgaact aataaaattg atcaaaagta aattaatata aatataaaat tttatatgat    840
gaataatcag tagaaataat aaaaaagtta gctctagaaa agataaattg atttaattag    900
ggtcatgaca aaattttgct agcttctatt ttagtctgct ttgctttaga atatttacat    960
tcaaatagct cttttatagc ataacaaaca taaaaaagc tattgattct acataaaaaa  1020
aaaagattaa ttatgctatt ctttgggaca aaacttttag atgaatgcca atttaaaata  1080
attattaagg tattcaagca gacgtacgca agtcgagtaa tactagtggt cacctaagtg  1140
actagggtca cgtgacccta gtcacttatt cccgggtacc gagctcacta gacgcggtga  1200
aattacctaa ttaacaccgg tgtttaaaca ctagtaacgg ccgccagtgt gctggaattc  1260
gcccttccca agctttgctc tagatcaaac tcacatccaa acataacatg gatatcttcc  1320
ttaccaatca tact                                                    1334
```

<210> SEQ ID NO 32
<211> LENGTH: 26
<212> TYPE: DNA
<213> ORGANISM: Artificial Sequence
<220> FEATURE:
<223> OTHER INFORMATION: WOL312 primer sequence

<400> SEQUENCE: 32

```
aatcgacttc aataacaagt ggcatc                                          26
```

<210> SEQ ID NO 33
<211> LENGTH: 28
<212> TYPE: DNA
<213> ORGANISM: Artificial Sequence
<220> FEATURE:
<223> OTHER INFORMATION: WOL193 primer sequence

<400> SEQUENCE: 33

```
ttccaatttg agagggtata tttccttc                                        28
```

<210> SEQ ID NO 34
<211> LENGTH: 1620
<212> TYPE: DNA
<213> ORGANISM: Artificial Sequence
<220> FEATURE:
<223> OTHER INFORMATION: PCR product with WOL312 and WOL193

<400> SEQUENCE: 34

```
aatcgacttc aataacaagt ggcatcacgt ttctagttct agaccatca gctgggccgg      60
cccagctgat gatcccggtg aagttcctat tccgaagttc ctattctcca gaaagtatag    120
gaacttcact agagcttgcg gccgcgcatg ctgacttaat cagctaacgc cactcgacct    180
gcaggcatgc ccgcggatat cgatgggccc cggccgaagc ttcaagtttg tacaaaaaag    240
caggctccgg ccagaatccg gtaagtgact agggtcacgt gacccctagtc acttaaattc    300
ggccagaatg gccatctgga ttcagcaggc ctagaaggcc cggaccgatt aaacttttaat    360
tcggtccggg ttaccaagct tggatccgtc gacgaattca ctagtggtca cctaagtgac    420
tagggtcacg tgaccctagt cacttattcc cgggcaccca gctttcttgt acaaagtggc    480
cgttaacgga tcggccagaa tccggtaagt gactagggtc acgtgaccct agtcacttaa    540
attcggccag aatggccatc tggattcagc aggcctagaa ggcccggacc gattaaactt    600
taattcggtc cgggttacct ctagaaagct tgtcgacctg caggcaagta gctttgttac    660
tttcgtattg acaattcaaa atcgtctttt atttttattt tgttttgttt aattagagga    720
```

```
cttttttgaag tcgtccatca tgtgtttctt attttgtcag ttttgtcact tatgaacact    780 tttttttacag acaaataata tattatatta aaaaaaccat acttataaca acaacatgta    840
acacgttggc aaacagttaa tctcaaccaa acgctcgaaa acttttggat attatatata    900
tatatgcatg gctattggca gtgctaaagt catcattatc attctaaagt catcagtatc    960
attctaattc tcatattgag tggattcatt tcatcaatca ctttgccttt ctcatcataa   1020
ccaccaaaat gccaaccatt aatccagttg gtttgaaatt catggaaggc ataataacat   1080
ttatgatgat gatgttgcag gttgttgttt ctgctcaaga ccatattatg tgcattcaga   1140
ctgagagaga agcactcctc caattcaagg ctgcacttct ggatcactat ggcatgctct   1200
cttcttggac cacttctgat tgctgccaat ggcaagggat tcgctgctcc aacctcaccg   1260
cccatgttct aatgctcgac cttcacagtt taggcctcag aggagagatc caccagtcgt   1320
tgatggagtt gcaacaatta aactatttaa acctcagttg gaattctttt caaggcagag   1380
gaatcccaga gttcttggt tctctcacca acttgagata ccttgatctg tcacattctg   1440
attttgaagg aaaaattcca actcagtttg gctctctttc tcatttgaaa tacttaaatc   1500
ttgctgggaa ttattatctg gagggttcaa tcccacgtca acttggaaat ctctcccagt   1560
tgcagcatct tgatctcagg gccaatcaat ttgaaggaaa tataccctct caaattggaa   1620
```

<210> SEQ ID NO 35
<211> LENGTH: 1000
<212> TYPE: DNA
<213> ORGANISM: Glycine max
<220> FEATURE:
<221> NAME/KEY: misc_feature
<222> LOCATION: (1)..(1000)
<223> OTHER INFORMATION: HR1 of TS14

<400> SEQUENCE: 35

```
attttgtcag tcttgtaact ttgaaaact ttttttcttt tttttataga ccaataaatat     60 aatatattat attaaaaaaa ccaaacttat aacaacatgt aacacgttag caaacagtag    120
atctcaacca aacgttcgaa aacttttgga tattatatat gtggctgttg gcactgctaa    180
actcagcagt atatctccat tattgatgag tctctcctaa aattatcttt ccaagtctta    240 tttttattt aattggttag atattaaatt gaaaataaa ataaagttg tgttgttgtg     300 tagttttcgt cactttttact cataagaaaa tatatatact acgttagca tctttaaact    360 gaaaactttt cagttgaaat gcataacaaa atattggcca agtaattagt acacaaaatc    420
ttgctcaaag tgtttgccac catagattta ggttgtgttt aggacgatta cttaaaatat    480
cattaattga taattgaaac ttcaaataaa atttaaaagt ttaaaagttg aatagttaaa    540
aatgaaagct gaaaataaat aagctaatgg attcaatttg aagtatttaa tagtatcaac    600
tagtgaaatt tattcataaa ttctctttta aatatatacc gattttatta gttaatataa    660
aaaaaaaata gtatgaacta ataaaattga tcaaagtaa attaatataa atataaaatt    720
ttatatgatg aataatcagt agaaataata aaaagttag ctctagaaaa gataaattga    780
tttaattagg gtcatgacaa aattttgcta gcttctattt tagtctgctt tgctttagaa    840
tatttacatt caaatagctc ttttatagca taacaaacat aaaaaaagct attgattcta    900
cataaaaaaa aaagattaat tatgctattc tttgggacaa aacttttaga tgaatgccaa    960
tttaaaataa ttattaaggt attcaagcag acgtacgcaa                         1000
```

<210> SEQ ID NO 36

```
<211> LENGTH: 928
<212> TYPE: DNA
<213> ORGANISM: Glycine max
<220> FEATURE:
<221> NAME/KEY: misc_feature
<222> LOCATION: (1)..(928)
<223> OTHER INFORMATION: HR2 of TS14

<400> SEQUENCE: 36
gcaagtagct ttgttacttt cgtattgaca attcaaaatc gtcttttatt tttattttgt      60
tttgtttaat tagaggactt tttgaagtcg tccatcatgt gtttcttatt ttgtcagttt     120
tgtcacttat gaacactttt tttacagaca aataatatat tatattaaaa aaaccatact    180
tataacaaca acatgtaaca cgttggcaaa cagttaatct caaccaaacg ctcgaaaact    240
tttggatatt atatatatat atgcatggct attggcagtg ctaaagtcat cattatcatt    300
ctaaagtcat cagtatcatt ctaattctca tattgagtgg attcatttca tcaatcactt    360
tgcctttctc atcataacca ccaaaatgcc aaccattaat ccagttggtt tgaaattcat    420
ggaaggcata ataacattta tgatgatgat gttgcaggtt gttgtttctg ctcaagacca    480
tattatgtgc attcagactg agagagaagc actcctccaa ttcaaggctg cacttctgga    540
tcactatggc atgctctctt cttggaccac ttctgattgc tgccaatggc aagggattcg    600
ctgctccaac ctcaccgccc atgttctaat gctcgacctt cacagtttag gcctcagagg    660
agagatccac cagtcgttga tggagttgca acaattaaac tatttaaacc tcagttggaa    720
ttcttttcaa ggcagaggaa tcccagagtt tcttggttct ctcaccaact tgagatacct    780
tgatctgtca cattctgatt ttgaaggaaa aattccaact cagtttggct ctctttctca    840
tttgaaatac ttaaatcttg ctgggaatta ttatctggag ggttcaatcc cacgtcaact    900
tggaaatctc tcccagttgc agcatctt                                        928
```

METHODS AND COMPOSITIONS FOR TARGETED INTEGRATION IN A PLANT

CROSS-REFERENCE TO RELATED APPLICATIONS

Figure 1:
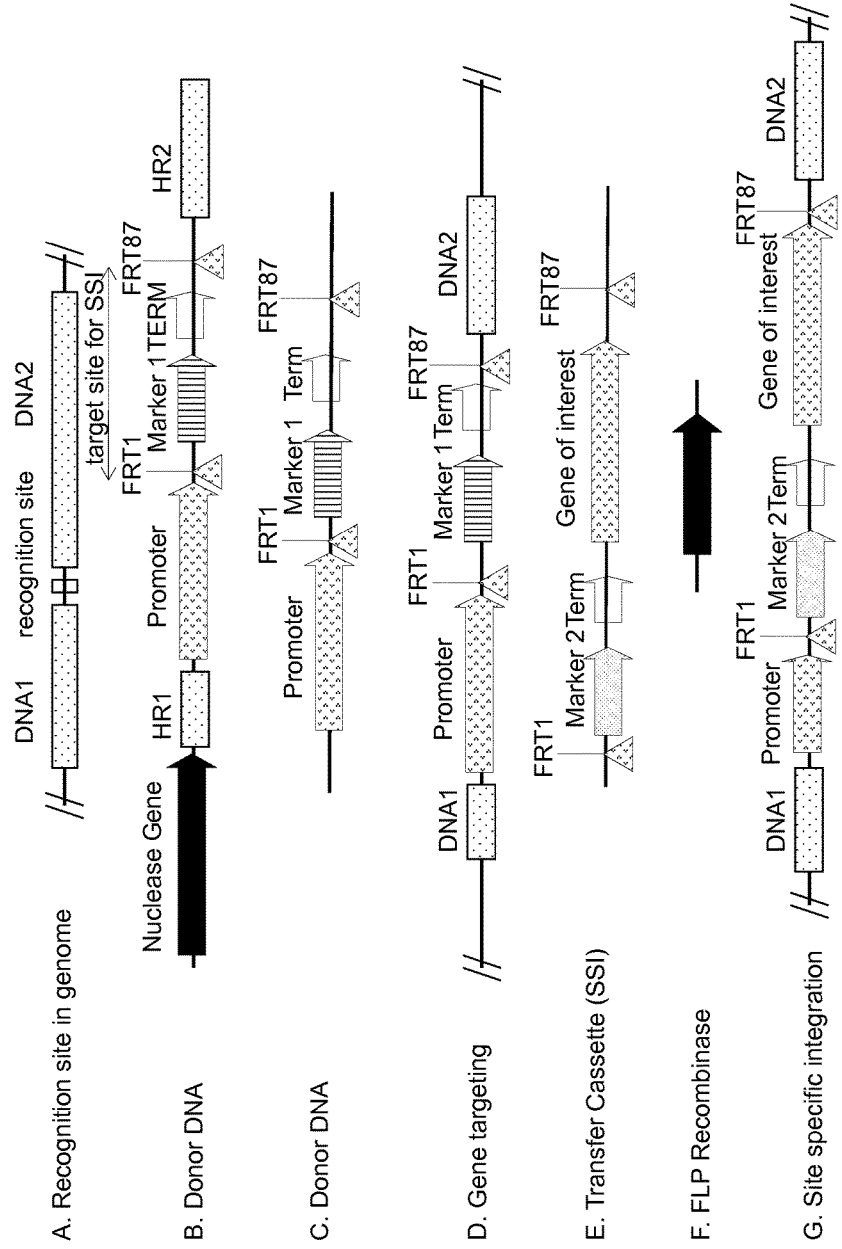

This application is a National Phase Application of International Application No. PCT/US2012/047202, filed Jul. 18, 2012, which claims priority to U.S. patent application Ser. No. 61/514,565, filed Aug. 3, 2011, both of which are incorporated herein fully by this reference.

FIELD OF THE INVENTION

The invention relates to the field of plant molecular biology. In particular, methods and compositions are provided for altering the genome of a plant.

BACKGROUND OF THE INVENTION

Recombinant DNA technology has made it possible to insert foreign DNA sequences into the genome of an organism, thus, altering the organism's phenotype. The most commonly used plant transformation methods are *Agrobacterium* infection and biolistic particle bombardment in which transgenes integrate into a plant genome in a random fashion and with an unpredictable copy number.

Site-specific integration techniques, which employ site-specific recombination systems, as well as, other types of recombination technologies, have been used to generate targeted insertions of genes of interest in a variety of organism.

Other methods for inserting or modifying a DNA sequence involve homologous DNA recombination by introducing a transgenic DNA sequence flanked by sequences homologous to the genomic target. U.S. Pat. No. 5,527,695 describes transforming eukaryotic cells with DNA sequences that are targeted to a predetermined sequence of the eukaryote's DNA. Transformed cells are identified through use of a selectable marker included as a part of the introduced DNA sequences.

While both systems have provided useful techniques for targeted insertion of sequences of interest, there remains a need for methods and compositions which improve these systems and allow for a gene of interest to be targeted to a specific site in the plant genome.

BRIEF SUMMARY OF THE INVENTION

Methods and compositions for targeting a polynucleotide of interest to a specific site in the genome of a plant or plant cell are provided.

Methods for introducing into the genome of a plant cell a target site for site-specific integration are provided. The method comprises providing a plant cell comprising in its genome an endogenous recognition site for an engineered endonuclease, wherein the engineered endonuclease is capable of inducing a double-strand break in the endogenous recognition site, and wherein the endogenous recognition site is located between a first and a second genomic region. A donor DNA comprising a target site for site-specific integration located between a first region of homology to the first genomic region and a second region of homology to the second genomic region is provided, wherein the target site comprises a first and a second recombination site, and the first and the second recombination sites are dissimilar and non-recombinogenic with respect to one another. The plant cell is contacted with the donor DNA and the engineered endonuclease, and least one plant cell comprising in its genome the target site integrated at the endogenous recognition site is identified.

Further provided is a method of integrating a polynucleotide of interest into a specific site in the genome of a plant cell. The method comprises providing at least one plant cell comprising in its genome a target site for site-specific integration, wherein the target site is integrated into an endogenous recognition site for an engineered endonuclease, and wherein the target site is, (i) a target site comprising a first and a second recombination site, or (ii) the target site of (i) further comprising a third recombination site between the first recombination site and the second recombination site, wherein the engineered endonuclease is capable of inducing a double-strand break in the endogenous recognition site, wherein the first, the second, and the third recombination sites are dissimilar and non-recombinogenic with respect to one another. The plant cell is transformed with a transfer cassette comprising, (iii) the first recombination site, a first polynucleotide of interest, and the second recombination site, (iv) the second recombination site, a second polynucleotide of interest, and the third recombination site, or (v) the first recombination site, a third polynucleotide of interest, and the third recombination site. A recombinase is provided that recognizes and implements recombination at the first and the second recombination sites, at the second and the third recombination sites, or at the first and third recombination sites. At least one plant cell comprising integration of the transfer cassette at the target site is selected.

Various compositions include a plant, a seed or a plant cell comprising in its genome a target site for site-specific integration, wherein the target site is integrated into an endogenous recognition site for an engineered endonuclease, wherein the target site comprises in the following order: (a) a first recombination site; and, (b) a second recombination site, and wherein the engineered endonuclease is capable of inducing a double-strand break at the endogenous recognition site, wherein the first and the second recombination sites are dissimilar and non-recombinogenic with respect to one another.

BRIEF DESCRIPTION OF THE DRAWINGS AND SEQUENCE LISTING

The invention can be more fully understood from the following detailed description and the accompanying drawings and Sequence Listing which form a part of this application.

FIG. 1. Schematic of the DNA double-strand-break-induced DNA alteration of an endogenous recognition site to integrate a target site followed by FLP recombinase mediated site-specific integration at the target site.

Figure 2:
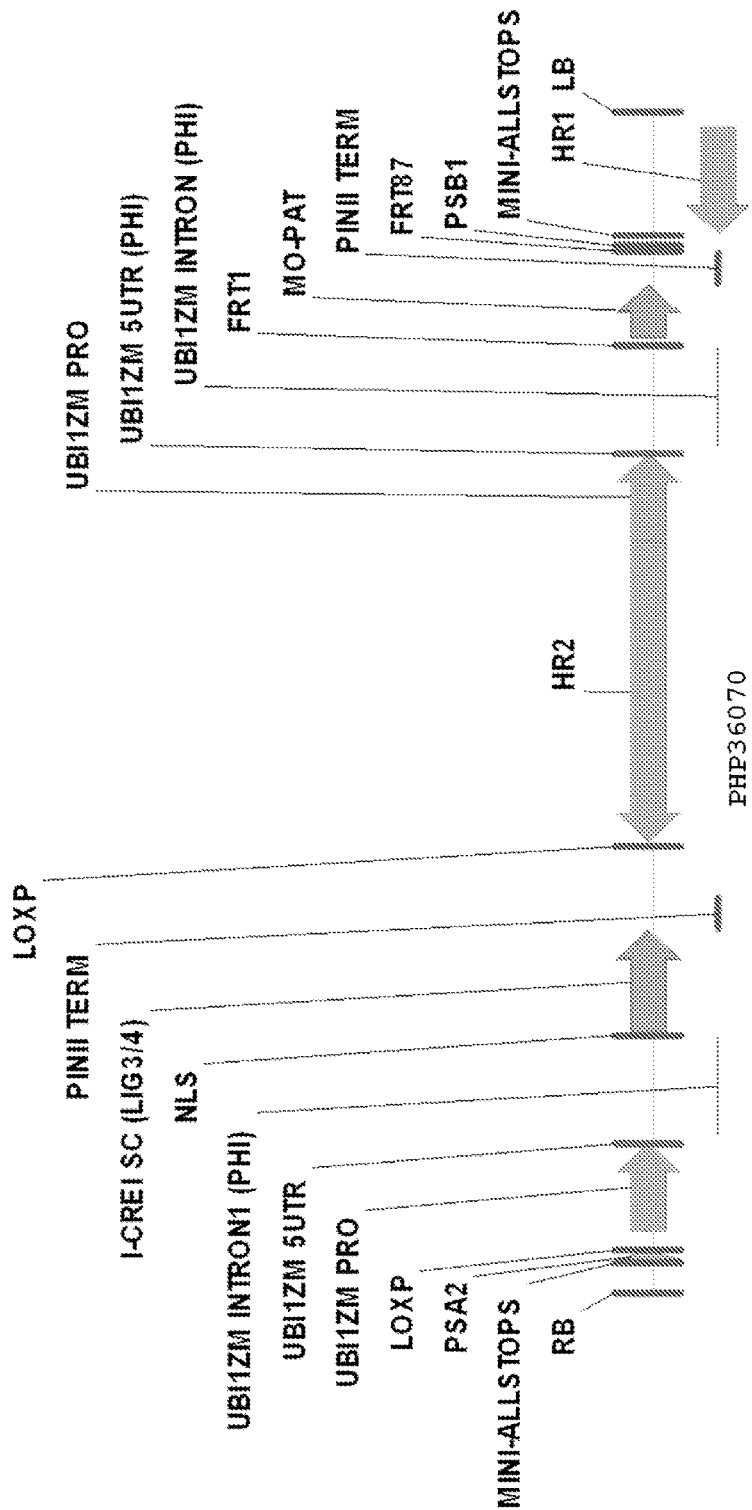

FIG. 2. Fragment of plasmid PHP36070 used to create the transgenic insertion at the LIG3-4 recognition site.

Figure 3:
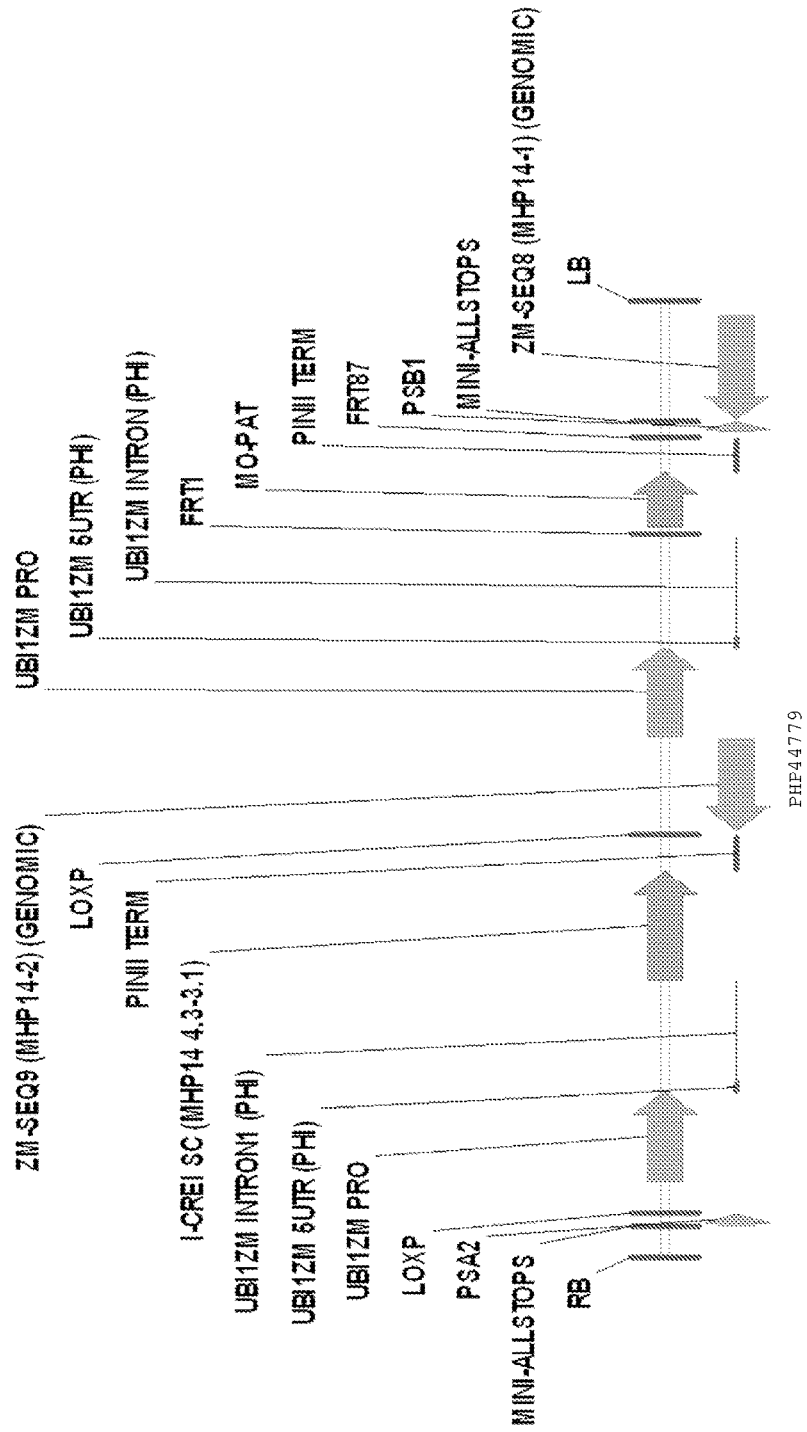

FIG. 3. Fragment of plasmid PHP44779 used to create the transgenic insertion at the MHP14 recognition site.

Figure 4:

FIG. 4. Graphic representation of the transgenic insertion site following homologous recombination mediated by meganuclease induced double stranded breaks. PCR and Southern analysis were used to obtain information about the molecular structure of the transgene insertions.

Figure 5:
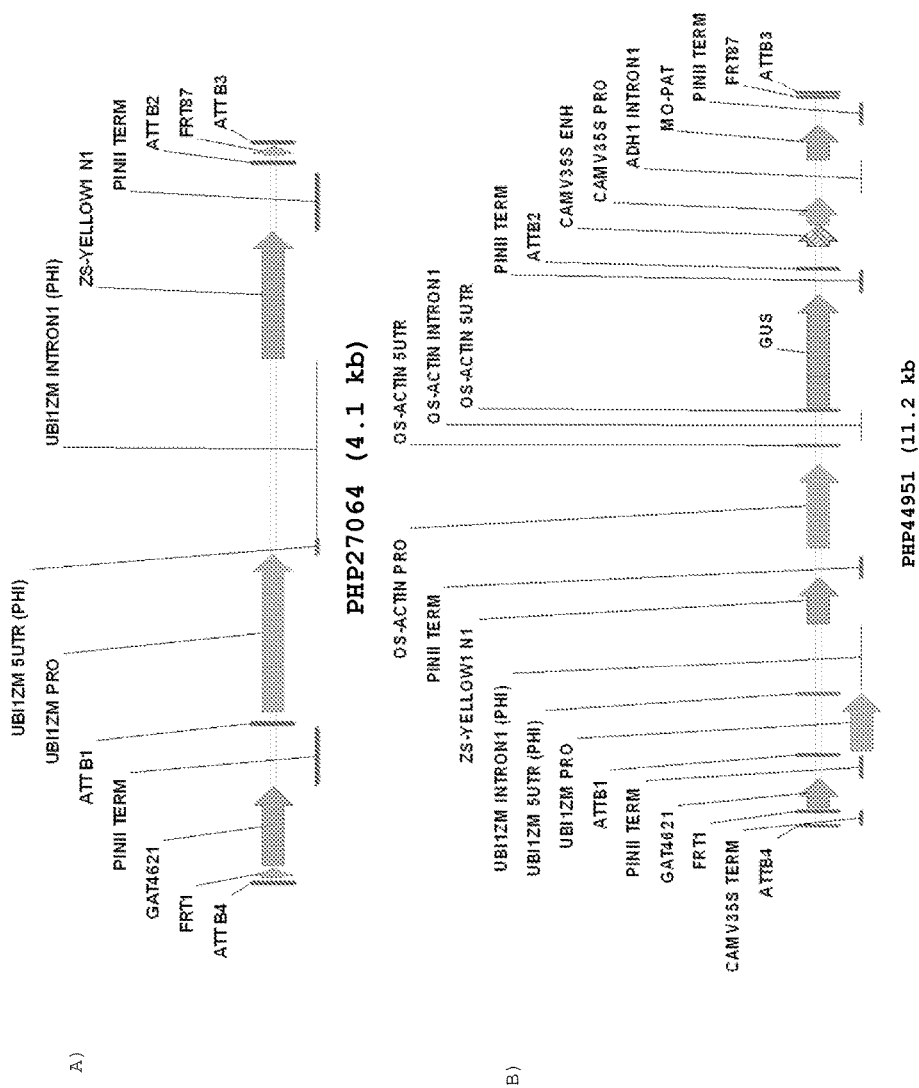

FIG. 5. Transfer Cassettes Plasmids PHP27064 and PHP44951 for FLP recombinase mediated site specific integration and RMCE.

FIG. 6. Integration of transfer cassette at the MHP14 SSI target site after FLP recombinase mediated site specific integration.

TABLE 1

Sequences 1-13

| SEQ ID NO: | NT/ AA | Description |
|---|---|---|
| 1 | NT | TS21 recognition site of soybean ggcactctcg tgtgtgatta aa |
| 2 | NT | TS14 recognition site of soybean cagacgtacg caagtagctt tg |
| 3 | NT | TS30 recognition site of soybean gagtcccacg caagagcata aa |
| 4 | NT | TS5 recognition site of soybean aagacttacg tgtgtactcg tg |
| 5 | NT | TS7 recognition site of soybean gacattgtcg tgagaaaaga ga |
| 6 | NT | TS4 recognition site of soybean aaatctgtct tgcgaaacgt ca |
| 7 | NT | TS22 recognition site of soybean tattctctca taaataaact tt |
| 8 | NT | TS24 recognition site of soybean ggaatggaca taagagaact gt |
| 9 | NT | FRT1 recombination site gaagttccta ttctctagaa agtataggaa cttc |
| 10 | NT | FRT5 recombination site agttcctatt cttcaaaagg tataggaact |
| 11 | NT | FRT6 recombination site agttcctatt cttcaaaaag tataggaact |
| 12 | NT | FRT12 recombination site agttcctata ctctatgtag aataggaact |
| 13 | NT | FRT87 recombination site agttcctata ctttctggag aataggaact |

NT = nucleotide seqeunce

SEQ ID NO: 14 PHP36070
SEQ ID NO: 15 is the nucleotide sequence of the LIG3-4 meganuclease
SEQ ID NO: 16 is the nucleotide sequence of the LIG3-4 recognition site.
SEQ ID NO: 17 is the homologous DNA region (HR1) flanking the LIG3-4 recognition site.
SEQ ID NO: 18 is the homologous DNA region (HR2) flanking the LIG3-4 recognition site.
SEQ ID NO: 19 PHP44779
SEQ ID NO: 20 is the nucleotide sequence of the MHP14 recognition site in the maize genome.
SEQ ID NO:21 is the plant optimized nucleotide sequence of the MHP14+ comprising a nuclear localization signal and lacking an intron.
SEQ ID NO: 22 is the HR1 of the MHP14 target site.
SEQ ID NO: 23 is the HR2 of the MHP14 target site.
SEQ ID NO: 24 is the Transfer Cassette plasmid PHP27064.
SEQ ID NO: 25 is the Transfer Cassette plasmid PHP44951.
SEQ ID NO: 26 is the plant optimized nucleotide sequence of the TS14 meganuclease.
SEQ ID NO: 27 RTW347
SEQ ID NO: 28 RTW365
SEQ ID NO: 29 WOL192 primer sequence
SEQ ID NO: 30 WOL311 primer sequence
SEQ ID NO: 31 PCR product with WOL192 and WOL311
SEQ ID NO: 32 WOL312 primer sequence
SEQ ID NO: 33 WOL193 primer sequence
SEQ ID NO: 34 PCR product with WOL312 and WOL193
SEQ ID NO: 35 is the homologous DNA region (HR1) flanking the TS14 recognition site.
SEQ ID NO: 36 is the homologous DNA region (HR2) flanking the TS14 recognition site.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

Compositions and methods are provided for the targeted integration of a polynucleotide sequence of interest into the genome of a plant or plant cell. The methods and compositions employ endonucleases, recognition sites for these endonucleases in combination with site-specific recombination sites/recombinases to provide an effective system for establishing target sites within the genome of a plant, plant cell or seed. Once such target sites are established, a variety of methods can be employed to further modify the target sites such that they contain a variety of polynucleotides of interest.

II. Target Sites Integrated at a Recognition Site

Methods and compositions are provided herein which establish and use plants, plant cells and seeds having stably incorporated into their genome a target site for site-specific integration where the target site is integrated into a recognition site for an endonuclease. As used herein, a target site is "integrated" into a recognition site when an endonuclease induces a double strand break at the recognition site and a homologous recombination event thereby inserts the target site with the boundaries of the original recognition site. It is recognized that the position within a given recognition site in which the target site integrates will vary depending on where the double strand break is induced by the endonuclease. The sequence of the recognition site need not immediately flank the boundaries of the target site. For example, sequences 5' and 3' to the target site found on the donor DNA may also be integrated into the recognition site.

A. Recognition Sites for Endonucleases

As used herein, the term "recognition site for an endonuclease" refers to a DNA sequence at which a double-strand break is induced in the plant cell genome by an endonuclease. The recognition site can be an endogenous site in the plant genome, or alternatively, the recognition site can be heterologous to the plant and thereby not be naturally occurring in the genome, or the recognition site can be found in a heterologous genomic location compared to where it occurs in nature. As used herein, the term "endogenous recognition site" refers to an endonuclease recognition site that is endogenous or native to the genome of a plant and is located at the endogenous or native position of that recognition site in the genome of the plant.

The length of the recognition site can vary, and includes, for example, recognition sites that are at least 4, 6, 8, 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length. It is further possible that the recognition site could be palindromic, that is, the sequence on one strand reads the same in the opposite direction on the complementary strand. The nick/cleavage site could be within the recognition sequence or the nick/cleavage site could be outside of the recognition sequence. In another variation, the cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs.

In one embodiment, the recognition site of the endonuclease comprises the TS21 (SEQ ID NO: 1), TS14 (SEQ ID NO: 2), TS30 (SEQ ID NO: 3), TS5 (SEQ ID NO: 4), TS7 (SEQ ID NO: 5), TS4 (SEQ ID NO: 6), TS22 (SEQ ID NO: 7), and/or TS24 (SEQ ID NO: 8) recognition sites of soybean which are disclosed in U.S. Provisional Application No. 61/466,602, filed on Mar. 23, 2011, herein incorporated by reference in its entirety. In another embodiment, the recognition site can comprise the LIG3-4 recognition site (SEQ ID NO:16) and the MHP14 recognition site (SEQ ID NO:20)

Any endonuclease that induces a double-strand break into a desired recognition site can be used in the methods and compositions disclosed herein. A naturally-occurring or native endonuclease can be employed so long as the endonuclease induces a double-strand break in a desired recognition site. Alternatively, a modified or engineered endonuclease can be employed. An "engineered endonuclease" refers to an endonuclease that is engineered (modified or derived) from its native form to specifically recognize and induce a double-strand break in the desired recognition site. Thus, an engineered endonuclease can be derived from a native, naturally-occurring endonuclease or it could be artificially created or synthesized. The modification of the endonuclease can be as little as one nucleotide. In some embodiments, the engineered endonuclease induces a double-strand break in a recognition site, wherein the recognition site was not a sequence that would have been recognized by a native (non-engineered or non-modified) endonuclease. Producing a double-strand break in a recognition site or other DNA can be referred to herein as "cutting" or "cleaving" the recognition site or other DNA.

Active variants and fragments of the recognition sites (i.e. SEQ ID NOS: 1-8, 16 and 20) are also provided. Such active variants can comprise at least 65%, 70%, 75%, 80%, 85%, 90%, 91%, 92%, 93%, 94%, 95%, 96%, 97%, 98%, 99% or more sequence identity to the given recognition site, wherein the active variants retain biological activity and hence are capable of being recognized and cleaved by an endonuclease. Assays to measure the double-strand break of a recognition site by an endonuclease are known in the art and generally measure the ability of an endonuclease to cut the recognition site.

Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex.

Type I and Type III restriction endonucleases recognize specific recognition sites, but typically cleave at a variable position from the recognition site, which can be hundreds of base pairs away from the recognition site. In Type II systems the restriction activity is independent of any methylase activity, and cleavage typically occurs at specific sites within or near to the recognition site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site.

Type IV restriction enzymes target methylated DNA. Restriction enzymes are further described and classified, for example in the REBASE database (webpage at rebase.neb.com; Roberts et al., (2003) *Nucleic Acids Res* 31:418-20), Roberts et al., (2003) *Nucleic Acids Res* 31:1805-12, and Belfort et al., (2002) in *Mobile DNA II*, pp. 761-783, Eds. Craigie et al., (ASM Press, Washington, D.C.).

Endonucleases also include meganucleases, also known as homing endonucleases (HEases), which like restriction endonucleases, bind and cut at a specific recognition site, however the recognition sites for meganucleases are typically longer, about 18 bp or more. Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing open reading frames, introns, and inteins, respectively. For example, intron-, intein-, and freestanding gene encoded meganuclease from *Saccharomyces cerevisiae* are denoted I-SceI, PI-SceI, and F-SceII, respectively. Meganuclease domains, structure and function are known, see for example, Guhan and Muniyappa (2003) *Crit Rev Biochem Mol Biol* 38:199-248; Lucas et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure et al., (2002) *Nat Struct Biol* 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) *Nucleic Acids Res* 31:2952-62; Chevalier et al., (2002) *Mol Cell* 10:895-905;

Gimble et al., (2003) *Mol Biol* 334:993-1008; Seligman et al., (2002) *Nucleic Acids Res* 30:3870-9; Sussman et al., (2004) *J Mol Biol* 342:31-41; Rosen et al., (2006) *Nucleic Acids Res* 34:4791-800; Chames et al., (2005) *Nucleic Acids Res* 33:e178; Smith et al., (2006) *Nucleic Acids Res* 34:e149; Gruen et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346.

Any meganuclease can be used herein, including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof. In a specific embodiment, the engineered endonuclease is derived from I-Cre-I having the sequence set forth in SEQ ID NO: 15, 21 or 26 or an active variant or fragment thereof.

TAL effector nucleases are a new class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) PNAS 10.1073/pnas.1013133107; Scholze & Boch (2010) *Virulence* 1:428-432; Christian et al. *Genetics* (2010) 186:757-761; Li et al. (2010) *Nuc. Acids Res*. (2010) doi:10.1093/nar/gkq704; and Miller et al. (2011) *Nature Biotechnology* 29:143-148; all of which are herein incorporated by reference.

The endonuclease can be provided via a polynucleotide encoding the endonuclease. Such a polynucleotide encoding an endonuclease can be modified to substitute codons having a higher frequency of usage in a plant, as compared to the naturally occurring polynucleotide sequence. For example the polynucleotide encoding the endonuclease can be modified to substitute codons having a higher frequency of usage in a maize or soybean plant, as compared to the naturally occurring polynucleotide sequence.

Active variants and fragments of endonucleases (i.e. an engineered endonuclease) are also provided. Such active variants can comprise at least 65%, 70%, 75%, 80%, 85%, 90%, 91%, 92%, 93%, 94%, 95%, 96%, 97%, 98%, 99% or more sequence identity to the native endonuclease, wherein the active variants retain the ability to cut at a desired recognition site and hence retain double-strand-break-inducing activity. For example, any of the engineered endonucleases described herein can be modified from a native endonuclease sequence and designed to recognize and induce a double strand break at a recognition site that was not recognized by the native endonuclease. Thus in some embodiments, the engineered endonuclease has a specificity to induce a double-strand break at a recognition site that is different from the corresponding native endonuclease recognition site. Assays for double-strand-break-inducing activity are known and generally measure the overall activity and specificity of the endonuclease on DNA substrates containing the recognition site.

The endonuclease may be introduced by any means known in the art. For example, a plant having the recognition site in its genome is provided. The endonuclease may be transiently expressed or the polypeptide itself can be directly provided to the cell. Alternatively, a nucleotide sequence capable of expressing the endonuclease may be stably integrated into the genome of the plant. In the presence of the corresponding recognition site and the endonuclease, the donor DNA is inserted into the transformed plant's genome. Alternatively, the components of the system may be brought together by sexually crossing transformed plants. Thus a sequence encoding the endonuclease and/or target site can be sexually crossed to one another to allow each component of the system to be present in a single plant. The endonuclease may be under the control of a constitutive or inducible promoter. Such promoters of interest are discussed in further detail elsewhere herein.

B. Integration of a Target Site into the Recognition Site by Homologous Recombination As outlined above, plants, plant cells and seeds having a target site integrated at a recognition site are provided. Various methods can be used to integrate the target site at the recognition site. Such methods employ homologous recombination to provide integration of the target site at the endonuclease recognition site. In the methods provided, the target site is provided to the plant cell in a donor DNA construct. As used herein, "donor DNA" is a DNA construct that comprises a target site for site-specific integration. The donor DNA construct further comprises a first and a second region of homology that flank the target site sequence. The first and second regions of homology of the donor DNA share homology to a first and a second genomic region, respectively, present in or flanking the recognition site of the plant genome. By "homology" is meant DNA sequences that are similar. For example, a "region of homology to a genomic region" that is found on the donor DNA is a region of DNA that has a similar sequence to a given "genomic region" in the plant genome. A region of homology can be of any length that is sufficient to promote homologous recombination at the cleaved recognition site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction.

As used herein, a "genomic region" is a segment of a chromosome in the genome of a plant cell that is present on either side of the recognition site or, alternatively, also comprises a portion of the recognition site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the plant genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the recognition site. While in some embodiments the regions of homology share a significant sequence homology to the genomic sequence immediately flanking the recognitions site, it is recognized that the regions of homology can be designed to have sufficient homology to regions that may be further 5' or 3' to the recognition site. In still other embodiments, the regions of homology can also have homology with a fragment of the recognition site along with downstream genomic regions. In one embodiment, the first region of homology further comprises a first fragment of the recognition site and the second region of homology comprises a second fragment of the recognition site, wherein the first and second fragments are dissimilar. In a further embodiment the first region of homology comprises the first 13 bases of the recognition site and the second region of homology comprises the last 9 bases of the recognition site.

As used herein, "homologous recombination" refers to the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events, the longer the region of homology, the greater the frequency. The length of the homology region needed to observe homologous recombination is also species-variable. In many cases, at least 5 kb of homology has been utilized, but homologous recombination has been observed with as little as 25-50 bp of homology. See, for example, Singer et al., (1982) *Cell* 31:25-33; Shen and Huang, (1986) *Genetics* 112:441-57; Watt et al., (1985) *Proc. Natl. Acad. Sci. USA* 82:4768-72, Sugawara and Haber, (1992) *Mol Cell Biol* 12:563-75, Rubnitz and Subramani, (1984) *Mol Cell Biol* 4:2253-8; Ayares et al., (1986) *Proc. Natl. Acad. Sci. USA* 83:5199-203; Liskay et al., (1987) *Genetics* 115:161-7.

Alteration of the genome of a plant cell, for example, through homologous recombination (HR), is a powerful tool for genetic engineering. The parameters for homologous recombination in plants have primarily been investigated by rescuing introduced truncated selectable marker genes. In these experiments, the homologous DNA fragments were typically between 0.3 kb to 2 kb. Observed frequencies for homologous recombination were on the order of $10^{-4}$ to $10^{-5}$. See, for example, Halfter et al., (1992) *Mol Gen Genet* 231:186-93; Offringa et al., (1990) *EMBO J* 9:3077-84; Offringa et al., (1993) *Proc. Natl. Acad. Sci. USA* 90:7346-50; Paszkowski et al., (1988) *EMBO J* 7:4021-6; Hourda and Paszkowski, (1994) *Mol Gen Genet* 243:106-11; and Risseeuw et al., (1995) *Plant J* 7:109-19.

Once a double-strand break is induced in the DNA, the cells DNA repair mechanism is activated to repair the break. Error-prone DNA repair mechanisms can produce mutations at double-strand break sites. The most common repair mechanism to bring the broken ends together is the nonhomologous end-joining (NHEJ) pathway (Bleuyard et al., (2006) *DNA Repair* 5:1-12). The structural integrity of chromosomes is typically preserved by the repair, but deletions, insertions, or other rearrangements are possible (Siebert and Puchta, (2002) *Plant Cell* 14:1121-31; Pacher et al., (2007) *Genetics* 175:21-9).

Alternatively, the double-strand break can be repaired by homologous recombination between homologous DNA sequences. Once the sequence around the double-strand break is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) *Plant Cell* 16:342-52). Ectopic and/or epigenic DNA sequences may also serve as a DNA repair template for homologous recombination (Puchta, (1999) *Genetics* 152:1173-81).

DNA double-strand breaks appear to be an effective factor to stimulate homologous recombination pathways (Puchta et al., (1995) *Plant Mol Biol* 28:281-92; Tzfira and White, (2005) *Trends Biotechnol* 23:567-9; Puchta, (2005) *J Exp Bot* 56:1-14). Using DNA-breaking agents, a two- to ninefold increase of homologous recombination was observed between artificially constructed homologous DNA repeats in plants (Puchta et al., (1995) *Plant Mol Biol* 28:281-92). In maize protoplasts, experiments with linear DNA molecules demonstrated enhanced homologous recombination between plasmids (Lyznik et al., (1991) *Mol Gen Genet* 230:209-18).

Provided herein, the methods comprise contacting a plant cell with the donor DNA and the endonuclease. Once a double-strand break is introduced in the recognition site by the endonuclease, the first and second regions of homology of the donor DNA can undergo homologous recombination with their corresponding genomic regions of homology resulting in exchange of DNA between the donor and the genome. As such, the provided method results in the integration of the target site of the donor DNA into the double-strand break in the recognition site in the plant genome.

The donor DNA may be introduced by any means known in the art. For example, a plant having a recognition site is provided. The donor DNA may be provided by any transformation method known in the art including, for example, *Agrobacterium*-mediated transformation or biolistic particle bombardment. The donor DNA may be present transiently in the cell or it could be introduced via a viral replicon. In the presence of the endonuclease and the recognition site, the donor DNA is inserted into the transformed plant's genome.

Further provided are methods for identifying at least one plant cell comprising in its genome the target site integrated at the recognition site. A variety of methods are available for identifying those plant cells with insertion into the genome at or near to the recognition site without using a screenable marker phenotype. Such methods can be viewed as directly analyzing a recognition sequence to detect any change in the recognition sequence, including but not limited to PCR methods, sequencing methods, nuclease digestion, Southern blots, and any combination thereof. See, for example, U.S. patent application Ser. No. 12/147,834, herein incorporated by reference in its entirety.

The method also comprises recovering a fertile plant from the plant cell comprising a target site integrated into its genome. As used herein, a "fertile plant" is a plant that is capable of producing a progeny plant. The fertile plant can comprise any of the various target sites as described elsewhere herein integrated in its genome into the Recognition Site.

III. Methods for Integrating a Polynucleotide of Interest Into the Target Site

As outlined above, various methods and compositions can be employed to obtain a plant having a target site inserted in a recognition site for an endonuclease. Once such plants and plant cells are generated, a variety of methods can be used to manipulate the sequence within the target site. Such methods employ various components of site-specific recombination systems.

A. The Target Site and Components Thereof

As discussed herein, the various methods and compositions employ a target site. As described in the previous section, the target site is provided in a donor DNA which undergoes homologous recombination with the genomic DNA at the cleaved recognition site resulting in integration of the target site into the genome of the plant cell.

The target site can comprise various components. As used herein, by "target site" is intended a polynucleotide comprising a nucleotide sequence flanked by at least two recombination sites. In some embodiments, the recombination sites of the target site are dissimilar and non-recombinogenic with respect to one another. One or more intervening sequences may be present between the recombination sites of the target site. Intervening sequences of particular interest would include linkers, adapters, selectable markers, polynucleotides of interest, promoters and/or other sites that aid in vector construction or analysis. In addition, the recombination sites of the target site can be located in various positions, including, for example, within intronic sequences, coding sequences, or untranslated regions.

The target site can comprise 1, 2, 3, 4, 5, 6 or more recombination sites. In one embodiment, the target site comprises a first recombination site and a second recombination site wherein the first and the second recombination site are dissimilar and non-recombinogenic to each other. In a further embodiment, the target site comprises a third recombination site between the first recombination site and the second recombination site. In such embodiments, the first, second and third recombination sites may be dissimilar and non-recombinogenic with respect to one another. Such first, second and third recombination sites are able to recombine with their corresponding or identical recombination site when provided with the appropriate recombinase. The various recombination sites and recombinases encompassed by the methods and compositions are described in detail elsewhere herein.

The recombination sites employed in the methods and compositions provided herein can be "corresponding" sites or "dissimilar" sites. By "corresponding recombination sites" or a "set of corresponding recombination sites" is intended that the recombination sites have the same or corresponding nucleotide sequence. A set of corresponding recombination sites, in the presence of the appropriate recombinase, will efficiently recombine with one another (i.e., the corresponding recombination sites are recombinogenic).

In other embodiments, the recombination sites are dissimilar. By "dissimilar recombination sites" or a "set of dissimilar recombination sites" is intended that the recombination sites are distinct (i.e., have at least one nucleotide difference).

The recombination sites within "a set of dissimilar recombination sites" can be either recombinogenic or non-recombinogenic with respect to one other. By "recombinogenic" is intended that the set of recombination sites are capable of recombining with one another. Thus, suitable sets of "recombinogenic" recombination sites for use in the methods and compositions provided herein include those sites where the relative excision efficiency of recombination between the recombinogenic sites is above the detectable limit under standard conditions in an excision assay, typically, greater than 2%, 5%, 10%, 20%, 50%, 100%, or greater.

By "non-recombinogenic" is intended the set of recombination sites, in the presence of the appropriate recombinase, will not recombine with one another or recombination between the sites is minimal. Thus, suitable "non-recombinogenic" recombination sites for use in the methods and compositions provided herein include those sites that recombine (or excise) with one another at a frequency lower than the detectable limit under standard conditions in an excision assay, typically, lower than 2%, 1.5%, 1%, 0.75%, 0.5%, 0.25%, 0.1%, 0.075, 0.005%, 0.001%.

Each recombination site within the "set of non-recombinogenic sites" is biologically active and therefore can recombine with an identical site. Accordingly, it is recognized that any suitable non-recombinogenic recombination sites may be utilized, including a FRT site or an active variant thereof, a LOX site or active variant thereof, any combination thereof, or any other combination of non-recombinogenic recombination sites known in the art. FRT sites that can be employed in the methods and compositions disclosed herein can be found, for example, in US Publication No. 2011-0047655, herein incorporated by reference.

In a specific embodiment, at least one of the first, the second and the third recombination site comprises FRT1 (SEQ ID NO: 9), FRT5 (SEQ ID NO: 10), FRT6 (SEQ ID NO: 11), FRT12 (SEQ ID NO: 12) or FRT87 (SEQ ID NO: 13). In a specific embodiment, the first recombination site is FRT1, the second recombination site is FRT12 and the third recombination site is FRT87.

B. Transfer Cassettes and Components Thereof

The methods also comprise introducing into the plant cell comprising the integrated target site a transfer cassette. The transfer cassette comprises various components for the incorporation of polynucleotides of interest into the plant genome. As defined herein, the "transfer cassette" comprises at least a first recombination site, a polynucleotide of interest, and a second recombination site, wherein the first and second recombination sites are dissimilar and non-recombinogenic and correspond to the recombination sites in the target site. The transfer cassette is also immediately flanked by the recombination sites. It is recognized that any combination of restriction sites can be employed in the transfer cassettes to provide a polynucleotide of interest.

In one embodiment, the transfer cassette comprises the first recombination site, a first polynucleotide of interest, and the second recombination site. In such methods, the first and second recombination sites of the transfer cassette are recombinogenic (i.e. identical or corresponding) with the first and second recombination sites of the target site, respectively.

In another embodiment of the methods, the transfer cassette comprises the second recombination site, a second polynucleotide of interest, and the third recombination site. In such methods, the second and third recombination sites of the transfer cassette are recombinogenic (i.e. identical or corresponding) with the second and third recombination sites of the target site in the plant genome, respectively.

In yet, another embodiment, the transfer cassette comprises the first recombination site, a third polynucleotide of interest, and the third recombination site. In such cases, the second and third recombination sites of the transfer cassette are recombinogenic (i.e. identical or corresponding) with the first and third recombination sites of the target site in the plant genome, respectively.

The recombination sites of the transfer cassette may be directly contiguous with the polynucleotide of interest or there may be one or more intervening sequences present between one or both ends of the polynucleotide of interest and the recombination sites. Intervening sequences of particular interest would include linkers, adapters, additional polynucleotides of interest, markers, promoters and/or other sites that aid in vector construction or analysis. It is further recognized that the recombination sites can be contained within the polynucleotide of interest (i.e., such as within introns, coding sequence, or untranslated regions).

In a specific embodiment, the transfer cassette further comprises at least one coding region operably linked to a promoter that drives expression in the plant cell. As discussed elsewhere herein, a recombinase is provided that recognizes and implements recombination at the recombination sites of the target site and the transfer cassette. The recombinase can be provided by any means known in the art and is described in detail elsewhere herein. In a specific embodiment, the coding region of the transfer cassette encodes a recombinase that facilitates recombination between the first and the second recombination sites of the transfer cassette and the target site, the second and the third recombination sites of the transfer cassette and the target site, or the first and the third recombination sites of the transfer cassette and the target site.

Further, the methods provide selecting at least one plant cell comprising integration of the transfer cassette at the target site. Methods for selecting plant cells with integration at the target site, such as selecting for cells expressing a selectable marker, are known in the art and are described elsewhere herein. As such, the methods further comprise recovering a fertile plant from the plant cell comprising in its genome the transfer cassette at the target site.

i. Polynucleotides of Interest

Any polynucleotide of interest (i.e., the "polypeptide of interest") may be provided to the plant cells in the transfer cassettes or target sites of the methods disclosed herein. It is recognized that any polynucleotide of interest can be provided, integrated into the plant genome at the target site by site-specific integration, and expressed in a plant. The methods disclosed herein, provide for at least 1, 2, 3, 4, 5, 6 or more polynucleotides of interest to be integrated into a specific site in the plant genome.

Various changes in phenotype are of interest, including modifying the fatty acid composition in a plant, altering the amino acid content of a plant, altering a plant's pathogen defense mechanism, and the like. These results can be achieved by providing expression of heterologous products (i.e. polynucleotides of interest) or increased expression of endogenous products in plants. Alternatively, the results can be achieved by providing for a reduction of expression of one or more endogenous products, particularly enzymes or cofactors in the plant. These changes result in a change in phenotype of the transformed plant.

In one embodiment, at least one of the first, the second, and the third polynucleotides of interest comprises a nucleotide sequence for gene silencing, a nucleotide sequence encoding a phenotypic marker, or a nucleotide sequence encoding a protein providing an agronomic advantage.

Polynucleotides of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. Polynucleotides/polypeptides of interest include, but are not limited to, herbicide-tolerance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, and oil content and/or composition. More specific polynucleotides of interest include, but are not limited to, genes that improve crop yield, polypeptides that improve desirability of crops, genes encoding proteins conferring resistance to abiotic stress, such as drought, nitrogen, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), in particular the sulfonylurea-type herbicides, genes coding for resistance to herbicides that act to inhibit the action of glutamine synthase, such as phosphinothricin or basta (e.g., the bar gene), glyphosate (e.g., the EPSP synthase gene and the GAT gene), HPPD inhibitors (e.g, the HPPD gene) or other such genes known in the art. See, for example, U.S. Pat. Nos. 7,626,077, 5,310,667, 5,866,775, 6,225,114, 6,248,876, 7,169,970, 6,867,293, and U.S. Provisional Application No. 61/401,456, each of which is herein incorporated by reference.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987)

*Eur. J. Biochem.* 165:99-106, the disclosures of which are herein incorporated by reference.

Commercial traits can also be encoded on a polynucleotide of interest that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837-5847) facilitate expression of polyhyroxyalkanoates (PHAs).

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Polynucleotides that improve crop yield include dwarfing genes, such as Rht1 and Rht2 (Peng et al. (1999) *Nature* 400:256-261), and those that increase plant growth, such as ammonium-inducible glutamate dehydrogenase. Polynucleotides that improve desirability of crops include, for example, those that allow plants to have reduced saturated fat content, those that boost the nutritional value of plants, and those that increase grain protein. Polynucleotides that improve salt tolerance are those that increase or allow plant growth in an environment of higher salinity than the native environment of the plant into which the salt-tolerant gene(s) has been introduced.

Polynucleotides/polypeptides that influence amino acid biosynthesis include, for example, anthranilate synthase (AS; EC 4.1.3.27) which catalyzes the first reaction branching from the aromatic amino acid pathway to the biosynthesis of tryptophan in plants, fungi, and bacteria. In plants, the chemical processes for the biosynthesis of tryptophan are compartmentalized in the chloroplast. See, for example, US Pub. 20080050506, herein incorporated by reference. Additional sequences of interest include Chorismate Pyruvate Lyase (CPL) which refers to a gene encoding an enzyme which catalyzes the conversion of chorismate to pyruvate and pHBA. The most well characterized CPL gene has been isolated from *E. coli* and bears the GenBank accession number M96268. See, U.S. Pat. No. 7,361,811, herein incorporated by reference.

These polynucleotide sequences of interest may encode proteins involved in providing disease or pest resistance. By "disease resistance" or "pest resistance" is intended that the plants avoid the harmful symptoms that are the outcome of the plant-pathogen interactions. Pest resistance genes may encode resistance to pests that have great yield drag such as rootworm, cutworm, European Corn Borer, and the like. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products. Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Furthermore, it is recognized that the polynucleotide of interest may also comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Pat. Nos. 5,283,184 and 5,034,323; herein incorporated by reference.

The polynucleotide of interest can also be a phenotypic marker. A phenotypic marker is screenable or a selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate(2,4-D). See for example, Yarranton, (1992) *Curr Opin Biotech* 3:506-11; Christopherson et al., (1992) *Proc. Natl. Acad. Sci. USA* 89:6314-8; Yao et al., (1992) *Cell* 71:63-72; Reznikoff, (1992) *Mol Microbiol* 6:2419-22; Hu et al., (1987) *Cell* 48:555-66; Brown et al., (1987) *Cell* 49:603-12; Figge et al., (1988) *Cell* 52:713-22; Deuschle et al., (1989) *Proc. Natl. Acad. Sci. USA* 86:5400-4; Fuerst et al., (1989) *Proc. Natl. Acad. Sci. USA* 86:2549-53; Deuschle et al., (1990) *Science* 248:480-3; Gossen, (1993) Ph.D. Thesis, University of Heidelberg; Reines et al., (1993) *Proc. Natl. Acad. Sci. USA* 90:1917-21; Labow et al., (1990) *Mol Cell Biol* 10:3343-56; Zambretti et al., (1992) *Proc. Natl. Acad. Sci. USA* 89:3952-6; Baim et al., (1991) *Proc. Natl. Acad. Sci. USA* 88:5072-6; Wyborski et al., (1991) *Nucleic Acids Res* 19:4647-53; Hillen and Wissman, (1989) *Topics Mol Struc Biol* 10:143-62; Degenkolb et al., (1991) *Antimicrob Agents Chemother* 35:1591-5; Kleinschnidt et al., (1988) *Biochemistry* 27:1094-104; Bonin, (1993) Ph.D. Thesis, University of Heidelberg; Gossen et al., (1992) *Proc. Natl. Acad. Sci. USA* 89:5547-51; Oliva et al., (1992) *Antimicrob Agents Chemother* 36:913-9; Hlavka et al., (1985) *Handbook of Experimental Pharmacology*, Vol. 78 (Springer-Verlag, Berlin); Gill et al., (1988) *Nature* 334:721-4.

Active variants or fragments of polynucleotides/polypeptides of interest are also provided. Such active variants can comprise at least 65%, 70%, 75%, 80%, 85%, 90%, 91%, 92%, 93%, 94%, 95%, 96%, 97%, 98%, 99% or more sequence identity to the native polynucleotide/polypeptide of interest, wherein the active variants retain the biological activity of the native polynucleotide/polypeptide.

C. Site-Specific Recombination System

A site-specific recombination system can be employed in a variety of ways to manipulate the target site that has been integrated at the recognition site. The site-specific recombination system employs various components which are described in detail below and in U.S. Pat. Nos. 6,187,994, 6,262,341, 6,331,661 and 6,300,545, each of which is herein incorporated by reference.

Various recombination sites can be employed in the methods and compositions provided herein (i.e. in the various target sites or transfer cassettes disclosed herein). By "recombination site" is intended a naturally occurring recombination site and active variants thereof. Many recombination systems are known in the art and one of skill will recognize the appropriate recombination site to be used with the recombination system of interest. As discussed in greater detail elsewhere herein, various combinations of recombination sites can be employed including, sets of dissimilar sites and corresponding recombination sites and/or dissimilar and non-recombinogenic sites can be used in the various methods provided herein. Accordingly, any suitable recombination site or set of recombination sites may be utilized herein, including a FRT site, a biologically active variant of a FRT site (i.e. a mutant FRT site), a LOX site, a biologically active variant of a LOX site (i.e. a mutant LOX site), any combination thereof, or any other combination of recombination sites known in the art. Examples of FRT sites include, for example, the wild type FRT site (FRT1, SEQ ID NO: 9), and various mutant FRT sites, including but not limited to, FRT5 (SEQ ID NO: 10), FRT6 (SEQ ID NO: 11), FRT12 (SEQ ID NO: 12) and FRT87 (SEQ ID NO: 13). See, for example, U.S. Pat. No. 6,187,994.

Recombination sites from the Cre/Lox site-specific recombination system can also be used. Such recombination sites include, for example, wild type LOX sites and mutant LOX sites. An analysis of the recombination activity of mutant LOX sites is presented in Lee et al. (1998) *Gene* 216:55-65, herein incorporated by reference. Also, see for example, Schlake and Bode (1994) *Biochemistry* 33:12746-12751; Huang et al. (1991) *Nucleic Acids Research* 19:443-448; Sadowski (1995) In *Progress in Nucleic Acid Research and Molecular Biology* Vol. 51, pp. 53-91; Cox (1989) In *Mobile DNA*, Berg and Howe (eds) American Society of Microbiology, Washington D.C., pp. 116-670; Dixon et al. (1995) *Mol. Microbiol.* 18:449-458; Umlauf and Cox (1988) *EMBO* 7:1845-1852; Buchholz et al. (1996) *Nucleic Acids Research* 24:3118-3119; Kilby et al. (1993) *Trends Genet.* 9:413-421; Rossant and Geagy (1995) *Nat. Med.* 1: 592-594; Albert et al. (1995) *The Plant J.* 7:649-659; Bayley et al. (1992) *Plant Mol. Biol.* 18:353-361; Odell et al. (1990) *Mol. Gen. Genet.* 223:369-378; Dale and Ow (1991) *Proc. Natl. Acad. Sci. USA* 88:10558-10562; Qui et al. (1994) *Proc. Natl. Acad. Sci. USA* 91:1706-1710; Stuurman et al. (1996) *Plant Mol. Biol.* 32:901-913; Dale et al. (1990) *Gene* 91:79-85; Albert et al. (1995) *The Plant J.* 7:649-659 and WO 01/00158; all of which are herein incorporated by reference.

Active variants and fragments of recombination sites (i.e SEQ ID NOS: 9-13) are also encompassed by the compositions and methods provided herein. Fragments of a recombination site retain the biological activity of the recombination site and hence facilitate a recombination event in the presence of the appropriate recombinase. Thus, fragments of a recombination site may range from at least about 5, 10, 15, 20, 25, 30, 35, 40 nucleotides, and up to the full-length of a recombination site. Active variants can comprise at least 65%, 70%, 75%, 80%, 85%, 90%, 91%, 92%, 93%, 94%, 95%, 96%, 97%, 98%, 99% or more sequence identity to the native recombination site, wherein the active variants retain biological activity and hence facilitate a recombination event in the presence of the appropriate recombinase. Assays to measure the biological activity of recombination sites are known in the art. See, for example, Senecoll et al. (1988) *J. Mol. Biol.* 201:406-421; Voziyanov et al. (2002) *Nucleic Acid Research* 30:7, U.S. Pat. No. 6,187,994, WO/01/00158, and Albert et al. (1995) *The Plant Journal* 7:649-659.

Recombinases are also employed in the methods and compositions provided herein. By "recombinase" is intended a native polypeptide that catalyzes site-specific recombination between compatible recombination sites. For reviews of site-specific recombinases, see Sauer (1994) *Current Opinion in Biotechnology* 5:521-527; and Sadowski (1993) *FASEB* 7:760-767; the contents of which are incorporated herein by reference. The recombinase used in the methods can be a naturally occurring recombinase or a biologically active fragment or variant of the recombinase. Recombinases useful in the methods and compositions include recombinases from the Integrase and Resolvase families, biologically active variants and fragments thereof, and any other naturally occurring or recombinantly produced enzyme or variant thereof that catalyzes conservative site-specific recombination between specified DNA recombination sites.

The Integrase family of recombinases has over one hundred members and includes, for example, FLP, Cre, Int, and R. For other members of the Integrase family, see for example, Esposito et al. (1997) *Nucleic Acid Research* 25:3605-3614 and Abremski et al. (1992) *Protein Engineering* 5:87-91, both of which are herein incorporated by reference. Other recombination systems include, for example, the streptomycete bacteriophage phi C31 (Kuhstoss et al. (1991) *J. Mol. Biol.* 20:897-908); the SSV1 site-specific recombination system from *Sulfolobus shibatae* (Maskhelishvili et al. (1993) *Mol. Gen. Genet.* 237:334-342); and a retroviral integrase-based integration system (Tanaka et al. (1998) *Gene* 17:67-76). In other embodiments, the recombinase is one that does not require cofactors or a supercoiled substrate. Such recombinases include Cre, FLP, or active variants or fragments thereof (SEQ ID NOS: 15, 21, 26).

The FLP recombinase is a protein that catalyzes a site-specific reaction that is involved in amplifying the copy number of the two-micron plasmid of *S. cerevisiae* during DNA replication. As used herein, FLP recombinase refers to a recombinase that catalyzes site-specific recombination between two FRT sites. The FLP protein has been cloned and expressed. See, for example, Cox (1993) *Proc. Natl. Acad. Sci. U.S.A.* 80:4223-4227. The FLP recombinase for use in the methods and with the compositions may be derived from the genus *Saccharomyces*. One can also synthesize a polynucleotide comprising the recombinase using plant-preferred codons for optimal expression in a plant of interest. A recombinant FLP enzyme encoded by a nucleotide sequence comprising maize preferred codons (FLPm) that catalyzes site-specific recombination events is known. See, for example, U.S. Pat. No. 5,929,301, herein incorporated by reference. Additional functional variants and fragments of FLP are known. See, for example, Buchholz et al. (1998) *Nat. Biotechnol.* 16:617-618, Hartung et al. (1998) *J. Biol. Chem.* 273:22884-22891, Saxena et al. (1997) *Biochim Biophys Acta* 1340(2):187-204, and Hartley et al. (1980) *Nature* 286:860-864, all of which are herein incorporated by reference.

The bacteriophage recombinase Cre catalyzes site-specific recombination between two lox sites. The Cre recombinase is known in the art. See, for example, Guo et al. (1997) *Nature* 389:40-46; Abremski et al. (1984) *J. Biol. Chem.* 259:1509-1514; Chen et al. (1996) *Somat. Cell Mol. Genet.* 22:477-488; Shaikh et al. (1977) *J. Biol. Chem.* 272:5695-5702; and, Buchholz et al. (1998) *Nat. Biotechnol.* 16:617-618, all of which are herein incorporated by reference. The Cre polynucleotide sequences may also be synthesized using plant-preferred codons. Such sequences (mo-Cre) are described in WO 99/25840, herein incorporated by reference and set forth in SEQ ID NO: 21.

It is further recognized that a chimeric recombinase can be used in the methods. By "chimeric recombinase" is intended a recombinant fusion protein which is capable of catalyzing site-specific recombination between recombination sites that originate from different recombination systems. That is, if a set of functional recombination sites, characterized as being dissimilar and non-recombinogenic with respect to one another, is utilized in the methods and compositions and comprises a FRT site and a LoxP site, a chimeric FLP/Cre recombinase or active variant or fragment thereof will be needed or, alternatively, both recombinases may be separately provided. Methods for the production and use of such chimeric recombinases or active variants or fragments thereof are described in WO 99/25840, herein incorporated by reference.

By utilizing various combinations of recombination sites in the target sites and the transfer cassettes provided herein, the methods provide a mechanism for the site-specific integration of polynucleotides of interest into a specific site in the plant genome. The methods also allow for the subsequent insertion of additional polynucleotides of interest into the specific genomic site.

In one embodiment, providing the recombinase comprises integrating into the genome of the plant cell a nucleotide sequence encoding the recombinase. In a specific embodiment, the recombinase is FLP. In yet another embodiment, the FLP recombinase is synthesized using maize-preferred codons.

As used herein, by "providing" is intended any method that allows for an amino acid sequence and/or a polynucleotide to be brought together with the recited components. A variety of methods are known in the art for the introduction of nucleotide sequence into a plant. Any means can be used to bring together the various components of the recombination system (i.e., the target site, transfer cassette, and the appropriate recombinase), including, for example, transformation and sexual crossing. See, also, WO99/25884 herein incorporated by reference. In addition, as discussed elsewhere herein, the recombinase may also be provided by the introduction of the polypeptide or mRNA into the cell.

Active variants and fragments of recombinases (i.e FLP or Cre) are also encompassed by the compositions and methods provided herein. Such active variants can comprise at least 65%, 70%, 75%, 80%, 85%, 90%, 91%, 92%, 93%, 94%, 95%, 96%, 97%, 98%, 99% or more sequence identity to the native recombinase, wherein the active variants retain biological activity and hence implement a recombination event. Assays for recombinase activity are known and generally measure the overall activity of the enzyme on DNA substrates containing recombination sites. For example, to assay for FLP activity, inversion of a DNA sequence in a circular plasmid containing two inverted FRT sites can be detected as a change in position of restriction enzyme sites. This assay is described in Vetter et al. (1983) *PNAS* 80:7284. Alternatively, excision of DNA from a linear molecule or intermolecular recombination frequency induced by the enzyme may be assayed, as described, for example, in Babineau et al. (1985) *Journal of Biological Chemistry* 260:12313; Meyer-Leon et al. (1987) *Nucleic Acid Res* 15:6469; and Gronostajski et al. (1985) *Journal of Biological Chemistry* 260:12328. Alternatively, recombinase activity may also be assayed by excision of a sequence flanked by recombinogenic FRT sites that upon removal will activate an assayable marker gene.

D. Methods of Manipulating the Target Site Integrated into the Genome

As discussed above, various methods can be used to insert polynucleotides of interest into the target site in a plant or plant cell. Non-limiting examples of various DNA constructs, target sites, and transfer cassettes that can be used to insert a polynucleotide of interest into a plant or plant cell are set forth in Table 2. In each of the examples presented in Table 2, once the target site has integrated into the recognition site or once the transfer cassette has integrated into the target site, the appropriate selective agent can be employed to identify the plant cell having the desired DNA construct.

Once a target site has been established within the genome, additional recombination sites may be introduced by incorporating such sites within the nucleotide sequence of the transfer cassette. Thus, once a target site has been established, it is possible to subsequently add or alter sites through recombination. Such methods are described in detail in WO 99/25821, herein incorporated by reference.

In one embodiment, multiple genes or polynucleotides of interest can be stacked at the target site in the genome of the plant. For example, as illustrated in Table 1, scheme D, the target site integrated at the recognition site can comprise the following components: RSF1::P1::R1::S1::T1-P2::NT1::T2-P3::R2-R3::RSF2, where RSF is a fragment of the recognition site, P is a promoter active in a plant, R is a recombination site, S is the selection marker, T is a termination region, and NT is a polynucleotide of interest. The following transfer cassette comprising the following components could be introduced: R2::S2::T3-P4::NT2::T4-R3. The plant with this transfer cassette integrated at the target site, can then be selected for based on the second selection marker. In this manner, multiple sequences can be stacked at predetermined locations in the target site. Various alterations can be made to the stacking method described above and still achieve the desired outcome of having the polynucleotides of interest stacked in the genome of the plant.

TABLE 2

Non-Limiting Examples of Various Integrated Target Sites, Transfer Cassettes, and Integrated Transfer Cassettes

| | Target site integrated at the recognition site | | Transfer cassette | | Transfer cassette integrated at the target site |
|---|---|---|---|---|---|
| A | RSF1-P1::R1::NT1::T1-R2-RSF2 | X | R1::S1::T2-R2 | → | RSF1-P1::R1::S1::T2-R2-RSF2 |
| B | RSF1-P1::R1::NT1::T1-R2-RSF2 | X | R1::S1::T2-P2::NT2::T3-R2 | → | RSF1-P1::R1::S1-T2-P2::NT2::T3::R2-RSF2 |
| C | RSF1-P1::R1::NT1::T1-R2-RSF2 | X | R1::S1::T2-P2::NT2::T3-P3::R2-R3 | → | RSF1-P1::R1::S1::T2-P2::NT2::T3-P3::R2::R3-RSF2 |
| D | RSF1-P1::R1::S1::T1-P2::NT1::T2-P3::R2-R3-RSF2 | X | R2::S2::T3-P4::NT2::T4-R3 | → | RSF1-P1::R1::S1::T1-P2::NT1::T2-P3::R2::S2::T3-P4::NT2::T4-R3-RSF2 |

RSF = recognition site fragment;
P = promoter active in a plant;
R = recombination site;
S = selection marker;
T = terminator region;
NT = polynucleotide of interest; the symbol :: implies a fusion between adjacent elements and implies that the sequences are put together to generate an inframe fusion that results in a properly expressed and functional gene product.

IV. Methods of Introducing Sequences

As outlined above, methods and compositions provided herein combine an endonuclease integration system with a site-specific recombinase system which allow for improved methods and compositions for the targeted insertion of a sequence of interest in the genome of a plant. Such systems employ a variety of components and for ease of reference, herein the term "site-specific integration system" generically refers to all the components of the endonuclease integration system (i.e. the various endonucleases, recognition sites, target sites, donor DNA or any active variants or fragments thereof provided herein) and the site-specific recombination system (i.e. the various transfer cassettes, site-specific recombination sites, site-specific recombinases, polynucleotides of interest or any active variants or fragments thereof provided herein).

The methods provided herein comprise introducing into a plant cell, plant or seed a polynucleotide or polypeptide construct comprising the various components of the site-specific integration system provided herein.

The methods provided herein do not depend on a particular method for introducing any component of the site-specific integration system into the host cell, only that the polynucleotide gains access to the interior of a least one cell of the host. Methods for introducing polynucleotides into host cells (i.e. plants) are known in the art and include, but are not limited to, stable transformation methods, transient transformation methods, and virus-mediated methods.

By "introducing" is intended presenting to the plant the sequence (polypeptide or polynucleotide) in such a manner that the sequence gains access to the interior of a cell of the plant. The methods provided herein do not depend on a particular method for introducing a sequence into a plant, only that the polynucleotide or polypeptide gains access to the interior of at least one cell of the plant. Methods for introducing sequences into plants are known in the art and include, but are not limited to, stable transformation methods, transient transformation methods, virus-mediated methods, and sexual breeding. Thus, "introduced" in the context of inserting a nucleic acid fragment (e.g., various components of the site-specific integration system provided herein) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

In some embodiments, the plant cells, plants and seeds employed in the methods and compositions have a DNA construct stably incorporated into their genome. By "stably incorporated" or "stably introduced" is intended the introduction of a polynucleotide into the plant such that the nucleotide sequence integrates into the genome of the plant and is capable of being inherited by progeny thereof. Any protocol may be used for the stable incorporation of the DNA constructs or the various components of the site-specific integration system employed herein.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Led transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In other embodiments, any of the polynucleotides employed herein may be introduced into plants by contacting plants with a virus or viral nucleic acids. Generally, such methods involve incorporating a desired polynucleotide within a viral DNA or RNA molecule. It is recognized that a sequence employed in the methods or compositions provided herein may be initially synthesized as part of a viral polyprotein, which later may be processed by proteolysis in vivo or in vitro to produce the desired recombinant protein. Further, it is recognized that promoters employed herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

In other embodiments, various components of the site-specific integration system can be provided to a plant using a variety of transient transformation methods. "Transient transformation" is intended to mean that a polynucleotide is introduced into the host (i.e., a plant) and expressed temporally. Such transient transformation methods include, but are not limited to, the introduction of any of the components of the site-specific integration system or active fragments or variants thereof directly into the plant or the introduction of the transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylamine (PEI; Sigma #P3143).

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, transformed seed (also referred to as "transgenic seed") having the recited DNA construct stably incorporated into their genome is provided.

V. Plants

Compositions provided herein encompass a plant cell, a plant, a plant part, and a seed comprising any of the components, or combination thereof, of the site-specific integration system disclosed herein (i.e. an endonuclease, a recognition site, a target site, a donor DNA, a transfer cassette, various site-specific recombination sites, site-specific recombinases, polynucleotides of interest, or any active variants or fragments thereof).

In one embodiment, a plant cell, a plant, a plant part and/or a seed is provided comprising a target site for site-specific integration integrated at the recognition site.

The compositions further provide a plant cell, a plant, a plant part and a seed comprising a transfer cassette integrated at the target site. In one embodiment, the plant cell, a plant, a plant part and a seed having the target site integrated at the recognition site comprises a target site comprising in the following order, a first recombination site, a second recombination site and wherein the first and the second recombination sites are dissimilar and non-recombinogenic with respect to one another. The target site can further comprise a polynucleotide of interest between the first and the second recombination sites. As described elsewhere herein, the recombination sites can be any combination of recombination sites known in the art. For example, the recombination sites can be a FRT site, a mutant FRT site, a LOX site or a mutant LOX site.

In specific embodiments, the target site of the plant cell, plant, plant part and seed further comprises a third recombination site between the first and the second recombination site, wherein the third recombination site is dissimilar and non-recombinogenic to the first and the second recombination sites. The first, second, and third recombination sites can comprise, for example, FRT1, FRT5, FRT6, FRT12, or FRT87. Also, provided is a plant cell, plant, or seed wherein the first recombination site is FRT1, the second recombination site is FRT12 and the third recombination site is FRT87.

The plant cell, a plant, a plant part and a seed can comprise any of the recognition sites provided herein. For example, the recognition site can be selected from the group consisting of SEQ ID NO:1-8, 16 and 20 or an active variant thereof.

As used herein, the term plant includes plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included herein, provided that these parts comprise the recited DNA construct.

A transformed plant or transformed plant cell provided herein is one in which genetic alteration, such as transformation, has been affected as to a gene of interest, or is a plant or plant cell which is descended from a plant or cell so altered and which comprises the alteration. A "transgene" is a gene that has been introduced into the genome by a transformation procedure. Accordingly, a "transgenic plant" is a plant that contains a transgene, whether the transgene was introduced into that particular plant by transformation or by breeding; thus, descendants of an originally-transformed plant are encompassed by the definition. A "control" or "control plant" or "control plant cell" provides a reference point for measuring changes in phenotype of the subject plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which does not express the transgene, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the transgene; or (e) the subject plant or plant cell itself, under conditions in which the construct is not expressed.

Plant cells that have been transformed to have a component(s) of the site-specific integration system provided herein can be grown into whole plants. The regeneration, development, and cultivation of plants from single plant protoplast transformants or from various transformed explants is well known in the art. See, for example, McCormick et al. (1986) *Plant Cell Reports* 5:81-84; Weissbach and Weissbach, In: Methods for Plant Molecular Biology, (Eds.), Academic Press, Inc. San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. Two or more generations may be grown to ensure that expression of the desired phenotypic characteristic is stably maintained and inherited and then seeds harvested to ensure expression of the desired phenotypic characteristic has been achieved. In this manner, the compositions presented herein provide transformed seed (also referred to as "transgenic seed") having a polynucleotide provided herein, for example, a target site, stably incorporated into their genome.

The components of the site-specific integration system provided herein may be used for transformation of any plant species, including, but not limited to, monocots and dicots. Examples of plant species of interest include, but are not limited to, corn (maize) (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

It is recognized that the plant having stably incorporated the DNA construct can be further characterized for site-specific integration potential, agronomic potential, and copy number. See, U.S. Pat. No. 6,187,994.

Depending on the polynucleotide(s) of interest incorporated into the target site, the transgenic plants, plant cells, or seeds comprising a target site with a polynucleotide(s) of interest provided herein may have a change in phenotype, including, but not limited to, an altered pathogen or insect defense mechanism, an increased resistance to one or more herbicides, an increased ability to withstand stressful environmental conditions, a modified ability to produce starch, a modified level of starch production, a modified oil content and/or composition, a modified carbohydrate content and/or composition, a modified fatty acid content and/or composition, a modified ability to utilize, partition and/or store nitrogen, and the like.

VI. Polynucleotides

Provided herein are polynucleotides or nucleic acid molecules comprising the various components of the site-specific integration system (i.e. an endonuclease, a recognition site, a target site, a donor DNA, a transfer cassette, various site-specific recombination sites, site-specific recombinases, polynucleotides of interest or any active variants or fragments thereof). Also provided are nucleic acid molecules comprising any of the various target sites provided herein integrated at the recognition site in the plant genome.

The terms "polynucleotide," "polynucleotide sequence," "nucleic acid sequence," and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides provided herein also encompass all forms of sequences including, but not limited to, single-stranded forms, double-stranded forms, hairpins, stem-and-loop structures, and the like.

The compositions provided herein can comprise an isolated or substantially purified polynucleotide. An "isolated" or "purified" polynucleotide is substantially or essentially free from components that normally accompany or interact with the polynucleotide as found in its naturally occurring environment. Thus, an isolated or purified polynucleotide is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived.

Further provided are recombinant polynucleotides comprising the various components of the site-specific integration system. The terms "recombinant polynucleotide" and "recombinant DNA construct" are used interchangeably herein. A recombinant construct comprises an artificial or heterologous combination of nucleic acid sequences, e.g., regulatory and coding sequences that are not found together in nature. For example, a transfer cassette can comprise restriction sites and a heterologous polynucleotide of interest. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments provided herein. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

In specific embodiments, one or more of the components of the site-specific integration system described herein can be provided in an expression cassette for expression in a plant or other organism or cell type of interest. The cassette can include 5' and 3' regulatory sequences operably linked to a polynucleotide provided herein. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of a recombinant polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a recombinant polynucleotide provided herein, and a transcriptional and translational termination region (i.e., termination region) functional in plants. The regulatory regions (i.e., promoters, transcriptional regulatory regions, and translational termination regions) and/or a polynucleotide provided herein may be native/analogous to the host cell or to each other. Alternatively, the regulatory regions and/or a polynucleotide provided herein may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, the regulatory regions and/or a recombinant polynucleotide provided herein may be entirely synthetic.

The termination region may be native with the transcriptional initiation region, may be native with the operably linked recombinant polynucleotide, may be native with the plant host, or may be derived from another source (i.e., foreign or heterologous) to the promoter, the recombinant polynucleotide, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

In preparing the expression cassette, the various DNA fragments may be manipulated, so as to provide for the DNA sequences in the proper orientation. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the expression cassettes provided herein. The promoters can be selected based on the desired outcome. It is recognized that different applications can be enhanced by the use of different promoters in the expression cassettes to modulate the timing, location and/or level of expression of the polynucleotide of interest. Such expression constructs may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

In some embodiments, an expression cassette provided herein can be combined with constitutive, tissue-preferred, or other promoters for expression in plants. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. If low level expression is desired, weak promoter(s) may be used. Weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the ERE promoter which is estrogen induced, and the Axig1 promoter which is auxin induced and tapetum specific but also active in callus (PCT US01/22169).

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A. et al. (1986) *Plant Sci.* 47:95-102; Reina, M. et al. *Nucl. Acids Res.* 18(21):6426; and Kloesgen, R. B. et al. (1986) *Mol. Gen. Genet.* 203:237-244. Promoters that express in the embryo, pericarp, and endosperm are disclosed in U.S. Pat. No. 6,225,529 and PCT publication WO 00/12733. The disclosures for each of these are incorporated herein by reference in their entirety.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of a polynucleotide of interest within a particular plant tissue. Tissue-preferred promoters are known in the art. See, for example, Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590. In addition, the promoters of cab and rubisco can also be used. See, for example, Simpson et al. (1958) *EMBO J* 4:2723-2729 and Timko et al. (1988) *Nature* 318:57-58.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing non-legume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed roIC and roID root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and roIB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179. The phaseolin gene (Murai et al. (1983) *Science* 23:476-482 and Sengopta-Gopalen et al. (1988) *PNAS* 82:3320-3324.

The expression cassette containing the polynucleotides provided herein can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate(2,4-D) and sulfonylureas. Additional selectable markers include phenotypic markers such as beta-galactosidase and fluorescent proteins such as green fluorescent protein (GFP) (Su et al. (2004) *Biotechnol. Bioeng.* 85:610-9 and Fetter et al. (2004) *Plant Cell* 16:215-28), cyan fluorescent protein (CYP) (Bolte et al. (2004) *J. Cell Science* 117:943-54 and Kato et al. (2002) *Plant Physiol.* 129:913-42), and yellow fluorescent protein (PhiYFP™ from Evrogen; see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) Handbook of Experimental Pharmacology, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the compositions presented herein.

Where appropriate, the sequences employed in the methods and compositions (i.e., the polynucleotide of interest, the recombinase, the endonuclease, etc.) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

VII. Fragments, Variants and Sequence Comparisons

The methods and compositions provided herein employ a variety of different components of the site-specific integration system (i.e. an endonuclease, a recognition site, a target site, a donor DNA, a transfer cassette, various site-specific recombination sites, site-specific recombinases, polynucleotides of interest or any active variants or fragments thereof). It is recognized throughout the description that some components of the site-specific integration system can have active variants and fragments. Such components include, for example, endonucleases (i.e. engineered endonucleases), endonuclease recognition sites (i.e. SEQ ID NOS: 1-8, 16, 120), recombinases (i.e. SEQ ID NOS: 15, 21, 26), recombination sites (i.e. SEQ ID NO: 9-13), and polynucleotides of interest. Biological activity for each of these components is described elsewhere herein.

Fragments and variants of the endonucleases, endonuclease recognition sites, recombinases, recombination sites, and polynucleotides of interest are also encompassed herein. By "fragment" is intended a portion of the polynucleotide or a portion of the amino acid sequence and hence protein encoded thereby. Fragments of a polynucleotide may encode protein fragments that retain the biological activity of the native protein (i.e., a fragment of a recombinase implements a recombination event). As used herein, a "native" polynucleotide or polypeptide comprises a naturally occurring nucleotide sequence or amino acid sequence, respectively. Thus, fragments of a polynucleotide may range from at least about 20 nucleotides, about 50 nucleotides, about 100 nucleotides, and up to the full-length polynucleotide. A fragment of a polynucleotide that encodes a biologically active portion of a protein employed in the methods or compositions will encode at least 15, 25, 30, 50, 100, 150, 200, or 250 contiguous amino acids, or up to the total number of amino acids present in a full-length protein. Alternatively, fragments of a polynucleotide that are useful as a hybridization probe generally do not encode fragment proteins retaining biological activity. Thus, fragments of a nucleotide sequence may range from at least about 10, 20, 30, 40, 50, 60, 70, 80 nucleotides or up to the full length sequence.

A biologically active portion of a polypeptide can be prepared by isolating a portion of one of the polynucleotides encoding the portion of the polypeptide of interest and expressing the encoded portion of the protein (e.g., by recombinant expression in vitro), and assessing the activity of the portion of the polypeptide. For example, polynucleotides that encode fragments of a recombinase polypeptide can comprise nucleotide sequence comprising at least 16, 20, 50, 75, 100, 150, 200, 250, 300, 350, 400, 450, 500, 550, 600, 650, 700, 800, 900, 1,000, 1,100, 1,200, 1,300, or 1,400 nucleotides, or up to the number of nucleotides present in a nucleotide sequence employed in the methods and compositions provided herein.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. For polynucleotides, conservative variants include those sequences that, because of the degeneracy of the genetic code, encode the amino acid sequence of one of the polypeptides employed in the compositions and methods provided herein. Naturally occurring allelic variants such as these, or naturally occurring allelic variants of polynucleotides can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis. Generally, variants of a particular polynucleotide employed in the methods and compositions provided herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular polynucleotide employed in the methods and compositions provided herein (i.e., endonucleases, endonuclease recognition sites, recombinases, recombination sites, and polynucleotides of interest) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide are disclosed. Percent sequence identity between any two polypeptides can be calculated using sequence alignment programs and parameters described elsewhere herein. Where any given pair of polynucleotides provided herein is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins employed in the methods and compositions provided herein are biologically active, that is they continue to possess the desired biological activity of the native protein. Such variants may result from, for example, genetic polymorphism or from human manipulation. Biologically active variants of a native protein provided herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein provided herein may differ from that protein by as few as 1-15 amino acid residues, as few as 1-10, such as 6-10, as few as 5, as few as 4, 3, 2, or even 1 amino acid residue.

Proteins may be altered in various ways including amino acid substitutions, deletions, truncations, and insertions. Methods for such manipulations are generally known in the art. For example, amino acid sequence variants of the recombinase proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the polynucleotides used herein can include the naturally occurring sequences, the "native" sequences, as well as mutant forms. Likewise, the proteins used in the methods provided herein encompass both naturally occurring proteins as well as variations and modified forms thereof. Obviously, the mutations that will be made in the polynucleotide encoding the variant polypeptide must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays.

Variant polynucleotides and proteins also encompass sequences and proteins derived from a mutagenic and recombinogenic procedure such as DNA shuffling. With such a procedure, for example, one or more different recombinase coding sequences can be manipulated to create a new recombinase protein possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The following terms are used to describe the sequence relationships between two or more nucleic acids or polynucleotides. As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Sequence relationships can be analyzed and described using computer-implemented algorithms. The sequence relationship between two or more polynucleotides, or two or more polypeptides can be determined by determining the best alignment of the sequences, and scoring the matches and the gaps in the alignment, which yields the percent sequence identity, and the percent sequence similarity. Polynucleotide relationships can also be described based on a comparison of the polypeptides each encodes. Many programs and algorithms for the comparison and analysis of sequences are well-known in the art.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff (1989) *Proc. Natl. Acad. Sci USA* 89:10915); or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Non-limiting examples of methods and compositions disclosed herein are as follows:

1. A method for introducing into the genome of a plant cell a target site for site-specific integration, the method comprising:

(a) providing a plant cell comprising in its genome an endogenous recognition site for an engineered endonuclease, wherein the engineered endonuclease is capable of inducing a double-strand break in said endogenous recognition site, and wherein the endogenous recognition site is located between a first and a second genomic region;

(b) providing a donor DNA comprising the target site for site-specific integration located between a first region of homology to said first genomic region and a second region of homology to said second genomic region, wherein the target site comprises a first and a second recombination site, wherein the first and the second recombination sites are dissimilar and non-recombinogenic with respect to one another;

(c) contacting the plant cell with the donor DNA and the engineered endonuclease, and (d) identifying at least one plant cell from (c) comprising in its genome the target site integrated at the endogenous recognition site.

2. The method of embodiment 1, wherein the first region of homology further comprises a first fragment of said endogenous recognition site of (a), and wherein the second region of homology comprises a second fragment of said endogenous recognition site of (a), wherein the first and second fragments are dissimilar.

3. The method of embodiment 1, wherein the first region of homology further comprises the first 13 bases of said endogenous recognition site of (a), and wherein the second region of homology comprises the last 9 bases of said endogenous recognition site of (a).

4. The method of any one of embodiments 1-3, further comprising recovering a fertile plant from the cell of (d), the fertile plant comprising in its genome the target site integrated into the endogenous recognition site.

5. The method of any one of embodiments 1-4, wherein the endogenous recognition site is selected from the group consisting of SEQ ID NO:1-8, 16 and 20 or a sequence having at least 90% sequence identity to SEQ ID NO:1-8, 16 and 20.

6. The method of any one of embodiments 1-5, wherein the target site further comprises a polynucleotide of interest between the first recombination site and the second recombination site.

7. The method of any one of embodiments 1-6, wherein at least one of the first and the second recombination sites comprises an FRT site, a mutant FRT site, a LOX site, and a mutant LOX site.

8. The method of any one of embodiments 1-7, wherein the target site further comprises a third recombination site between the first and the second recombination site, wherein the third recombination site is dissimilar and non-recombinogenic to the first and the second recombination sites.

9. The method of embodiment 8, wherein at least one of the first, the second, and the third recombination sites comprises FRT1 (SEQ ID NO: 9), FRT 5 (SEQ ID NO: 10), FRT6 (SEQ ID NO: 11), FRT12 (SEQ ID NO: 12) and FRT87 (SEQ ID NO: 13).

10. The method of embodiment 8, wherein the first recombination site is FRT1 (SEQ ID NO: 9), the second recombination site is FRT12 (SEQ ID NO: 12), and the third recombination site is FRT87 (SEQ ID NO: 13).

11. The method of any one of embodiments 1-10, wherein the engineered endonuclease is derived from I-CreI.

12. The method of any one of embodiments 1-11, wherein said plant cell is from a monocot.

13. The method of embodiment 12, wherein said monocot is maize, wheat, rice, barley, sorghum, or rye.

14. The method of any one of embodiments 1-11, wherein said plant cell is from a dicot.

15. The method of embodiment 14, wherein said dicot is soybean, Brassica, sunflower, cotton, or alfalfa.

16. A plant cell, plant part, plant, or seed comprising the target site integrated at the endogenous recognition site according to any one of embodiments 1-15.

17. A nucleic acid molecule comprising the target site integrated at the endogenous recognition site according to any one of embodiments 1-15.

18. A plant cell, plant part, plant, or seed comprising the nucleic acid molecule of embodiment 17.

19. A method of integrating a polynucleotide of interest into a target site in the genome of a plant cell, the method comprising:

(a) providing at least one plant cell comprising in its genome a target site for site-specific integration, wherein the target site is integrated into an endogenous recognition site for an engineered endonuclease, and wherein the target site is, (i) a target site comprising a first and a second recombination site; or, (ii) the target site of (i) further comprising a third recombination site between the first recombination site and the second recombination site, wherein the engineered endonuclease is capable of inducing a double-strand break in the endogenous recognition site, wherein the first, the second, and the third recombination sites are dissimilar and non-recombinogenic with respect to one another, (b) introducing into the plant cell of (a) a transfer cassette comprising, (iii) the first recombination site, a first polynucleotide of interest, and the second recombination site, (iv) the second recombination site, a second polynucleotide of interest, and the third recombination sites, or (v) the first recombination site, a third polynucleotide of interest, and the third recombination sites;

(c) providing a recombinase that recognizes and implements recombination at the first and the second recombination sites, at the second and the third recombination sites, or at the first and third recombination sites; and (d) selecting at least one plant cell comprising integration of the transfer cassette at the target site.

20. The method of embodiment 19, further comprising recovering a fertile plant from the plant cell of (d), the fertile plant comprising in its genome the transfer cassette at the target site.

21. The method of any one of any one of embodiments 19-20, wherein at least one of the first, the second, and the third polynucleotides of interest comprises a nucleotide sequence for gene silencing, a nucleotide sequence encoding a phenotypic marker, or a nucleotide sequence encoding a protein providing an agronomic advantage.

22. The method of any one of embodiments 19-21, wherein providing the recombinase comprises integrating into the genome of the plant cell a nucleotide sequence encoding the recombinase.

23. The method of any one of embodiment 19-22, wherein the transfer cassette further comprises at least one coding region operably linked to a promoter that drives expression in the plant cell.

24. The method of any one of embodiments 19-23, wherein the transfer cassette further comprises a coding region operably linked to a promoter that drives expression in the plant cell, wherein the coding region encodes a recombinase that facilitates recombination between, the first and the second recombination sites of the transfer cassette and the target site, the second and the third recombination sites of the transfer cassette and the target site, or the first and the third recombination sites of the transfer cassette and the target site.

25. The method of any one of embodiment 19-24, wherein at least one of the first, the second, and the third recombination sites comprises an FRT site, a mutant FRT site, a LOX site, or a mutant LOX site.

26. The method of any one of embodiments 19-24, wherein the first recombination site is FRT1 (SEQ ID NO:

9), the second recombination site is FRT12 (SEQ ID NO: 12), and the third recombination site is FRT87 (SEQ ID NO: 13).

27. The method of any one of embodiments 19-26, wherein the recombinase is FLP.

28. The method of embodiment 27, wherein the FLP has been synthesized using maize-preferred codons.

29. The method of any one of embodiments 19-28, wherein said plant cell is from a monocot.

30. The method of embodiment 29, wherein said monocot is maize, wheat, rice, barley, sorghum, or rye.

31. The method of any one of embodiments 19-28 wherein said plant cell is from a dicot.

32. The method of embodiment 31, wherein said dicot is soybean, Brassica, sunflower, cotton, or alfalfa.

33. A plant cell, plant part, plant, or seed comprising the transfer cassette integrated at the target site according to any one of embodiments 19-32.

34. A plant, seed or plant cell comprising in its genome a target site for site-specific integration, wherein the target site is integrated into an endogenous recognition site for an engineered endonuclease, wherein the target site comprises in the following order:
 (a) a first recombination site;
 (b) a second recombination site, and
wherein the engineered endonuclease is capable of inducing a double-strand break at the endogenous recognition site, wherein the first and the second recombination sites are dissimilar and non-recombinogenic with respect to one another.

35. The plant, seed or plant cell of embodiment 34, wherein the endogenous recognition site is selected from the group consisting of SEQ ID NO:1-8, 16 and 20 or a sequence having at least 90% sequence identity to SEQ ID NO:1-8, 16 and 20.

36. The plant, seed or plant cell of any of embodiments 35-36, wherein the target site further comprises a polynucleotide of interest between the first recombination site and the second recombination site.

37. The plant, seed or plant cell of any one of embodiments 35-36, wherein at least one of the first and the second recombination sites comprises an FRT site, a mutant FRT site, a LOX site, or a mutant LOX site.

38. The plant, seed or plant cell of any one of embodiments 35-37, wherein the target site further comprises a third recombination site between the first and the second recombination site, wherein the third recombination site is dissimilar and non-recombinogenic to the first and the second recombination sites.

39. The plant, seed or plant cell of embodiment 38, wherein at least one of the first, the second, and the third recombination sites comprises FRT1 (SEQ ID NO: 9), FRT 5 (SEQ ID NO: 10), FRT6 (SEQ ID NO: 11), FRT12 (SEQ ID NO: 12) and FRT87 (SEQ ID NO: 13).

40. The plant, seed or plant cell of embodiment 38, wherein the first recombination site is FRT1 (SEQ ID NO: 9), the second recombination site is FRT12 (SEQ ID NO: 12), and the third recombination site is FRT87 (SEQ ID NO: 13).

41. The plant, seed, or plant cell of any one of embodiments 35-40, wherein said plant, seed or plant cell is from a monocot.

42. The plant, seed, or plant cell of embodiment 41, wherein said monocot is maize, wheat, rice, barley, sorghum, or rye.

43. The plant, seed, or plant cell of any one of embodiments 35-40, wherein said plant, seed or plant cell is from a dicot.

44. The plant, seed, or plant cell of embodiment 43, wherein said dicot is soybean, Brassica, sunflower, cotton, or alfalfa.

Recombinase Medicated DNA Casette exchange RMCE using different recombinase systems have been achieved successfully in several plants (Nanto K, Yamada-Watanabet K, Ebinuma H (2005) *Agrobacterium*-mediated RMCE approach for gene replacement. Plant Biotechnol J, 3: 203-214; Louwerse J D et al. 2007. Stable recombinase-mediated cassette exchange in *Arabidopsis* using *Agrobacterium tumefaciens*. Plant Physiol 145: 1282-1293; Li Z. et al. 2009, Site-specific integration of transgenes in soybean via recombinase-mediated DNA cassette exchange. Plant Physiol 151: 1087-1095). Groups of transgenes can be stacked to the same site through multiple rounds of RMCE (Li et al 2010, Published online before print August 2010, doi:10.1104/pp. 110.160093; Plant Physiology October 2010 vol. 154 no. 2 622-631). Taking advantage of reversible DNA cassette exchange in RMCE, an RMCE product can be used as a new target for subsequent SSI transformation. RMCE is a complex process especially when there are two targets, one on each homologous chromosome, and the two recombinase recognition sites involved are only partially incompatible (Li et al., 2009). The process is further complicated in gene stacking by using three recognition sites and large donor DNA containing multiple genes with some repeated sequences (Li et al 2010).

The DNA repair mechanisms of cells are the basis of transformation to introduce extraneous DNA or induce mutations on endogenous genes. DNA homologous recombination is a specialized way of DNA repair that the cells repair DNA damages using a homologous sequence. In plants, DNA homologous recombination happens at frequencies too low to be used in transformation until it has been found that the process can be stimulated by DNA double-strand breaks (Bibikova et al., (2001) Mol. Cell Biol. 21:289-297; Puchta and Baltimore, (2003) Science 300:763; Wright et al., (2005) Plant J. 44:693-705).

Recent developments in plant gene targeting demonstrate that endogenous genomic sites can be specifically targeted for modification through DNA double-strand break-induced homologous recombination (U.S. patent application Ser. No. 12/147,834, filed on Jun. 27, 2008 and U.S. provisional application 61/466,602 filed on Mar. 23, 2011, and herein incorporated by reference in their entirety). DNA double-strand breaks can be created with either designed zinc finger nucleases or modified homing endonucleases. Customized zinc finger nucleases have been employed to introduce successfully an herbicide resistance gene, PAT, to a tobacco (*Nicotiana tabacum*) endochitinase gene locus, a maize (*Zea mays*) inositol-1,3,4,5,6-petakisphosphate 2-kinase gene locus, or to introduce specific mutations to a tobacco acetolactate synthase gene to gain resistance to sulfonyl urea (Li. et al 2010). Similarly, an engineered I-CreI endonuclease derivative designed to recognize a selected sequence adjacent to the maize LIGULELESS1 gene has been used to produce mutations with small deletions or insertions specifically at expected cleavage sites (U.S. patent application Ser. No. 12/147,834, filed on Jun. 27, 2008).

The following examples are offered by way of illustration and not by way of limitation.

EXAMPLES

The present invention is further defined in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Such modifications are also intended to fall within the scope of the appended claims.

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kb" means kilobase(s).

Example 1

DNA Double-Strand-Break-Induced Alteration of an Endogenous Target Site Followed by Site Specific Integration FIG. 1 provides a non-limiting example of targeted integration of a target site for site-specific recombination at a double strand break induced by an endonuclease at an endogenous recognition site and subsequent modification of the integrated target site. In FIG. 1A, a plant having in its genome an endogenous recognition site for an endonuclease flanked by a first genomic region (DNA1) and a second genomic region (DNA2) is provided. A donor DNA is introduced into the plant cell comprising a nuclease gene for inducing a double strand break, a promoter, and a target site comprising two dissimilar and non-recombinogenic site-specific recombination sites (i.e. FRT1 and FRT87) and a first marker gene (Marker 1) whereby the target site is flanked by a first region of homology to DNA1 (HR1) and a second region of homology to DNA2 (HR2). The endonuclease induces a double strand break in the genomic DNA at the endogenous recognition site and the donor DNA and genomic DNA undergoes homologous recombination at the corresponding DNA1 and DNA2 regions. The resulting genomic structure with the integrated target site is depicted in FIG. 1D. The integrated target site can be altered by site-specific recombination by providing to the cell a transfer cassette comprising the same dissimilar and non-recombinogenic recombination sites as the integrated target site (i.e. FRT1 and FRT87), a second marker gene (Marker 2), and a gene of interest. In the presence of the appropriate recombinase (FLP recombinase), the integrated target site is altered by site-specific recombination and the resulting genomic target site comprises Marker 2 and the gene of interest (FIG. 1G).

Example 2

Transformation of Maize Immature Embryos

Transformation can be accomplished by various methods known to be effective in plants, including particle-mediated delivery, Agrobacterium-mediated transformation, PEG-mediated delivery, and electroporation.

a. Particle-Mediated Delivery

Transformation of maize immature embryos using particle delivery is performed as follows. Media recipes follow below.

The ears are husked and surface sterilized in 30% Clorox bleach plus 0.5% Micro detergent for 20 minutes, and rinsed two times with sterile water. The immature embryos are isolated and placed embryo axis side down (scutellum side up), 25 embryos per plate, on 560Y medium for 4 hours and then aligned within the 2.5-cm target zone in preparation for bombardment. Alternatively, isolated embryos are placed on 560 L (Initiation medium) and placed in the dark at temperatures ranging from 26° C. to 37° C. for 8 to 24 hours prior to placing on 560Y for 4 hours at 26° C. prior to bombardment as described above.

A plasmid comprising the Zm-BBM (also referred to as Zm-ODP2) coding sequence (set forth in SEQ ID NO: 9) operably linked to a promoter is constructed. This could be a weak promoter such as nos, a tissue-specific promoter, such as globulin-1 or oleosin, an inducible promoter such as In2, or a strong promoter such as ubiquitin plus a plasmid containing the selectable marker gene phosphinothricin N-acetyltransferase (PAT; Wohlleben et al. (1988) *Gene* 70:25 37) that confers resistance to the herbicide bialaphos. Furthermore, plasmids containing the double strand brake inducing agent and donor DNA such as PHP44285 or PHP44779 are constructed as described above and co-bombareded with the plasmids containing the developmental genes ODP2 (AP2 domain transcription factor ODP2 (Ovule development protein 2); US20090328252 A1) and Wushel.

The plasmids are precipitated onto 1.1 µm (average diameter) tungsten pellets using a calcium chloride ($CaCl_2$) precipitation procedure by mixing 100 µl prepared tungsten particles in water, 10 µl (1 µg) DNA in Tris EDTA buffer (1 µg total DNA), 100 µl 2.5 M CaCl2, and 10 µl 0.1 M spermidine. Each reagent is added sequentially to the tungsten particle suspension, with mixing. The final mixture is sonicated briefly and allowed to incubate under constant vortexing for 10 minutes. After the precipitation period, the tubes are centrifuged briefly, liquid is removed, and the particles are washed with 500 ml 100% ethanol, followed by a 30 second centrifugation. Again, the liquid is removed, and 105 µl 100% ethanol is added to the final tungsten particle pellet. For particle gun bombardment, the tungsten/DNA particles are briefly sonicated. 10 µl of the tungsten/DNA particles is spotted onto the center of each macrocarrier, after which the spotted particles are allowed to dry about 2 minutes before bombardment.

The sample plates are bombarded at level #4 with a Biorad Helium Gun. All samples receive a single shot at 450 PSI, with a total of ten aliquots taken from each tube of prepared particles/DNA.

Following bombardment, the embryos are incubated on 560P (maintenance medium) for 12 to 48 hours at temperatures ranging from 26 C to 37 C, and then placed at 26 C. After 5 to 7 days the embryos are transferred to 560R selection medium containing 3 mg/liter Bialaphos, and subcultured every 2 weeks at 26 C. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to a lighted culture room. Approximately 7-10 days later, developing plantlets are transferred to 272V hormone-free medium in tubes for 7-10 days until plantlets are well established. Plants are then transferred to inserts in flats (equivalent to a 2.5" pot) containing potting soil and grown for 1 week in a growth chamber, subsequently grown an additional 1-2 weeks in the greenhouse, then transferred to Classic 600 pots (1.6 gallon) and grown to maturity. Plants are monitored and scored for transformation efficiency, and/or modification of regenerative capabilities.

Initiation medium (560 L) comprises 4.0 g/l N6 basal salts (SIGMA C-1416), 1.0 ml/l Eriksson's Vitamin Mix (1000× SIGMA-1511), 0.5 mg/l thiamine HCl, 20.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature).

Maintenance medium (560P) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, 2.0 mg/l 2,4-D, and 0.69 g/l L-proline (brought to volume with D-I H2O following adjustment to pH 5.8 with KOH); 3.0 g/l Gelrite (added after bringing to volume with D-I H2O); and 0.85 mg/l silver nitrate (added after sterilizing the medium and cooling to room temperature).

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature).

Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I H2O following adjustment to pH 5.8 with KOH); 3.0 g/l Gelrite (added after bringing to volume with D-I H2O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H2O) (Murashige and Skoog (1962) Physiol. Plant. 15:473); 100 mg/l myo-inositol, 0.5 mg/l zeatin, 60 g/l sucrose, and 1.0 ml/l of 0.1 mM abscisic acid (brought to volume with polished D-I H2O after adjusting to pH 5.6); 3.0 g/l Gelrite (added after bringing to volume with D-I H2O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H2O), 0.1 g/l myo-inositol, and 40.0 g/l sucrose (brought to volume with polished D-I H2O after adjusting pH to 5.6); and 6 g/l bacto-agar (added after bringing to volume with polished D-I H2O), sterilized and cooled to 60° C.

b. *Agrobacterium*-Mediated Transformation

*Agrobacterium*-mediated transformation was performed essentially as described in Djukanovic et al. (2006) *Plant Biotech J* 4:345-57. Briefly, 10-12 day old immature embryos (0.8-2.5 mm in size) were dissected from sterilized kernels and placed into liquid medium (4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 68.5 g/L sucrose, 36.0 g/L glucose, pH 5.2). After embryo collection, the medium was replaced with 1 ml *Agrobacterium* at a concentration of 0.35-0.45 OD550. Maize embryos were incubated with *Agrobacterium* for 5 min at room temperature, then the mixture was poured onto a media plate containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 30.0 g/L sucrose, 0.85 mg/L silver nitrate, 0.1 nM acetosyringone, and 3.0 g/L Gelrite, pH 5.8. Embryos were incubated axis down, in the dark for 3 days at 20° C., then incubated 4 days in the dark at 28° C., then transferred onto new media plates containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.69 g/L L-proline, 30.0 g/L sucrose, 0.5 g/L MES buffer, 0.85 mg/L silver nitrate, 3.0 mg/L Bialaphos, 100 mg/L carbenicillin, and 6.0 g/L agar, pH 5.8. Embryos were subcultured every three weeks until transgenic events were identified. Somatic embryogenesis was induced by transferring a small amount of tissue onto regeneration medium (4.3 g/L MS salts (Gibco 11117), 5.0 ml/L MS Vitamins Stock Solution, 100 mg/L myo-inositol, 0.1 μM ABA, 1 mg/L IAA, 0.5 mg/L zeatin, 60.0 g/L sucrose, 1.5 mg/L Bialaphos, 100 mg/L carbenicillin, 3.0 g/L Gelrite, pH 5.6) and incubation in the dark for two weeks at 28° C. All material with visible shoots and roots were transferred onto media containing 4.3 g/L MS salts (Gibco 11117), 5.0 ml/L MS Vitamins Stock Solution, 100 mg/L myo-inositol, 40.0 g/L sucrose, 1.5 g/L Gelrite, pH 5.6, and incubated under artificial light at 28° C. One week later, plantlets were moved into glass tubes containing the same medium and grown until they were sampled and/or transplanted into soil.

Example 3

Transient Expression of BBM Enhances Transformation

Parameters of the transformation protocol can be modified to ensure that the BBM activity is transient. One such method involves precipitating the BBM-containing plasmid in a manner that allows for transcription and expression, but precludes subsequent release of the DNA, for example, by using the chemical PEI. In one example, the BBM plasmid is precipitated onto gold particles with PEI, while the transgenic expression cassette (UBI::moPAT-GFPm::PinII; moPAT is the maize optimized PAT gene) to be integrated is precipitated onto gold particles using the standard calcium chloride method.

Briefly, gold particles were coated with PEI as follows. First, the gold particles were washed. Thirty-five mg of gold particles, 1.0 in average diameter (A.S.I. #162-0010), were weighed out in a microcentrifuge tube, and 1.2 ml absolute EtOH was added and vortexed for one minute. The tube was incubated for 15 minutes at room temperature and then centrifuged at high speed using a microfuge for 15 minutes at 4° C. The supernatant was discarded and a fresh 1.2 ml aliquot of ethanol (EtOH) was added, vortexed for one minute, centrifuged for one minute, and the supernatant again discarded (this is repeated twice). A fresh 1.2 ml aliquot of EtOH was added, and this suspension (gold particles in EtOH) was stored at −20° C. for weeks. To coat particles with polyethylamine (PEI; Sigma #P3143), 250 μl of the washed gold particle/EtOH mix was centrifuged and the EtOH discarded. The particles were washed once in 100 μl ddH2O to remove residual ethanol, 250 μl of 0.25 mM PEI was added, followed by a pulse-sonication to suspend the particles and then the tube was plunged into a dry ice/EtOH bath to flash-freeze the suspension, which was then lyophilized overnight. At this point, dry, coated particles could be stored at −80° C. for at least 3 weeks. Before use, the particles were rinsed 3 times with 250 µl aliquots of 2.5 mM HEPES buffer, pH 7.1, with 1× pulse-sonication, and then a quick vortex before each centrifugation. The particles were then suspended in a final volume of 250 µl HEPES buffer. A 25 µl aliquot of the particles was added to fresh tubes before attaching DNA. To attach uncoated DNA, the particles were pulse-sonicated, then 1 µg of DNA (in 5 µl water) was added, followed by mixing by pipetting up and down a few times with a Pipetteman and incubated for 10 minutes. The particles were spun briefly (i.e. 10 seconds), the supernatant removed, and 60 µl EtOH added. The particles with PEI-precipitated DNA-1 were washed twice in 60 µl of EtOH. The particles were centrifuged, the supernatant discarded, and the particles were resuspended in 45 µl water. To attach the second DNA (DNA-2), precipitation using TFX-50 was used. The 45 µl of particles/DNA-1 suspension was briefly sonicated, and then 5 µl of 100 ng/µl of DNA-2 and 2.5 µl of TFX-50 were added. The solution was placed on a rotary shaker for 10 minutes, centrifuged at 10,000 g for 1 minute. The supernatant was removed, and the particles resuspended in 60 µl of EtOH. The solution was spotted onto macrocarriers and the gold particles onto which DNA-1 and DNA-2 had been sequentially attached were delivered into scutellar cells of 10 DAP Hi-II immature embryos using a standard protocol for the PDS-1000. For this experiment, the DNA-1 plasmid contained a UBI::RFP::pinII expression cassette, and DNA-2 contained a UBI::CFP::pinII expression cassette. Two days after bombardment, transient expression of both the CFP and RFP fluorescent markers was observed as numerous red & blue cells on the surface of the immature embryo. The embryos were then placed on non-selective culture medium and allowed to grow for 3 weeks before scoring for stable colonies. After this 3-week period, 10 multicellular, stably-expressing blue colonies were observed, in comparison to only one red colony. This demonstrated that PEI-precipitation could be used to effectively introduce DNA for transient expression while dramatically reducing integration of the PEI-introduced DNA and thus reducing the recovery of RFP-expressing transgenic events. In this manner, PEI-precipitation can be used to deliver transient expression of BBM and/or WUS2.

For example, the particles are first coated with UBI::BBM::pinII using PEI, then coated with UBI::moPAT~YFP using TFX-50, and then bombarded into scutellar cells on the surface of immature embryos. PEI-mediated precipitation results in a high frequency of transiently expressing cells on the surface of the immature embryo and extremely low frequencies of recovery of stable transformants (relative to the TFX-50 method). Thus, it is expected that the PEI-precipitated BBM cassette expresses transiently and stimulates a burst of embryogenic growth on the bombarded surface of the tissue (i.e. the scutellar surface), but this plasmid will not integrate. The PAT~GFP plasmid released from the Ca++/gold particles is expected to integrate and express the selectable marker at a frequency that results in substantially improved recovery of transgenic events. As a control treatment, PEI-precipitated particles containing a UBI::GUS::pinII (instead of BBM) are mixed with the PAT~GFP/Ca++ particles. Immature embryos from both treatments are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

As an alternative method, the BBM plasmid is precipitated onto gold particles with PEI, and then introduced into scutellar cells on the surface of immature embryos, and subsequent transient expression of the BBM gene elicits a rapid proliferation of embryogenic growth. During this period of induced growth, the explants are treated with *Agrobacterium* using standard methods for maize (see Example 1), with T-DNA delivery into the cell introducing a transgenic expression cassette such as UBI::moPAT~GFPm::pinII. After co-cultivation, explants are allowed to recover on normal culture medium, and then are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

It may be desirable to "kick start" callus growth by transiently expressing the BBM and/or WUS2 polynucleotide products. This can be done by delivering BBM and WUS2 5'-capped polyadenylated RNA, expression cassettes containing BBM and WUS2 DNA, or BBM and/or WUS2 proteins. All of these molecules can be delivered using a biolistics particle gun. For example 5'-capped polyadenylated BBM and/or WUS2 RNA can easily be made in vitro using Ambion's mMessage mMachine kit. RNA is co-delivered along with DNA containing a polynucleotide of interest and a marker used for selection/screening such as Ubi::moPAT~GFPm::PinII. It is expected that the cells receiving the RNA will immediately begin dividing more rapidly and a large portion of these will have integrated the agronomic gene. These events can further be validated as being transgenic clonal colonies because they will also express the PAT~GFP fusion protein (and thus will display green fluorescence under appropriate illumination). Plants regenerated from these embryos can then be screened for the presence of the polynucleotide of interest.

Example 4

Meganuclease Generated Recombinant Target Loci (RTL) for FLP/FRT Site Specific Integration (SSI) in Maize a. Introducing FRT Sites at a Specific Maize Genomic Locus.

Maize lines comprising an endogenous recognition sequence in their genome were contacted with an engineered meganuclease derived from I-CreI designed to specifically recognize and create a double-strand break in the endogenous recognition sequence. Immature embryos comprising an endogenous recognition site were contacted with the components described below, events selected and characterized.

Plasmid PHP36070 (SEQ ID NO: 14) was used to create a transgenic insertion at the LIG3-4 locus. The LIG3-4 locus is described in U.S. patent application Ser. No. 12/147,834 filed on Jun. 27, 2008 which is herein incorporated by reference in its entirety. In short, an endogenous maize genomic sequence was selected for design of a custom double-strand break inducing agent derived from I-CreI meganuclease.

The LIG3-4 recognition site is a 22 bp polynucleotide having the following sequence:

(SEQ ID NO: 16)
ATATACCTCACAC▼GTACGCGTA

The double strand break site and overhang region is shown in bold, the enzyme cuts after C13, as indicated by the solid triangle. The I-CreI meganuclease was modified to produce the LIG3-4 meganuclease designed to recognize the LIG3-4 recognition sequence as described in U.S. patent application Ser. No. 12/147,834 filed on Jun. 27, 2008. PHP36070 contains the LIG3-4 meganuclease plant optimized DNA sequence transcribed by the maize ubiquitin promoter (FIG. 2). Homologous region 1 (HR1, SEQ ID NO: 17) and homologous region 2 (HR2, SEQ ID NO: 18) are the regions of maize homology that flank LIG3-4 recognition site. A marker cassette consisting of the maize ubiquitin promoter (UBI promoter) driving the herbicide resistance gene mopat (MO-PAT, FIG. 2) and a potato protease inhibitor II (PINII) terminator was located between the two HR regions. MoPAT encodes a phosphinothricin acetyltransferase. The marker cassette also included two non-identical FRT sites, FRT1 and FRT87, to allow for site specific integration mediated by FLP recombinase. The positioning of the FRT sites between the promoter and mopat gene and following the PINII has been described in U.S. Pat. No. 7,820,880 (filed on Nov. 16, 2008 and issued on Oct. 26, 2010) and incorporated by reference herein. *Agrobacterium* borders are shown as RB and LB in FIG. 2, however this construct was not introduced via *Agrobacterium*. Instead, PHP36070 was introduced by particle bombardment and co-bombarded with additional plasmids, PHP21875 (UBI PRO-bbm) and PHP21139 (IN2-2 PRO-wus), expressing the maize bbm gene and maize wuschel gene, respectively to enhance the frequency of recovery of transgenic insertions (as described in Example 2 and 3, PCT/US2010/062531).

Plasmid PHP44779 (SEQ ID NO: 19) was used to create a transgenic insertion at the MHP locus on maize chromosome 1.

The MHP locus is described in U.S. patent application 61/499,443 filed on Jun. 21, 2011 which is herein incorporated by reference in its entirety. In short, an endogenous maize genomic target recognition sequence was selected for design of a custom double-strand break inducing agent derived from I-CreI meganuclease. The MHP14 recognition site is a 22 bp polynucleotide having the following sequence: (SEQ ID NO: 20): caaacagattcacgtcagattt.

PHP44779 (FIG. 2) contains the MHP14 meganuclease plant optimized DNA sequence (SEQ ID NO 21) transcribed by the maize ubiquitin promoter Homologous region 1 (also referred to as ZM-Seq8 MHP14-1 in FIG. 3, SEQ ID NO: 22) and homologous region 2 (also referred to as ZM-Seq9 MHP14-2 in FIG. 3, SEQ ID NO: 23) are the regions of maize homology that flank the MHP14 recognition site. A marker cassette consisting of the maize ubiquitin promoter (UBI promoter) driving the herbicide resistance gene mopat and a potato protease inhibitor II (PINII) terminator was located between the two HR regions (FIG. 3). PHP44779 was introduced by particle bombardment and co-bombarded with the additional plasmids, PHP44779 and PHP31729 (OLE PRO-bbm) and PHP21139 (IN2-2 PRO-wus), expressing the maize bbm gene and maize wuschel gene, respectively, to enhance the frequency of recovery of transgenic insertions (Example 2 and 3, PCT/US2010/062531).

Transgenic callus bombarded with either PHP36070 or PHP44779 and showing resistance to bialaphos was regenerated into plants. Leaf tissue of transgenic plants was used for molecular analysis to confirm that the insertion or recombination occurred at the specific target sites for each meganuclease. The desired molecular configuration of the transgenic insert of these experiments is detailed in FIG. 4. FIG. 4 shows a graphic representation of the transgenic insertion site following homologous recombination mediated by meganuclease induced double stranded breaks. The meganuclease can cut the maize genome at a specific target sequence leaving a double stranded break which subsequently promotes the cell's DNA recombination and repair mechanisms. A copy of the plasmid with homologous regions is in the vicinity and gets recombined into the genome creating a transgenic insertion site via homologous recombination. The recombination exchange places a fragment of the transformation plasmid in the insertion site which contains only the marker cassette with associated FLP recombinase sites. Ideally, the HR regions of the construct have inserted in a way that they are seamless with the existing genome sequence of the target chromosome. The meganuclease gene is left behind on the construct and degraded.

PCR and Southern analysis were used to obtain information about the molecular structure of the transgene insertions. The desired molecular configurations containing the marker gene cassette with associated FLP/FRT SSI features (FIG. 4) were obtained as a small percentage of the total number of insertion events.

B. Characterization of Recombinant Target Loci (RTL) for FLP/FRT Site Specific Integration at a Specific LIG3-4 or MHP Maize Genomic Site.

Transgenic plants regenerated form callus bombarded with either PHP36070 or PHP44779 were grown in the greenhouse to maturity and seed was harvested. The next generation seed from self pollinations was used to obtain a homozygous seed supply, by using quantitative PCR (QPCR) to screen populations from a self pollination of either the first or second generation. Homozygous individuals identified by QPCR were self-pollinated to increase homozygous seed supply and were carried on to non-transgenic plants to provide a supply of immature embryos for FLP/FRT SSI transformation experiments. Large numbers of immature embryos heterozygous for the transgenic insertion at the LIG3-4 or MHP site were obtained for these experiments by carrying pollen from populations of homozygous LIG3-4 or MHP plants to populations of non-transgenic plants of the same corn genotype supplied for embryo source.

Transgenic plants containing the desired insertions (FIG. 4) from meganuclease facilitated homologous recombination were identified and became recombinant target loci (RTL) for FLP/FRT site specific integration.

Methods for site specific integration using FLP recombinase include the combination of a 'target' transgenic locus, also known as an Recombinant Trait Locus (RTL), with two non-identical FRT sites and a 'donor' plasmid or insert with the same two non-identical FRT sites (U.S. Pat. No. 7,462,766 filed May 4, 2006 and issued Dec. 9, 2008). FLP recombinase binds to the FRT sites of both target and donor, bring the FRT sites together in the cell, and then recombine FRT sites of identical sequence.

A LIG-3-4 event (E8815.112.3.28) and MHP14 events containing the desired configuration and non-identical FRT sites (FIG. 4) were identified.

C. Recombinases Medicated DNA Casette Exchange in SSI Sites Created at Specific Genomic Loci.

Maize transformation of events containing the recombinant target loci (RTL) (described in Example 4 B) for FLP/FRT SSI at a specific LIG3-4 or MHP locus was accomplished by particle bombardment (also referred herein as SSI transformation). For each experiment, several plasmids were co-bombarded including the Transfer Cassette plasmids PHP27064 (SEQ ID NO:24) or PHP44951 (SEQ ID NO:25)(FIG. 5), a plasmid to transiently express FLP recombinase (PHP5096, UBI PRO-flp), and plasmids to transiently express bbm and wus (PHP31729, PHP21139).

Two independent Transfer Cassette plasmids (PHP27064 (SEQ ID NO:24) or PHP44951 (SEQ ID NO:25) were used to test the effect of molecule size on transformation frequency at the LIG3-4 and MHP14 RTL, as well as to introduce multiple genes that allow the measurement of expression levels in the case of PHP44951 (FIG. 5). Both transfer cassettes includes an FRT1 upstream of the first gene and FRT87 at the 3' end of the terminator for the last gene. This allows functional recombination with the target sites that have FRT sites in similar positions. The upstream gene in the donor does not have its own promoter because it is activated by the ubiquitin promoter in the target site following recombination. The integration of the transfer cassettes at the MHP14 site after FLP recombinase mediated site specific integration is shown in FIG. 6.

The SSI process involves recombination between the FRT1 and FRT87 sites of the target and transfer cassette in a process called double reciprocal crossover. The end result is that the mopat gene (FIG. 4) is replaced at the SSI target by gat4621 and zs-yellow1 N1 when donor PHP27064 is bombarded or those genes plus gus and mopat if PHP44951 is bombarded.

Table 3 shows QPCR results from a number of independent FLP/FRT SSI transformation experiments involving a relatively large number of treated immature embryos. RMCE events were obtained from the LIG3-4 RTL. Table 3 also illustrates that the RMCE frequency may be affected by the size of the transfer cassette. A higher RMCE frequency was observed for the smaller transfer cassette PHP27064 when compared to the larger PHP44951.

TABLE 3

RMCE frequencies at the LIG3-4 target site. The LIG3/4 RTL was obtained from meganuclease assisted homologous recombination.

| RTL | Transfer Cassette | Embryo TRT | # RMCE (T0 plants) | RMCE FREQ | YFP expression in callus | Regeneration |
|---|---|---|---|---|---|---|
| LIG3/4 E8815.112.3.28 | PHP27064 | 2696 | 17 | 1.10 | Bright | Good |
| LIG3/4 E8815.112.3.28 | PHP44951 | 2693 | 10 | 0.69 | Bright | OK |

Embryo TRT = the number of immature embryos treated for SSI transformation; RMCE = recombinase mediated cassette exchange is the term given to the desired molecular result from FLP/FRT SSI transformation; RMCE FREQ = the transformation frequency on a per embryo basis of obtaining RMCE events.

Similar FLP/FRT SSI transformation data was generated the MHP14 target site as shown in Table 4.

TABLE 4

RMCE frequencies at the MHP14 target site. The MHP14 RTL was obtained from meganuclease assisted homologous recombination.

| RTL | Transfer Cassette | Embryo TRT | # RMCE (T0 plants) | RMCE FREQ |
|---|---|---|---|---|
| MHP14 | PHP27064 | 3753 | 19 | 0.51 |
| MHP14 | PHP44951 | 3696 | 2 | 0.05 |

Table 4 indicates that RMCE events were obtained from the MHP14 SSI target site RTL. As with the Lig3-4 site, a higher RMCE frequency was observed at the MHP14 site with the smaller transfer cassette PHP27064 when compared to PHP44951.

Table 3 and Table 4 clearly demonstrate that we can obtain targeted integration of a target site for site-specific recombination at a double strand break induced by a meganuclease at an endogenous recognition site and subsequent modify the integrated target site by RMCE.

Example 5

Creation of FRT1/FRT87 Sites in the TS14 Target Site in Soybean Genome by Soybean TS14 Meganuclease Soybean lines comprising an endogenous recognition sequence in their genome were contacted with an engineered meganuclease derived from I-CreI designed to specifically recognize and create a double-strand break in the endogenous recognition sequence. Immature embryos comprising an endogenous recognition site were contacted with the components described below, events selected and characterized.

In order to introduce the FRT1/FRT87 sites into the TS14 recognition site (SEQ ID NO:2) in the soybean genome, two expression cassettes (RTW347 and RTW365) were used. RTW347 (SEQ ID NO: 27) contains the plant optimized DNA sequence encoding the TS14 meganuclease (SEQ ID NO:26) driven by the soybean UBQ promoter and PinII terminator. RTW365 (SEQ ID NO:28) is the Transfer Cassette construct in which the FRT1/FRT87 sites are flanking the Gm-HRA::Gm-ALS terminator. The Gm-HRA gene was driven by the soybean SAMS promoter. The SAMS promoter::FRT1::Gm-HRA::Gm-ALS Terminator::FRT87 cassette is flanked by the 1000 bp homologous region1 (SEQ ID NO: 35) and 928 bp region2 (SEQ ID NO:36) flanking the TS14 recognition site. The TS14 recognition site sequence, the plant-optimized nucleotide sequence of the TS14 meganuclease homologous region1 and region2 have been disclosed in U.S. provisional application 61/466,602 filed on Mar. 23, 2011 which is herein incorporated by reference in their entirety.

RTW347 and RTW365 were co-bombarded into soybean cells using standard soybean transformation methods. qPCR and genomic PCR were used to identify the transgene integration event containing the SAMS promoter::FRT1:: GM-HRA::GM-ALS Terminator::FRT87. The qPCR assay specific to the TS14 target sequence was developed to identify sequence changes in the region. The primers (Mega14-13F, Mega14-128R and probe Mega14-85T), were used to identify the transgenic events with the TS14 target sites reduced to 1 or 0 copy as compared to the 2 copies in the wild type soybean genome. The border specific genomic PCR assays were used to further identify the transgene integration event. For example, the primer set WOL192 (SEQ ID NO:29) and WOL311 (SEQ ID NO:30) were designed and used to amplify the left border integration. The WOL192 is a sequence specific primer located in soybean genome 5' beyond the TS14 HR1 region and the WOL311 is a sequence specific primer to the 5' SAMS promoter in the reverse orientation. A 1334 bp PCR product (SEQ ID NO:31) can only be obtained when the RTW365 repair DNA get integrated by homologous integration enable by TS14 meganuclease. Another set of primer WOL312 (SEQ ID NO:32) and WOL193 (SEQ ID NO:33) were also designed and used to amplify the right border integration. The WOL312 is the sense primer from the GM-ALS terminator and the WOL193 is a sequence specific primer located in soybean genome 3' beyond the TS14 HR2 region. A 1620 bp PCR product (SEQ ID NO:34) can only be obtained when the RTW365 repair DNA get integrated by homologous integration enable by TS14 meganuclease. For the TS14 target site, 18 qPCR positive events were identified from total 68 events by qPCR analyses. Out of the 18 qPCR positive events, three events were confirmed to be perfect TS14 meganuclease mediated SAMS promoter::FRT1::GM-HRA::GM-ALS Terminator::FRT87 transgene integration events by homologous recombination. The Introduction of the FRT1 and FRT87 sites in the soybean TS14 target provided the ability to use the FLP/FRT technology to perform gene stacking by the SSI technology.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for introducing into the genome of a plant cell a target site for site-specific integration, the method comprising:

(a) providing a plant cell comprising in its genome an endogenous recognition site for an engineered meganuclease, wherein the endogenous recognition site is located between a first and a second genomic region, and wherein the endogenous recognition site is selected from the group consisting of SEQ ID NO: 1, 2, 3, 4, 5, 6, 7, and 8;

(b) providing a donor DNA comprising the target site for site-specific integration located between a first region of homology to said first genomic region and a second region of homology to said second genomic region, wherein the target site comprises a first and a second recombination site, and wherein the first and the second recombination sites are dissimilar and non-recombinogenic with respect to one another;

(c) contacting the plant cell with the donor DNA and the engineered meganuclease, wherein the engineered meganuclease induces a double-strand break in said endogenous recognition site; and (d) identifying at least one plant cell from (c) comprising in its genome the target site integrated at the endogenous recognition site.

2. The method of claim 1, wherein the first region of homology further comprises a first fragment of said endogenous recognition site of (a), and wherein the second region of homology comprises a second fragment of said endogenous recognition site of (a), wherein the first and second fragments are dissimilar.

3. The method of claim 1, wherein the first region of homology further comprises the first 13 bases of said endogenous recognition site of (a), and wherein the second region of homology comprises the last 9 bases of said endogenous recognition site of (a).

4. The method of claim 1, further comprising recovering a fertile plant from the cell of (d), the fertile plant comprising in its genome the target site integrated into the endogenous recognition site.

5. The method of claim 1, wherein the target site further comprises a polynucleotide of interest between the first recombination site and the second recombination site.

6. The method of claim 1, wherein at least one of the recombination sites comprises a site selected from the group consisting of an FRT site, a mutant FRT site, a LOX site, and a mutant LOX site.

7. The method of claim 1, wherein the target site further comprises a third recombination site between the first and the second recombination site, wherein the third recombination site is dissimilar and non-recombinogenic to the first and the second recombination sites.

8. The method of claim 7, wherein at least one of the recombination sites comprises a site selected from the group consisting of FRT1 (SEQ ID NO: 9), FRT 5(SEQ ID NO: 10), FRT6 (SEQ ID NO: 11), FRT12 (SEQ ID NO: 12) and FRT87 (SEQ ID NO:13).

9. The method of claim 7, wherein the first recombination site is FRT1 (SEQ ID NO: 9), the second recombination site is FRT12 (SEQ ID NO: 12), and the third recombination site is FRT87 (SEQ ID NO: 13).

10. The method of claim 1, wherein the engineered meganuclease is derived from I-CreI.

11. The method of claim 1, wherein said plant cell is from a dicot.

12. The method of claim 11, wherein said dicot is soybean.

13. A method of integrating a polynucleotide of interest into a target site in the genome of a plant cell, the method comprising:
  (a) providing at least one plant cell comprising in its genome a target site for site-specific integration, wherein the target site is integrated into an endogenous recognition site for an engineered meganuclease, wherein the endogenous recognition site is selected from the group consisting of SEQ ID NO: 1, 2, 3, 4, 5, 6, 7, and 8, and wherein the target site is,
    (i) a target site comprising a first and a second recombination site; or
    (ii) the target site of (i) further comprising a third recombination site between the first recombination site and the second recombination site,
  wherein the engineered meganuclease induces a double-strand break in the endogenous recognition site, wherein the first, the second, and the third recombination sites are dissimilar and non-recombinogenic with respect to one another,
  (b) introducing into the plant cell of (a) a transfer cassette comprising,
    (iii) the first recombination site, a first polynucleotide of interest, and the second recombination site,
    (iv) the second recombination site, a second polynucleotide of interest, and the third recombination sites, or
    (v) the first recombination site, a third polynucleotide of interest, and the third recombination sites;
  (c) providing a recombinase that recognizes and implements recombination at the first and the second recombination sites, at the second and the third recombination sites, or at the first and third recombination sites; and
  (d) selecting at least one plant cell comprising integration of the transfer cassette at the target site.

14. The method of claim 13, further comprising recovering a fertile plant from the plant cell of (d), the fertile plant comprising in its genome the transfer cassette at the target site.

15. The method of claim 13, wherein at least one of the first, the second, and the third polynucleotides of interest comprises a nucleotide sequence for gene silencing, a nucleotide sequence encoding a phenotypic marker, or a nucleotide sequence encoding a protein providing an agronomic advantage.

16. The method of claim 13, wherein providing the recombinase comprises integrating into the genome of the plant cell a nucleotide sequence encoding the recombinase.

17. The method of claim 13, wherein the transfer cassette further comprises at least one coding region operably linked to a promoter that drives expression in the plant cell.

18. The method of claim 13, wherein the transfer cassette further comprises a coding region operably linked to a promoter that drives expression in the plant cell, wherein the coding region encodes a recombinase that facilitates recombination between, the first and the second recombination sites of the transfer cassette and the target site, the second and the third recombination sites of the transfer cassette and the target site, or the first and the third recombination sites of the transfer cassette and the target site.

19. The method of claim 13, wherein at least one of the recombination sites comprises a site selected from the group consisting of an FRT site, a mutant FRT site, a LOX site, and a mutant LOX site.

20. The method of claim 13, wherein the first recombination site is FRT1 (SEQ ID NO: 9), the second recombination site is FRT12 (SEQ ID NO: 12), and the third recombination site is FRT87 (SEQ ID NO: 13).

21. The method of claim 13, wherein the recombinase is FLP.

22. The method of claim 21, wherein the FLP has been synthesized using maize-preferred codons.

23. The method of claim 13, wherein said plant cell is from a dicot.

24. The method of claim 23, wherein said dicot is soybean.

25. A plant cell, plant part, plant, or seed comprising the transfer cassette integrated at the target site according to the method of claim 13.

26. A plant, seed or plant cell comprising in its genome a target site for site-specific integration, wherein the target site is integrated into an endogenous recognition site for an engineered meganuclease, wherein the endogenous recognition site is selected from the group consisting of SEQ ID NO: 1, 2, 3, 4, 5, 6, 7, and 8, wherein the target site comprises in the following order:
  (a) a first recombination site;
  (b) a second recombination site, and
wherein the first and the second recombination sites are dissimilar and non-recombinogenic with respect to one another.

27. The plant, seed or plant cell of claim 26, wherein the target site further comprises a polynucleotide of interest between the first recombination site and the second recombination site.

28. The plant, seed or plant cell of claim 26, wherein at least one of the recombination sites comprises a site selected from the group consisting of an FRT site, a mutant FRT site, a LOX site, and a mutant LOX site.

29. The plant, seed or plant cell of claim 26, wherein the target site further comprises a third recombination site between the first and the second recombination site, wherein the third recombination site is dissimilar and non-recombinogenic to the first and the second recombination sites.

30. The plant, seed or plant cell of claim 29, wherein at least one of the recombination sites comprises a site selected from the group consisting of FRT1 (SEQ ID NO: 9), FRT 5 (SEQ ID NO: 10), FRT6 (SEQ ID NO: 11), FRT12 (SEQ ID NO: 12) and FRT87 (SEQ ID NO: 13).

31. The plant, seed or plant cell of claim 29, wherein the first recombination site is FRT1 (SEQ ID NO: 9), the second recombination site is FRT12 (SEQ ID NO: 12), and the third recombination site is FRT87 (SEQ ID NO: 13).

32. The plant, seed, or plant cell of claim 26, wherein said plant, seed or plant cell is from a dicot.

33. The plant, seed, or plant cell of claim 32, wherein said dicot is soybean.

* * * * *